United States Patent
Shelton, IV et al.

(10) Patent No.: US 9,295,514 B2
(45) Date of Patent: Mar. 29, 2016

(54) SURGICAL DEVICES WITH CLOSE QUARTER ARTICULATION FEATURES

(71) Applicant: Ethicon Endo-Surgery, Inc., Cincinnati, OH (US)

(72) Inventors: Frederick E. Shelton, IV, Hillsboro, OH (US); Chester O. Baxter, III, Loveland, OH (US); Jeffrey S. Swayze, Hamilton, OH (US); John R. Dugan, Lebanon, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 42 days.

(21) Appl. No.: 14/015,193

(22) Filed: Aug. 30, 2013

(65) Prior Publication Data

US 2015/0066022 A1  Mar. 5, 2015

(51) Int. Cl.
*A61B 18/14* (2006.01)
*A61B 18/08* (2006.01)
(Continued)

(52) U.S. Cl.
CPC ......... *A61B 18/082* (2013.01); *A61B 17/22004* (2013.01); *A61B 18/1445* (2013.01); *A61B 17/320092* (2013.01); *A61B 2017/003* (2013.01); *A61B 2017/00309* (2013.01); *A61B 2017/00314* (2013.01); *A61B 2017/2903* (2013.01);
(Continued)

(58) Field of Classification Search
CPC ............. A61B 18/085; A61B 18/1442; A61B 18/1447; A61B 18/1445; A61B 2018/1455; A61B 17/28; A61B 17/2804; A61B 17/2812; A61B 2017/2905; A61B 2017/2908; A61B 2017/2903; A61B 2017/2927; A61B 2017/2929; A61B 2017/2933; A61B 2017/2936; A61B 2017/2939; A61B 2017/2938

USPC ............... 606/51, 52, 205, 207, 208
See application file for complete search history.

(56) References Cited

U.S. PATENT DOCUMENTS 2,366,274 A  1/1945  Luth et al.
2,458,152 A  1/1949  Eakins
(Continued)

FOREIGN PATENT DOCUMENTS

DE  10201569 A1  7/2003
EP  0340803 B1  8/1993
(Continued)

OTHER PUBLICATIONS

International Search Report for PCT/US2014/052100, Mar. 11, 2015 (7 pages).
(Continued)

*Primary Examiner* — Michael Peffley
*Assistant Examiner* — Thomas Giuliani

(57) ABSTRACT

The disclosure provides various apparatuses comprising a shaft section extending longitudinally along a first plane. An end effector comprises a first jaw and a second jaw configured to pivotally open and close in a second plane relative to the first plane about a pivot point. The first plane is orthogonal to the second plane. An articulation section is disposed between the shaft section and the end effector. The articulation section is configured to articulate in the second plane relative to the first plane in response to a rotatable articulation control mechanism. Also disclosed are configuration where at least one of the first and second jaws comprises an electrode. Also disclosed are configurations in which the end effector pivots and articulates about the same pivot point.

7 Claims, 29 Drawing Sheets

(51) Int. Cl.
*A61B 17/22* (2006.01)
*A61B 18/00* (2006.01)
*A61B 17/32* (2006.01)
*A61B 17/29* (2006.01)
*A61B 18/12* (2006.01)
*A61B 17/00* (2006.01)

(52) U.S. Cl.
CPC . *A61B2017/2927* (2013.01); *A61B 2017/2936* (2013.01); *A61B 2017/2938* (2013.01); *A61B 2017/2939* (2013.01); *A61B 2017/2941* (2013.01); *A61B 2017/2943* (2013.01); *A61B 2018/0063* (2013.01); *A61B 2018/00184* (2013.01); *A61B 2018/00202* (2013.01); *A61B 2018/00601* (2013.01); *A61B 2018/00916* (2013.01); *A61B 2018/1226* (2013.01); *A61B 2018/1455* (2013.01)

(56) References Cited

U.S. PATENT DOCUMENTS

| | | |
|---|---|---|
| 2,510,693 A | 6/1950 | Green |
| 3,166,971 A | 1/1965 | Stoecker |
| 3,580,841 A | 5/1971 | Cadotte et al. |
| 3,703,651 A | 11/1972 | Blowers |
| 3,777,760 A | 12/1973 | Essner |
| 4,005,714 A | 2/1977 | Hiltebrandt |
| 4,034,762 A | 7/1977 | Cosens et al. |
| 4,058,126 A | 11/1977 | Leveen |
| 4,220,154 A | 9/1980 | Semm |
| 4,237,441 A | 12/1980 | van Konynenburg et al. |
| 4,281,785 A | 8/1981 | Brooks |
| 4,304,987 A | 12/1981 | van Konynenburg |
| 4,463,759 A | 8/1984 | Garito et al. |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,617,927 A | 10/1986 | Manes |
| 4,735,603 A | 4/1988 | Goodson et al. |
| 4,761,871 A | 8/1988 | O'Connor et al. |
| 4,830,462 A | 5/1989 | Karny et al. |
| 4,849,133 A | 7/1989 | Yoshida et al. |
| 4,860,745 A | 8/1989 | Farin et al. |
| 4,878,493 A | 11/1989 | Pasternak et al. |
| 4,910,389 A | 3/1990 | Sherman et al. |
| 4,920,978 A | 5/1990 | Colvin |
| 4,936,842 A | 6/1990 | D'Amelio et al. |
| 5,061,269 A | 10/1991 | Muller |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,160,334 A | 11/1992 | Billings et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,217,460 A | 6/1993 | Knoepfler |
| 5,234,428 A | 8/1993 | Kaufman |
| 5,258,006 A | 11/1993 | Rydell et al. |
| 5,285,945 A | 2/1994 | Brinkerhoff et al. |
| 5,290,286 A | 3/1994 | Parins |
| 5,309,927 A | 5/1994 | Welch |
| 5,318,564 A | 6/1994 | Eggers |
| 5,318,589 A | 6/1994 | Lichtman |
| 5,330,471 A | 7/1994 | Eggers |
| 5,339,723 A | 8/1994 | Huitema |
| 5,342,359 A | 8/1994 | Rydell |
| 5,361,583 A | 11/1994 | Huitema |
| 5,383,874 A | 1/1995 | Jackson et al. |
| 5,387,207 A | 2/1995 | Dyer et al. |
| 5,389,098 A | 2/1995 | Tsuruta et al. |
| 5,395,312 A | 3/1995 | Desai |
| 5,395,363 A | 3/1995 | Billings et al. |
| 5,395,364 A | 3/1995 | Anderhub et al. |
| 5,395,900 A | 3/1995 | Slater et al. |
| 5,403,312 A | 4/1995 | Yates et al. |
| 5,417,709 A | 5/1995 | Slater |
| 5,428,504 A | 6/1995 | Bhatla |
| 5,429,131 A | 7/1995 | Scheinman et al. |
| 5,443,463 A | 8/1995 | Stern et al. |
| 5,445,638 A | 8/1995 | Rydell et al. |
| 5,451,227 A | 9/1995 | Michaelson |
| 5,458,598 A | 10/1995 | Feinberg et al. |
| 5,465,895 A | 11/1995 | Knodel et al. |
| 5,472,443 A | 12/1995 | Cordis et al. |
| 5,476,479 A | 12/1995 | Green et al. |
| 5,480,409 A | 1/1996 | Riza |
| 5,484,436 A | 1/1996 | Eggers et al. |
| 5,486,189 A | 1/1996 | Mudry et al. |
| 5,496,317 A | 3/1996 | Goble et al. |
| 5,504,650 A | 4/1996 | Katsui et al. |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,542,916 A | 8/1996 | Hirsch et al. |
| 5,558,671 A | 9/1996 | Yates |
| 5,563,179 A | 10/1996 | Stone et al. |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,611,813 A | 3/1997 | Lichtman |
| 5,618,307 A | 4/1997 | Donlon et al. |
| 5,624,452 A | 4/1997 | Yates |
| 5,647,871 A | 7/1997 | Levine et al. |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,674,219 A | 10/1997 | Monson et al. |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,713,896 A | 2/1998 | Nardella |
| 5,716,366 A | 2/1998 | Yates |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,779,701 A | 7/1998 | McBrayer et al. |
| 5,782,834 A | 7/1998 | Lucey et al. |
| 5,792,138 A | 8/1998 | Shipp |
| 5,797,941 A | 8/1998 | Schulze et al. |
| 5,800,432 A | 9/1998 | Swanson |
| 5,800,449 A | 9/1998 | Wales |
| 5,807,393 A | 9/1998 | Williamson, IV et al. |
| 5,810,811 A | 9/1998 | Yates et al. |
| 5,817,033 A | 10/1998 | DeSantis et al. |
| 5,817,093 A | 10/1998 | Williamson, IV et al. |
| 5,836,909 A | 11/1998 | Cosmescu |
| 5,836,943 A | 11/1998 | Miller, III |
| 5,853,412 A | 12/1998 | Mayenberger |
| 5,876,401 A | 3/1999 | Schulze et al. |
| 5,880,668 A | 3/1999 | Hall |
| 5,891,142 A | 4/1999 | Eggers et al. |
| 5,906,625 A | 5/1999 | Bito et al. |
| 5,984,938 A | 11/1999 | Yoon |
| 6,003,517 A | 12/1999 | Sheffield et al. |
| 6,013,052 A | 1/2000 | Durman et al. |
| 6,024,741 A | 2/2000 | Williamson, IV et al. |
| 6,024,744 A | 2/2000 | Kese et al. |
| 6,033,399 A | 3/2000 | Gines |
| 6,039,734 A | 3/2000 | Goble |
| 6,050,996 A | 4/2000 | Schmaltz et al. |
| 6,063,098 A | 5/2000 | Houser et al. |
| 6,068,629 A | 5/2000 | Haissaguerre et al. |
| 6,074,389 A | 6/2000 | Levine et al. |

(56) References Cited

U.S. PATENT DOCUMENTS

| | | |
|---|---|---|
| 6,091,995 A | 7/2000 | Ingle et al. |
| 6,099,483 A | 8/2000 | Palmer et al. |
| 6,099,550 A | 8/2000 | Yoon |
| H1904 H | 10/2000 | Yates et al. |
| 6,144,402 A | 11/2000 | Norsworthy et al. |
| 6,152,923 A | 11/2000 | Ryan |
| 6,174,309 B1 | 1/2001 | Wrublewski et al. |
| 6,206,876 B1 | 3/2001 | Levine et al. |
| 6,228,080 B1 | 5/2001 | Gines |
| 6,259,230 B1 | 7/2001 | Chou |
| 6,277,117 B1 | 8/2001 | Tetzlaff et al. |
| 6,292,700 B1 | 9/2001 | Morrison et al. |
| 6,325,799 B1 | 12/2001 | Goble |
| 6,340,878 B1 | 1/2002 | Oglesbee |
| 6,391,026 B1 | 5/2002 | Hung et al. |
| 6,398,779 B1 | 6/2002 | Buysse et al. |
| H2037 H | 7/2002 | Yates et al. |
| 6,419,675 B1 | 7/2002 | Gallo, Sr. |
| 6,430,446 B1 | 8/2002 | Knowlton |
| 6,443,968 B1 | 9/2002 | Holthaus et al. |
| 6,458,128 B1 | 10/2002 | Schulze |
| 6,464,702 B2 | 10/2002 | Schulze et al. |
| 6,491,690 B1 | 12/2002 | Goble et al. |
| 6,500,112 B1 | 12/2002 | Khouri |
| 6,500,176 B1 | 12/2002 | Truckai et al. |
| 6,503,248 B1 | 1/2003 | Levine |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,554,829 B2 | 4/2003 | Schulze et al. |
| 6,558,376 B2 | 5/2003 | Bishop |
| 6,572,639 B1 | 6/2003 | Ingle et al. |
| 6,575,969 B1 | 6/2003 | Rittman, III et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,602,252 B2 | 8/2003 | Mollenauer |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,635,057 B2 | 10/2003 | Harano et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,673,248 B2 | 1/2004 | Chowdhury |
| 6,679,882 B1 | 1/2004 | Kornerup |
| 6,695,840 B2 | 2/2004 | Schulze |
| 6,722,552 B2 | 4/2004 | Fenton, Jr. |
| 6,770,072 B1 | 8/2004 | Truckai et al. |
| 6,773,409 B2 | 8/2004 | Truckai et al. |
| 6,773,435 B2 | 8/2004 | Schulze et al. |
| 6,775,575 B2 | 8/2004 | Bommannan et al. |
| 6,789,939 B2 | 9/2004 | Schrödinger et al. |
| 6,796,981 B2 | 9/2004 | Wham et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,821,273 B2 | 11/2004 | Mollenauer |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,936 B2 | 6/2006 | Ryan |
| 7,070,597 B2 | 7/2006 | Truckai et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,094,235 B2 | 8/2006 | Francischelli et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,112,201 B2 | 9/2006 | Truckai et al. |
| 7,118,570 B2 | 10/2006 | Tetzlaff et al. |
| 7,125,409 B2 | 10/2006 | Truckai et al. |
| 7,131,970 B2 | 11/2006 | Moses et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,160,296 B2 | 1/2007 | Pearson et al. |
| 7,169,146 B2 | 1/2007 | Truckai et al. |
| 7,169,156 B2 | 1/2007 | Hart |
| 7,186,253 B2 | 3/2007 | Truckai et al. |
| 7,189,233 B2 | 3/2007 | Truckai et al. |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,226,448 B2 | 6/2007 | Bertolero et al. |
| 7,232,440 B2 | 6/2007 | Dumbauld et al. |
| 7,235,073 B2 | 6/2007 | Levine et al. |
| 7,241,294 B2 | 7/2007 | Reschke |
| 7,251,531 B2 | 7/2007 | Mosher et al. |
| 7,252,667 B2 | 8/2007 | Moses et al. |
| 7,267,677 B2 | 9/2007 | Johnson et al. |
| 7,267,685 B2 | 9/2007 | Butaric et al. |
| 7,287,682 B1 | 10/2007 | Ezzat et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckal et al. |
| 7,357,287 B2 | 4/2008 | Shelton, IV et al. |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,381,209 B2 | 6/2008 | Truckai et al. |
| 7,384,420 B2 | 6/2008 | Dycus et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,422,139 B2 | 9/2008 | Shelton, IV et al. |
| 7,435,582 B2 | 10/2008 | Zimmermann et al. |
| 7,442,193 B2 | 10/2008 | Shields et al. |
| 7,445,621 B2 | 11/2008 | Dumbauld et al. |
| 7,464,846 B2 | 12/2008 | Shelton, IV et al. |
| 7,473,253 B2 | 1/2009 | Dycus et al. |
| 7,488,319 B2 | 2/2009 | Yates |
| 7,491,201 B2 | 2/2009 | Shields et al. |
| 7,498,080 B2 | 3/2009 | Tung et al. |
| 7,510,107 B2 | 3/2009 | Timm et al. |
| 7,513,025 B2 | 4/2009 | Fischer |
| 7,517,349 B2 | 4/2009 | Truckai et al. |
| 7,540,872 B2 | 6/2009 | Schechter et al. |
| 7,550,216 B2 | 6/2009 | Ofer et al. |
| 7,559,452 B2 | 7/2009 | Wales et al. |
| 7,582,086 B2 | 9/2009 | Privitera et al. |
| 7,586,289 B2 | 9/2009 | Andruk et al. |
| 7,588,176 B2 | 9/2009 | Timm et al. |
| 7,594,925 B2 | 9/2009 | Danek et al. |
| 7,597,693 B2 | 10/2009 | Garrison |
| 7,604,150 B2 | 10/2009 | Boudreaux |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |

(56) References Cited

U.S. PATENT DOCUMENTS

| | | | |
|---|---|---|---|
| 7,641,653 B2 | 1/2010 | Dalla et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,703,459 B2 | 4/2010 | Saadat et al. |
| 7,708,751 B2 | 5/2010 | Hughes et al. |
| 7,722,607 B2 | 5/2010 | Dumbauld et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,766,910 B2 | 8/2010 | Hixson et al. |
| 7,776,037 B2 | 8/2010 | Odom |
| 7,780,663 B2 | 8/2010 | Yates et al. |
| 7,784,663 B2 | 8/2010 | Shelton, IV |
| 7,803,156 B2 | 9/2010 | Eder et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,872 B2 | 10/2010 | Johnson et al. |
| 7,832,408 B2 | 11/2010 | Shelton, IV et al. |
| 7,832,612 B2 | 11/2010 | Baxter, III et al. |
| 7,846,159 B2 | 12/2010 | Morrison et al. |
| 7,846,160 B2 | 12/2010 | Payne et al. |
| 7,879,035 B2 | 2/2011 | Garrison et al. |
| 7,879,070 B2 | 2/2011 | Ortiz et al. |
| 7,901,400 B2 | 3/2011 | Wham et al. |
| 7,931,649 B2 | 4/2011 | Couture et al. |
| 7,935,114 B2 | 5/2011 | Takashino et al. |
| 7,955,331 B2 | 6/2011 | Truckai et al. |
| 7,963,963 B2 | 6/2011 | Francischelli et al. |
| 7,967,602 B2 | 6/2011 | Lindquist |
| 7,981,113 B2 | 7/2011 | Truckai et al. |
| 7,997,278 B2 | 8/2011 | Utley et al. |
| 8,020,743 B2 | 9/2011 | Shelton, IV |
| 8,058,771 B2 | 11/2011 | Giordano et al. |
| 8,070,036 B1 | 12/2011 | Knodel et al. |
| 8,105,323 B2 | 1/2012 | Buysse et al. |
| 8,128,624 B2 | 3/2012 | Couture et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,197,472 B2 | 6/2012 | Lau et al. |
| 8,197,479 B2 | 6/2012 | Olson et al. |
| 8,221,415 B2 | 7/2012 | Francischelli |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,262,563 B2 | 9/2012 | Bakos et al. |
| 8,277,446 B2 | 10/2012 | Heard |
| 8,277,447 B2 | 10/2012 | Garrison et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,298,232 B2 | 10/2012 | Unger |
| 8,303,583 B2 | 11/2012 | Hosier et al. |
| 8,323,310 B2 | 12/2012 | Kingsley |
| 8,377,059 B2 | 2/2013 | Deville et al. |
| 8,397,971 B2 | 3/2013 | Yates et al. |
| 8,414,577 B2 | 4/2013 | Boudreaux et al. |
| 8,430,876 B2 | 4/2013 | Kappus et al. |
| 8,453,906 B2 | 6/2013 | Huang et al. |
| 8,460,288 B2 | 6/2013 | Tamai et al. |
| 8,460,292 B2 | 6/2013 | Truckai et al. |
| 8,486,057 B2 | 7/2013 | Behnke, II |
| 8,496,682 B2 | 7/2013 | Guerra et al. |
| 8,535,311 B2 | 9/2013 | Schall |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,231 B2 | 11/2013 | Boudreaux et al. |
| 8,591,506 B2 | 11/2013 | Wham et al. |
| 8,613,383 B2 | 12/2013 | Beckman et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,647,350 B2 | 2/2014 | Mohan et al. |
| 8,663,222 B2 | 3/2014 | Anderson et al. |
| 8,685,020 B2 | 4/2014 | Weizman et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,734,443 B2 | 5/2014 | Hixson et al. |
| 8,747,404 B2 | 6/2014 | Boudreaux et al. |
| 8,753,338 B2 | 6/2014 | Widenhouse et al. |
| 8,764,747 B2 | 7/2014 | Cummings et al. |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,834,466 B2 | 9/2014 | Cummings et al. |
| 8,834,518 B2 | 9/2014 | Faller et al. |
| 8,888,776 B2 | 11/2014 | Dietz et al. |
| 8,906,016 B2 | 12/2014 | Boudreaux et al. |
| 8,926,607 B2 | 1/2015 | Norvell et al. |
| 8,926,608 B2 | 1/2015 | Bacher et al. |
| 8,939,974 B2 | 1/2015 | Boudreaux et al. |
| 8,951,248 B2 | 2/2015 | Messerly et al. |
| 8,956,349 B2 | 2/2015 | Aldridge et al. |
| 8,979,843 B2 | 3/2015 | Timm et al. |
| 8,979,844 B2 | 3/2015 | White et al. |
| 8,986,302 B2 | 3/2015 | Aldridge et al. |
| 9,005,199 B2 | 4/2015 | Beckman et al. |
| 9,011,437 B2 | 4/2015 | Woodruff et al. |
| 9,044,243 B2 | 6/2015 | Johnson et al. |
| 2002/0022836 A1 | 2/2002 | Goble et al. |
| 2002/0165541 A1 | 11/2002 | Whitman |
| 2003/0014053 A1 | 1/2003 | Nguyen et al. |
| 2003/0105474 A1 | 6/2003 | Bonutti |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0216722 A1 | 11/2003 | Swanson |
| 2003/0229344 A1 | 12/2003 | Dycus et al. |
| 2004/0019350 A1 | 1/2004 | O'Brien et al. |
| 2004/0092992 A1 | 5/2004 | Adams et al. |
| 2004/0138621 A1 | 7/2004 | Jahns et al. |
| 2004/0167508 A1 | 8/2004 | Wham et al. |
| 2004/0193150 A1 | 9/2004 | Sharkey et al. |
| 2004/0232196 A1 | 11/2004 | Shelton, IV et al. |
| 2004/0249374 A1 | 12/2004 | Tetzlaff et al. |
| 2004/0260273 A1 | 12/2004 | Wan |
| 2005/0015125 A1 | 1/2005 | Mioduski et al. |
| 2005/0033278 A1 | 2/2005 | McClurken et al. |
| 2005/0085809 A1 | 4/2005 | Mucko et al. |
| 2005/0090817 A1 | 4/2005 | Phan |
| 2005/0101991 A1* | 5/2005 | Ahlberg et al. ............... 606/205 |
| 2005/0165429 A1 | 7/2005 | Douglas et al. |
| 2005/0171522 A1 | 8/2005 | Christopherson |
| 2005/0203507 A1 | 9/2005 | Truckai et al. |
| 2005/0261581 A1 | 11/2005 | Hughes et al. |
| 2005/0267464 A1 | 12/2005 | Truckai et al. |
| 2006/0052777 A1* | 3/2006 | Dumbauld ....................... 606/51 |
| 2006/0052778 A1 | 3/2006 | Chapman et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0270916 A1 | 11/2006 | Skwarek et al. |
| 2006/0293656 A1 | 12/2006 | Shadduck et al. |
| 2007/0027469 A1 | 2/2007 | Smith et al. |
| 2007/0073185 A1 | 3/2007 | Nakao |
| 2007/0073341 A1 | 3/2007 | Smith et al. |
| 2007/0106158 A1 | 5/2007 | Madan et al. |
| 2007/0146113 A1 | 6/2007 | Truckai et al. |
| 2007/0173803 A1 | 7/2007 | Wham et al. |
| 2007/0173813 A1 | 7/2007 | Odom |

(56) References Cited

U.S. PATENT DOCUMENTS

| | | |
|---|---|---|
| 2007/0185474 A1 | 8/2007 | Nahen |
| 2007/0191713 A1 | 8/2007 | Eichmann et al. |
| 2007/0191830 A1 | 8/2007 | Crompton, Jr. et al. |
| 2007/0203483 A1 | 8/2007 | Kim et al. |
| 2007/0208312 A1 | 9/2007 | Norton et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0236213 A1 | 10/2007 | Paden et al. |
| 2007/0239025 A1 | 10/2007 | Wiener et al. |
| 2007/0260242 A1 | 11/2007 | Dycus et al. |
| 2007/0265613 A1 | 11/2007 | Edelstein et al. |
| 2008/0015575 A1 | 1/2008 | Odom et al. |
| 2008/0071269 A1 | 3/2008 | Hilario et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0167522 A1 | 7/2008 | Giordano et al. |
| 2008/0188755 A1 | 8/2008 | Hart |
| 2008/0188851 A1 | 8/2008 | Truckai et al. |
| 2008/0188912 A1 | 8/2008 | Stone et al. |
| 2008/0221565 A1 | 9/2008 | Eder et al. |
| 2008/0262491 A1 | 10/2008 | Swoyer et al. |
| 2008/0269862 A1 | 10/2008 | Elmouelhi et al. |
| 2008/0281315 A1 | 11/2008 | Gines |
| 2008/0294158 A1 | 11/2008 | Pappone et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0099582 A1 | 4/2009 | Isaacs et al. |
| 2009/0125026 A1 | 5/2009 | Rioux et al. |
| 2009/0125027 A1 | 5/2009 | Fischer |
| 2009/0138003 A1 | 5/2009 | Deville et al. |
| 2009/0138006 A1 | 5/2009 | Bales et al. |
| 2009/0182332 A1 | 7/2009 | Long et al. |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0248021 A1 | 10/2009 | McKenna |
| 2009/0320268 A1 | 12/2009 | Cunningham et al. |
| 2009/0326530 A1 | 12/2009 | Orban, III et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0076433 A1 | 3/2010 | Taylor et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0168620 A1 | 7/2010 | Klimovitch et al. |
| 2010/0222752 A1 | 9/2010 | Collins, Jr. et al. |
| 2010/0237132 A1 | 9/2010 | Measamer et al. |
| 2010/0264194 A1 | 10/2010 | Huang et al. |
| 2010/0274278 A1 | 10/2010 | Fleenor et al. |
| 2011/0015627 A1 | 1/2011 | DiNardo et al. |
| 2011/0082486 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087220 A1 | 4/2011 | Felder et al. |
| 2011/0155781 A1 | 6/2011 | Swensgard et al. |
| 2011/0224668 A1 | 9/2011 | Johnson et al. |
| 2011/0276049 A1 | 11/2011 | Gerhardt |
| 2011/0276057 A1 | 11/2011 | Conlon et al. |
| 2011/0301605 A1 | 12/2011 | Horner |
| 2011/0306967 A1 | 12/2011 | Payne et al. |
| 2012/0010616 A1* | 1/2012 | Huang et al. .......... 606/52 |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022527 A1 | 1/2012 | Woodruff et al. |
| 2012/0078247 A1 | 3/2012 | Worrell et al. |
| 2012/0078248 A1* | 3/2012 | Worrell et al. .......... 606/45 |
| 2012/0083783 A1 | 4/2012 | Davison et al. |
| 2012/0109186 A1* | 5/2012 | Parrott et al. .......... 606/206 |
| 2012/0116379 A1* | 5/2012 | Yates et al. .......... 606/33 |
| 2012/0116391 A1 | 5/2012 | Houser et al. |
| 2012/0130256 A1 | 5/2012 | Buysse et al. |
| 2012/0136353 A1 | 5/2012 | Romero |
| 2012/0150170 A1 | 6/2012 | Buysse et al. |
| 2012/0172859 A1 | 7/2012 | Condie et al. |
| 2012/0265196 A1 | 10/2012 | Turner et al. |
| 2013/0023875 A1 | 1/2013 | Harris et al. |
| 2013/0023925 A1 | 1/2013 | Mueller |
| 2013/0030433 A1 | 1/2013 | Heard |
| 2013/0079762 A1 | 3/2013 | Twomey et al. |
| 2013/0085496 A1 | 4/2013 | Unger et al. |
| 2013/0103023 A1 | 4/2013 | Monson et al. |
| 2013/0103024 A1 | 4/2013 | Monson et al. |
| 2013/0123776 A1 | 5/2013 | Monson et al. |
| 2013/0123777 A1 | 5/2013 | Monson et al. |
| 2013/0123782 A1 | 5/2013 | Trees et al. |
| 2013/0131660 A1 | 5/2013 | Monson et al. |
| 2013/0253502 A1 | 9/2013 | Aronow et al. |
| 2013/0338661 A1 | 12/2013 | Behnke, II |
| 2014/0005680 A1 | 1/2014 | Shelton, IV et al. |
| 2014/0094801 A1 | 4/2014 | Boudreaux et al. |
| 2014/0148806 A1 | 5/2014 | Witt et al. |
| 2014/0194914 A1 | 7/2014 | Hunt et al. |
| 2014/0194915 A1 | 7/2014 | Johnson et al. |
| 2014/0257284 A1 | 9/2014 | Artale |
| 2014/0330271 A1 | 11/2014 | Dietz et al. |
| 2014/0343550 A1 | 11/2014 | Faller et al. |
| 2015/0018826 A1 | 1/2015 | Boudreaux |
| 2015/0080876 A1 | 3/2015 | Worrell et al. |
| 2015/0080879 A1 | 3/2015 | Trees et al. |
| 2015/0080891 A1 | 3/2015 | Shelton, IV et al. |
| 2015/0133915 A1 | 5/2015 | Strobl et al. |
| 2015/0133921 A1 | 5/2015 | Strobl et al. |
| 2015/0190189 A1 | 7/2015 | Yates et al. |
| 2015/0196352 A1 | 7/2015 | Beckman et al. |
| 2015/0201953 A1 | 7/2015 | Strobl et al. |
| 2015/0230853 A1 | 8/2015 | Johnson et al. |
| 2015/0265347 A1 | 9/2015 | Yates et al. |

FOREIGN PATENT DOCUMENTS

| | | |
|---|---|---|
| EP | 0630612 A1 | 12/1994 |
| EP | 0705571 A1 | 4/1996 |
| EP | 0557806 B1 | 5/1998 |
| EP | 0640317 B1 | 9/1999 |
| EP | 0722696 B1 | 12/2002 |
| EP | 1293172 B1 | 4/2006 |
| EP | 1749479 A1 | 2/2007 |
| EP | 1767157 A1 | 3/2007 |
| EP | 1878399 A1 | 1/2008 |
| EP | 1915953 A1 | 4/2008 |
| EP | 1532933 B1 | 5/2008 |
| EP | 1707143 B1 | 6/2008 |
| EP | 1943957 A2 | 7/2008 |
| EP | 1849424 B1 | 4/2009 |
| EP | 2042117 A1 | 4/2009 |
| EP | 2060238 A1 | 5/2009 |
| EP | 1810625 B1 | 8/2009 |
| EP | 2090238 A1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1728475 B1 | 8/2011 |
| EP | 2353518 A1 | 8/2011 |
| EP | 2508143 B1 | 2/2014 |
| GB | 2472216 A | 2/2011 |

(56) References Cited

FOREIGN PATENT DOCUMENTS

| | | |
|---|---|---|
| JP | H08-229050 A | 9/1996 |
| JP | 2008-018226 A | 1/2008 |
| WO | WO 81/03272 A1 | 11/1981 |
| WO | WO 93/07817 | 4/1993 |
| WO | WO 93/22973 A1 | 11/1993 |
| WO | WO 95/10978 A1 | 4/1995 |
| WO | WO 96/35382 A1 | 11/1996 |
| WO | WO 97/10764 A1 | 3/1997 |
| WO | WO 98/00069 A1 | 1/1998 |
| WO | WO 98/40020 A1 | 9/1998 |
| WO | WO 98/57588 A1 | 12/1998 |
| WO | WO 99/23960 A1 | 5/1999 |
| WO | WO 99/40861 A1 | 8/1999 |
| WO | WO 00/24330 A1 | 5/2000 |
| WO | WO 00/24331 A1 | 5/2000 |
| WO | WO 00/25691 A1 | 5/2000 |
| WO | WO 01/28444 A1 | 4/2001 |
| WO | WO 02/080797 A1 | 10/2002 |
| WO | WO 03/001986 A2 | 1/2003 |
| WO | WO 03/013374 A1 | 2/2003 |
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2004/078051 A2 | 9/2004 |
| WO | WO 2005/052959 A2 | 6/2005 |
| WO | WO 2006/021269 A1 | 3/2006 |
| WO | WO 2006/036706 A1 | 4/2006 |
| WO | WO 2006/055166 A2 | 5/2006 |
| WO | WO 2008/020964 A2 | 2/2008 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/039179 A1 | 3/2009 |
| WO | WO 2009/059741 A1 | 5/2009 |
| WO | WO 2009/082477 A2 | 7/2009 |
| WO | WO 2009/149234 A1 | 12/2009 |
| WO | WO 2010/017266 A1 | 2/2010 |
| WO | WO 2010/104755 A1 | 9/2010 |
| WO | WO 2011/084768 A1 | 7/2011 |
| WO | WO 2011/089717 A1 | 7/2011 |
| WO | WO 2011/144911 A1 | 11/2011 |
| WO | WO 2013/034629 A1 | 3/2013 |
| WO | WO 2013/062978 A2 | 5/2013 |
| WO | WO 2013/154157 A1 | 10/2013 |

OTHER PUBLICATIONS

Written Opinion for PCT/US2014/052100, Mar. 11, 2015 (9 pages).
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Hörmann et al., "Reversible and irreversible denaturation of collagen fibers." Biochemistry, 10, pp. 932-937 (1971).
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-induced changes in the mechanics of a collagenous tissue: pseudoelastic behavior at 37° C," Journal of Biomechanics, 31, pp. 211-216 (1998).
Chen et al., "Heat-Induced Changes in the Mechanics of a Collagenous Tissue: Isothermal Free Shrinkage," Transactions of the Asme, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=Ml&sp=1 . . ., accessed Aug. 25, 2009.
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dlmrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
Kurt Gieck & Reiner Gieck, Engineering Formulas § Z.7 (7th ed. 1997).
National Semiconductors Temperature Sensor Handbook—http://www.national.com/appinfo/tempsensors/files/temphb.pdf; accessed online: Apr. 1, 2011.
Wright, et al., "Time-Temperature Equivalence of Heat-Induced Changes in Cells and Proteins," Feb., 1998. ASME Journal of Biomechanical Engineering, vol. 120, pp. 22-26.
Covidien Brochure, [Value Analysis Brief], LigaSure Advance™ Pistol Grip, dated Rev. Apr. 2010 (7 pages).
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Covidien Brochure, The LigaSure Precise™ Instrument, dated Mar. 2011 (2 pages).
Erbe Electrosurgery VIO® 200 S, (2012), p. 7, 12 pages, accessed Mar. 31, 2014 at http://www.erbe-med.com/erbe/media/Marketingmaterialien/85140-170_ERBE_EN_VIO_200_S D027541.
Jang, J. et al. "Neuro-fuzzy and Soft Computing." Prentice Hall, 1997, pp. 13-89, 199-293, 335-393, 453-496, 535-549.
Douglas, S.C. "Introduction to Adaptive Filter". Digital Signal Processing Handbook. Ed. Vijay K. Madisetti and Douglas B. Williams. Boca Raton: CRC Press LLC, 1999.
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.

* cited by examiner

SURGICAL DEVICES WITH CLOSE QUARTER ARTICULATION FEATURES

BACKGROUND

The present disclosure is related generally to close quarter articulation features for surgical devices. More particularly, the present disclosure is related to surgical devices having an up and down (vertical) articulation mode.

A variety of surgical instruments include a tissue cutting element and one or more elements that transmit RF energy to tissue (e.g., to coagulate or seal the tissue). An example of such a device is the ENSEAL® Tissue Sealing Device by Ethicon Endo-Surgery, Inc., of Cincinnati, Ohio.

In addition, a variety of surgical instruments include a shaft having an articulation section, providing enhanced positioning capabilities for an end effector that is located distal to the articulation section of the shaft. Examples of such devices include various models of the ENDOPATH® Endocutters by Ethicon Endo-Surgery, Inc., of Cincinnati, Ohio.

While several devices have been made and used, it is believed that no one prior to the inventors has made or used the device described in the appended claims.

SUMMARY

In one embodiment, an apparatus comprises a shaft section extending longitudinally along a first plane; an end effector comprising a first jaw and a second jaw configured to pivotally open and close in a second plane relative to the first plane about a pivot point, wherein the first plane is orthogonal to the second plane; and an articulation section disposed between the shaft section and the end effector, the articulation section configured to articulate in the second plane relative to the first plane in response to a rotatable articulation control mechanism. At least one of the first and second jaws comprises an electrode.

In another embodiment, an apparatus comprises a shaft section extending longitudinally along a first plane; an end effector comprising a first jaw and a second jaw configured to pivotally open and close in a second plane relative to the first plane about a pivot point, wherein the first plane is orthogonal to the second plane; and an articulation section disposed between the shaft section and the end effector, the articulation section configured to articulate in the second plane relative to the first plane in response to a lost motion mechanism operatively coupled to a trigger mechanism. At least one of the first and second jaws comprises an electrode.

In yet another embodiment, an apparatus comprises an end effector comprising a first jaw and a second jaw configured to pivotally open and close in a first plane relative to a second plane defined by the longitudinally extending shaft section, wherein the first plane is orthogonal to the second plane, the first and second jaws comprising contoured outer edges and a cam slot defined in each of the first and second jaws, the cam slots configured to receive a pivot pin therethrough about which the first and second jaws open and close about a pivot point; and a rigid outer cam tube extending longitudinally, the rigid outer cam tube configured to act upon the contoured outer edges of the first and second jaws; wherein the end effector is configured to articulate in the first plane relative to the second plane in response to the cam tube slidably moving in a longitudinal direction.

In yet another embodiment, an apparatus comprises an end effector comprising a first jaw and a second jaw configured to pivotally open and close in a plane relative to a longitudinal axis, the first and second jaws comprising contoured outer edges and an aperture defined in each of the first and second jaws, the apertures configured to receive a pivot pin therethrough about which the first and second jaws open and close about a pivot point; a rigid outer tube, a distal end of the rigid outer tube pivotally coupled to proximal ends of the first and second jaws; and a drive and chase link arrangement; wherein the end effector is configured to articulate in the plane relative to the longitudinal axis in response to the cam tube slidably moving in a longitudinal direction. The end effector articulates about the pivot point.

In yet another embodiment, an apparatus comprises an end effector comprising a first jaw and a second jaw configured to pivotally open and close in a plane relative to a longitudinal axis about a pivot point, the first and second jaws each define a hub to receive first and second axles therethrough about which the first and second jaws pivotally open and close; an outer tube rotatable about the longitudinal axis; and an inner tube disposed within the outer tube, the inner tube rotatable about the longitudinal axis; wherein the outer tube is rotatably coupled to the first jaw and the inner tube is rotatably coupled to the second jaw; and wherein the end effector is configured to articulate in the plane relative to the longitudinal axis ins response to rotation of the inner or outer tubes about the longitudinal axis. The end effector articulates about the pivot point.

In addition to the foregoing, various other method and/or system and/or program product aspects are set forth and described in the teachings such as text (e.g., claims and/or detailed description) and/or drawings of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

In one or more various aspects, related systems include but are not limited to circuitry and/or programming for effecting herein-referenced method aspects; the circuitry and/or programming can be virtually any combination of hardware, software, and/or firmware configured to effect the herein-referenced method aspects depending upon the design choices of the system designer. In addition to the foregoing, various other method and/or system aspects are set forth and described in the teachings such as text (e.g., claims and/or detailed description) and/or drawings of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

FIGURES

The novel features of the embodiments described herein are set forth with particularity in the appended claims. The embodiments, however, both as to organization and methods of operation may be better understood by reference to the following description, taken in conjunction with the accompanying drawings as follows:

FIG. 1 depicts a side elevational view of an articulatable electrosurgical device showing up and down (vertical plane) articulation of an end effector rather than left to right (horizontal plane) articulation of the end effector in response to a control mechanism for activating the articulation movements, according to one embodiment.

FIG. 2 depicts a side elevational view of the articulatable electrosurgical device of FIG. 1 showing the end effector of the device articulated in an up position and a clamp jaw member clamped from an open position to a closed position in response to a trigger member being squeezed, according to one embodiment.

FIG. 3 depicts a perspective view of the articulatable electrosurgical device of FIG. 1 showing up and down (vertical plane) articulation of an end effector rather than left to right (horizontal plane) articulation of the end effector in response to a rotatable control mechanism for activating the articulation movements, according to one embodiment.

FIG. 4 depicts a side elevational view of an articulatable electrosurgical device showing up and down (vertical plane) articulation of an end effector rather than left to right (horizontal plane) articulation of the end effector in response to a rotatable control mechanism for activating the articulation movements, according to one embodiment.

FIG. 5 depicts a perspective view of the end effector of the device of FIG. 1, in an open configuration.

FIG. 6 depicts another perspective view of the end effector of the device of FIG. 1, in an open configuration.

FIG. 7 depicts a cross-sectional end view of the end effector of FIG. 6, in a closed configuration and with the blade in a distal position.

FIG. 8 depicts a perspective view of an articulation section for the shaft of the device of FIG. 1.

FIG. 9 depicts a cross-sectional end view of the articulation section of FIG. 8, taken along line 9-9 of FIG. 8 for a device having independent articulation and end effector actuator control mechanisms.

FIG. 10 depicts a cross-sectional end view of an articulation section for an electrosurgical device with simultaneous firing and jaw actuation control.

FIG. 11 depicts a top perspective view of another example articulation section for the shaft of the device of FIG. 1.

FIG. 12 depicts a bottom perspective view of another the articulation section of FIG. 11.

FIG. 13 depicts a top plan view of the articulation section of FIG. 11.

FIG. 14 depicts a cross-sectional end view of the articulation section of FIG. 11, taken along line 14-14 of FIG. 11 for a device having independent articulation and end effector actuator control mechanisms.

FIG. 15 depicts a cross-sectional end view of another articulation section for a device having simultaneous articulation and end effector actuator control mechanism.

FIG. 16 depicts a perspective view of another example of articulation and end effector sections for the shaft of the device of FIG. 1.

FIG. 17 depicts articulation and end effector sections of the device shown in FIGS. 8 and 9.

Figure 8:
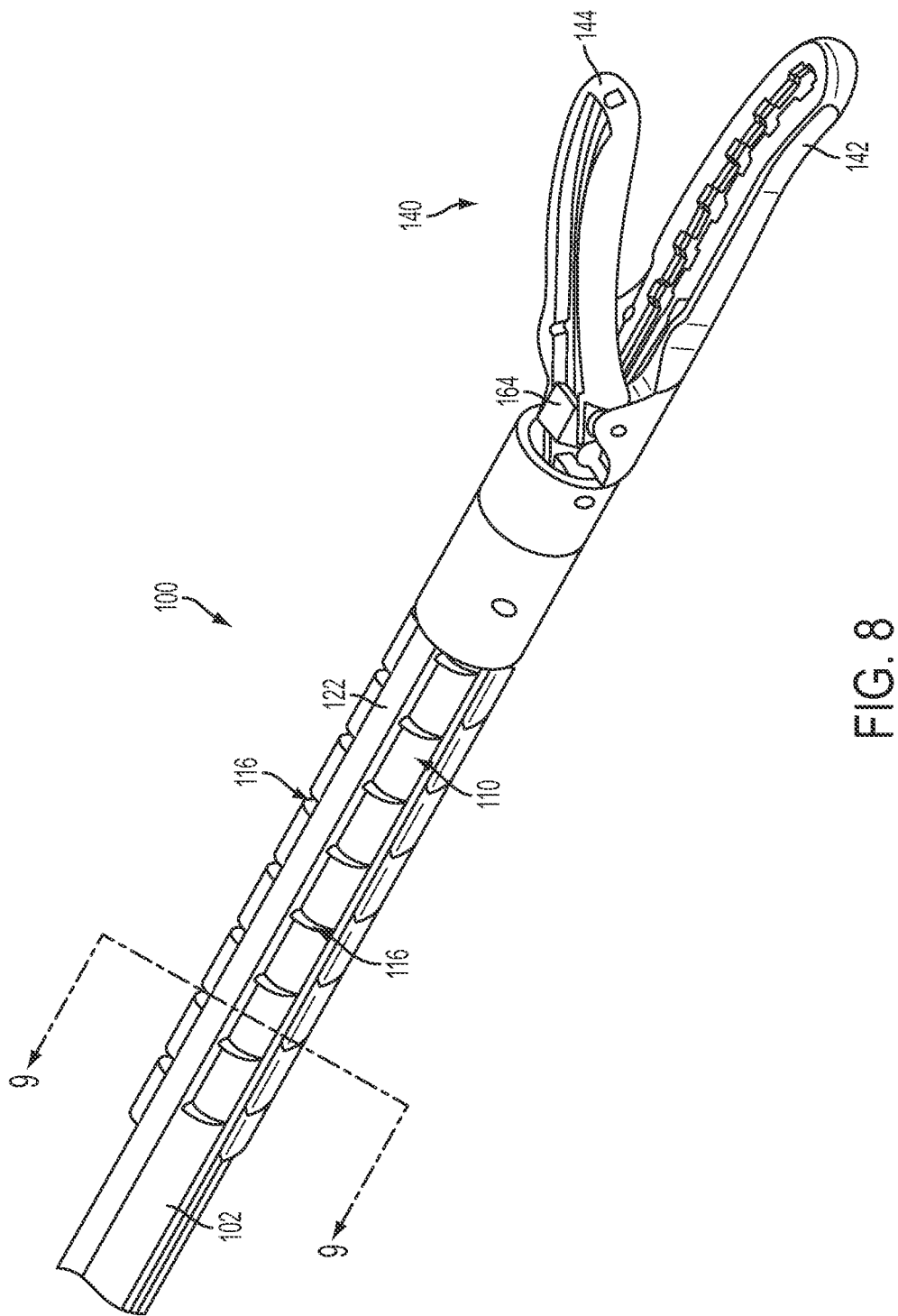
Figure 9:
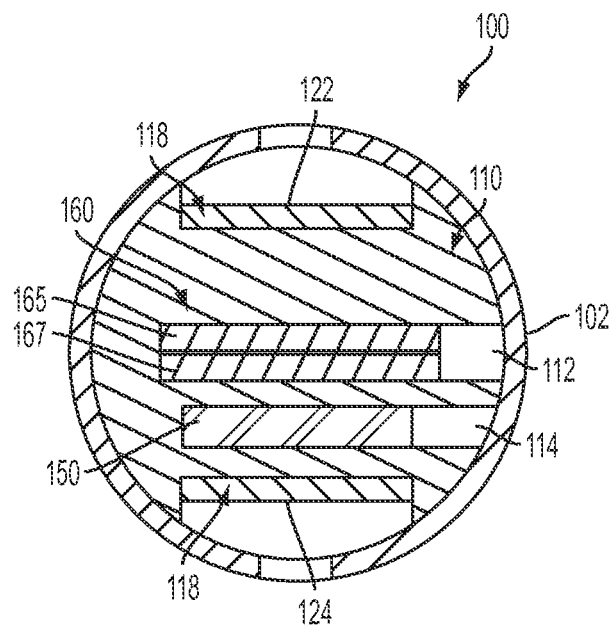
Figure 17:
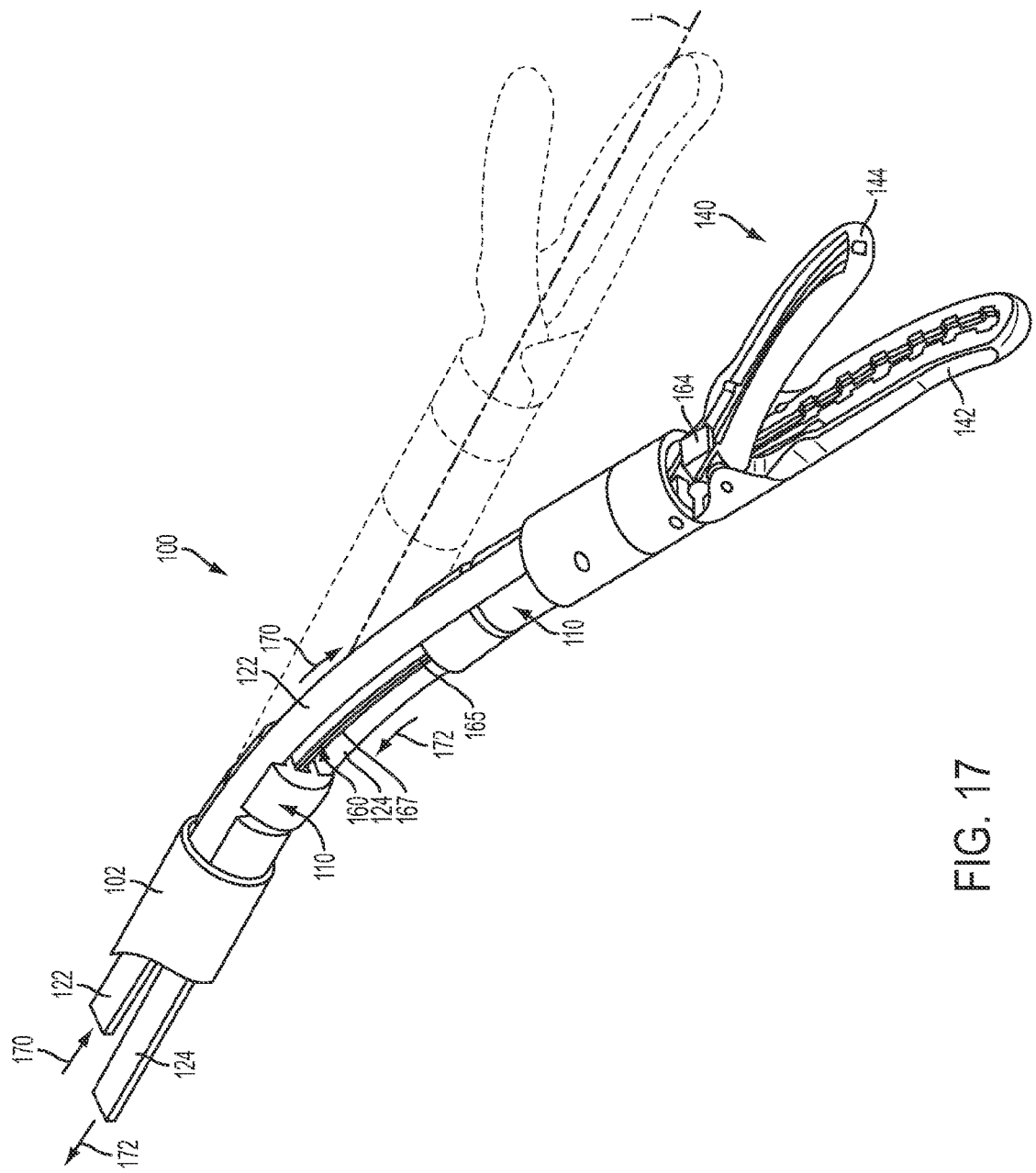
Figure 18:
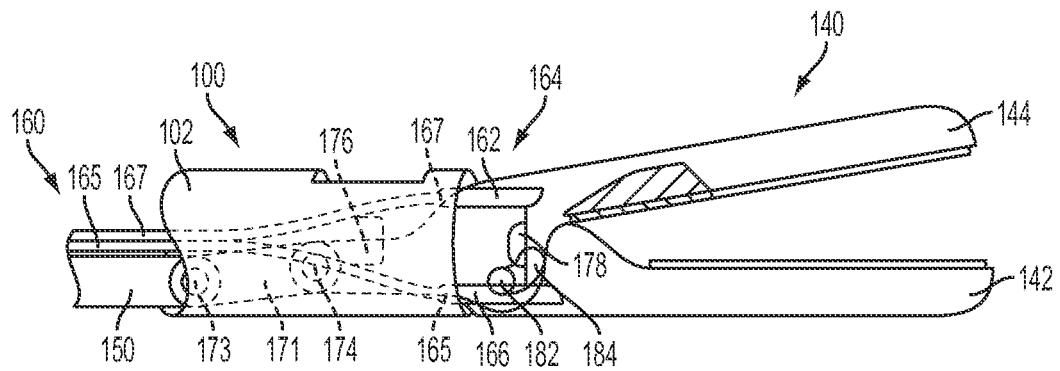
Figure 19:
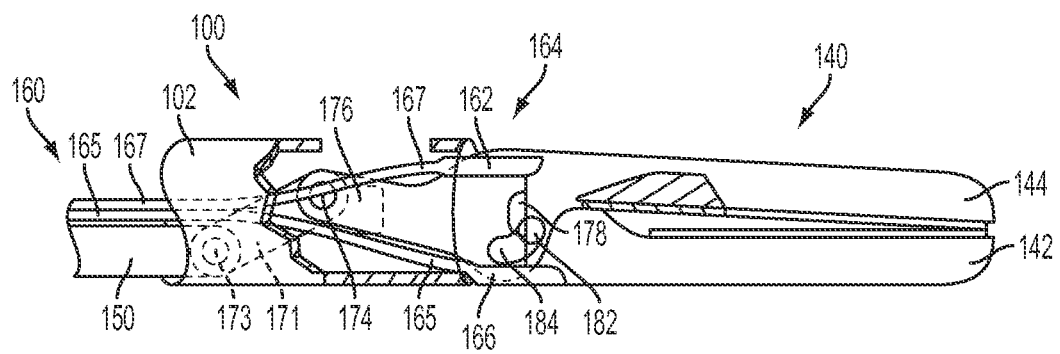
Figure 20:
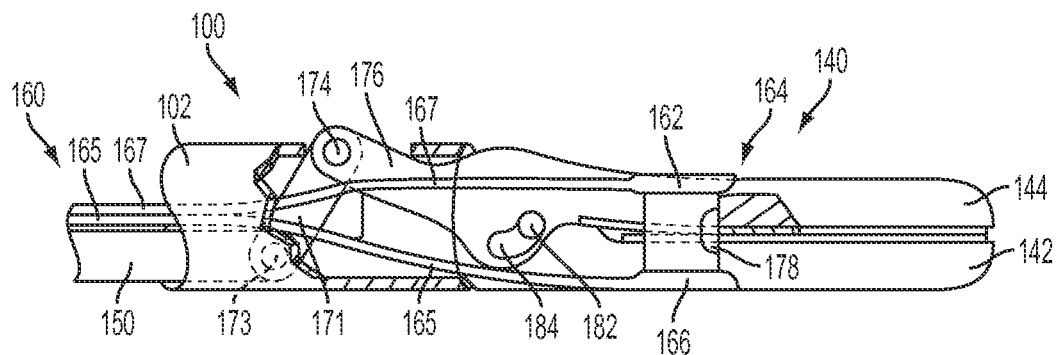

FIGS. 18-20 depict cross-sectional views of the articulation section and end effector shown in FIGS. 8, 9, and 17 with independent articulation and end effector actuator control and a linkage to provide mechanical advantage, where FIG. 18 depicts the end effector jaws in an open position prior to deploying a cutting blade, FIG. 19 depicts the end effector jaws in a closed position prior to deploying the cutting blade, and FIG. 20 depicts the end effector jaws in a closed position as the cutting blade is being deployed.

Figure 21:
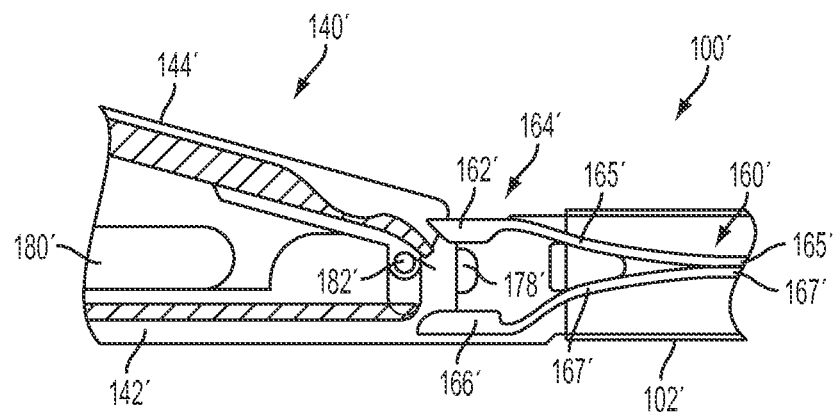
Figure 22:
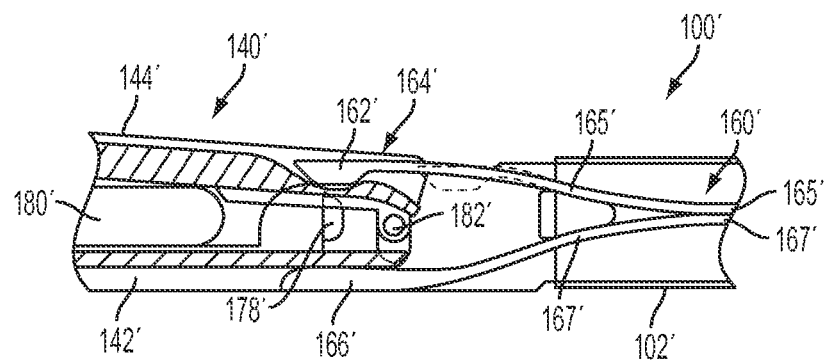
Figure 23:
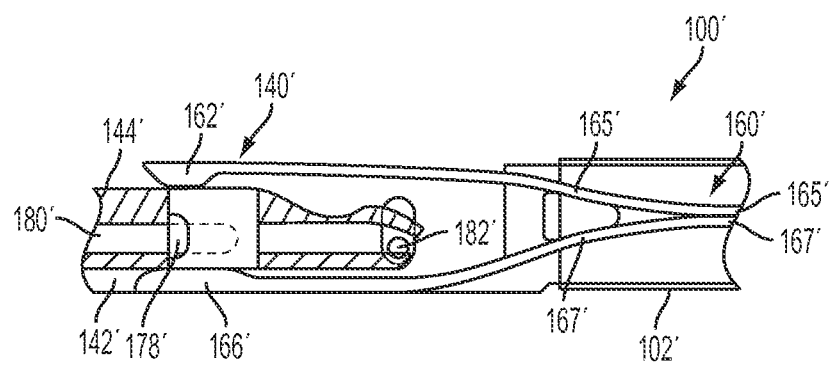

FIGS. 21-23 depict cross-sectional views of articulation section and end effector with a simultaneous articulation and end effector actuator control mechanisms and a linkage to provide mechanical advantage, where FIG. 21 depicts the end effector jaws in an open position prior to deploying the cutting blade, FIG. 22 depicts the end effector jaws in a partially closed position and partially deployed cutting blade, and FIG. 23 depicts the end effector jaws in a closed position as the cutting blade is being deployed.

Figure 25:
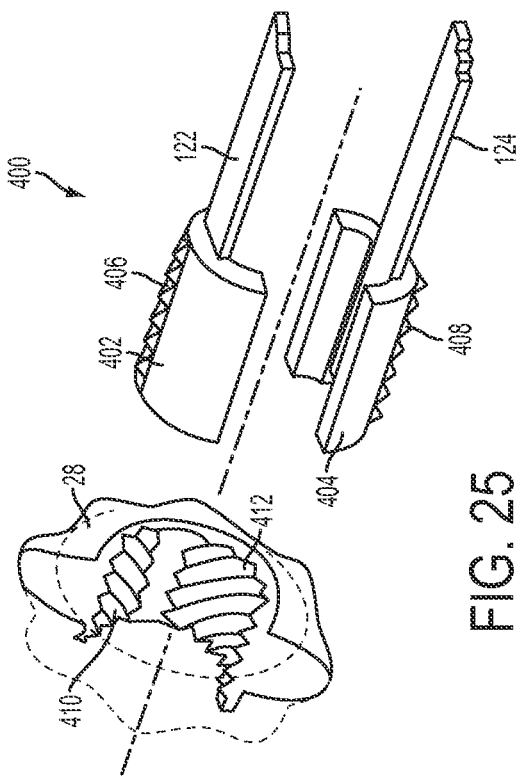
Figure 24:
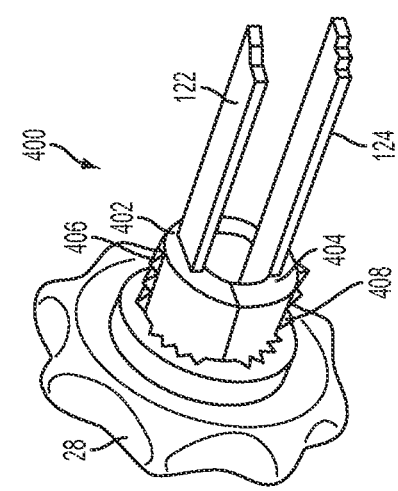
Figure 27:
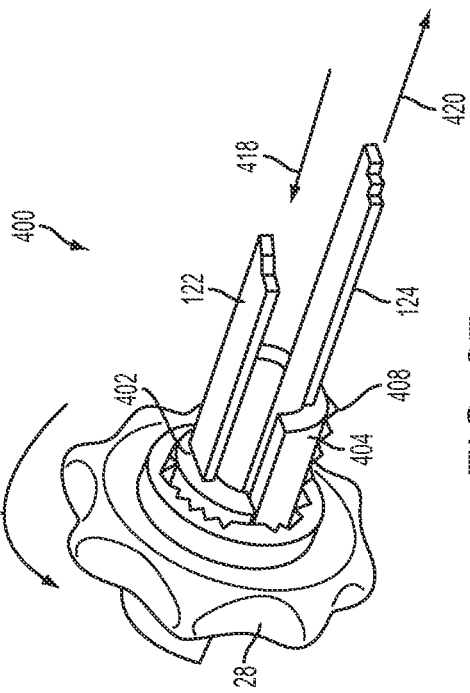
Figure 26:
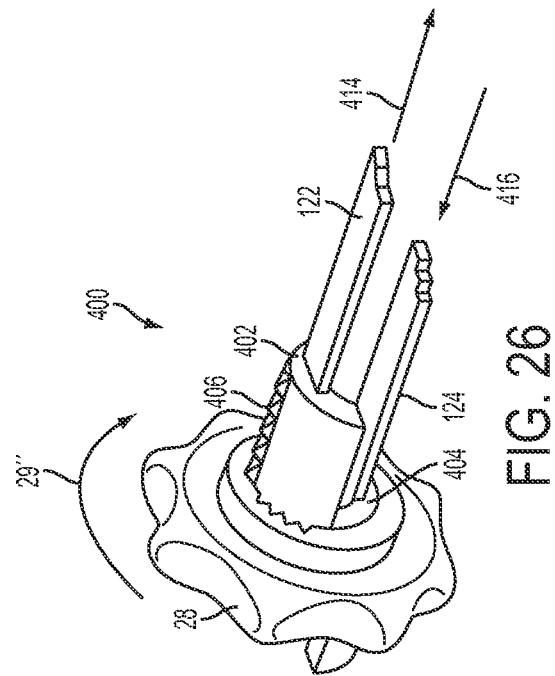

FIGS. 24-27 depict a rotatable articulation control mechanism for activating longitudinal articulation movements according to one embodiment, where FIG. 24 shows one embodiment of a rotatable articulation control mechanism for controlling the vertical articulation of the articulation section, FIG. 25 is an exploded partial cut-away view of the rotatable articulation control mechanism shown in FIG. 24, FIG. 26 shows the rotatable articulation control mechanism rotating in a counterclockwise direction relative to a user and the corresponding longitudinal motion of the articulation bands, FIG. 27 shows the rotatable articulation control mechanism rotating in a clockwise direction relative to a user and the corresponding longitudinal motion of the articulation bands.

FIGS. 28-30A-C depict a lost motion mechanism in a handpiece portion of an electrosurgical device that enables an initial trigger stroke to actuate a closure linkage to clamp the jaws of an end effector and then a remainder of the stroke throws a cutting blade portion while maintaining the jaws clamped.

FIGS. 31A-C and 32-A-E depict alternative articulation mechanisms for the electrosurgical devices previously discussed in connection with FIGS. 1-30, where jaw closure and articulation are on the same pivot.

Figure 30A:
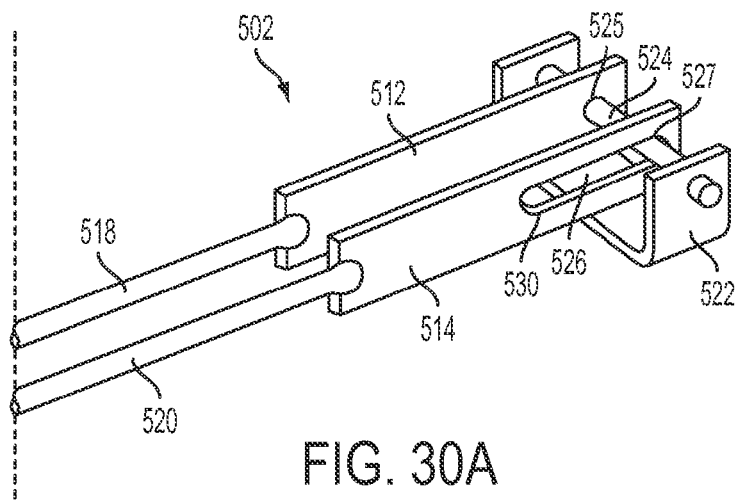
Figure 30B:
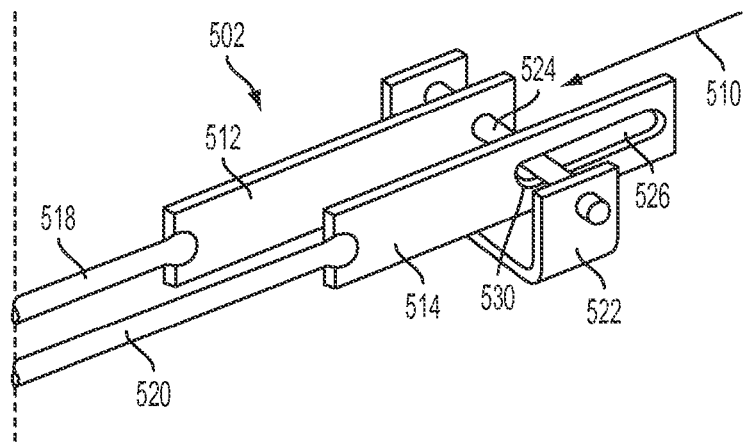
Figure 30C:
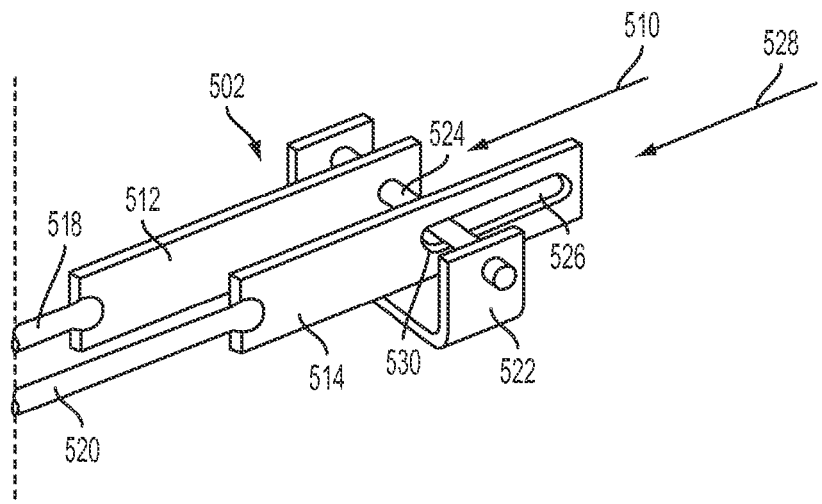
Figure 31A:
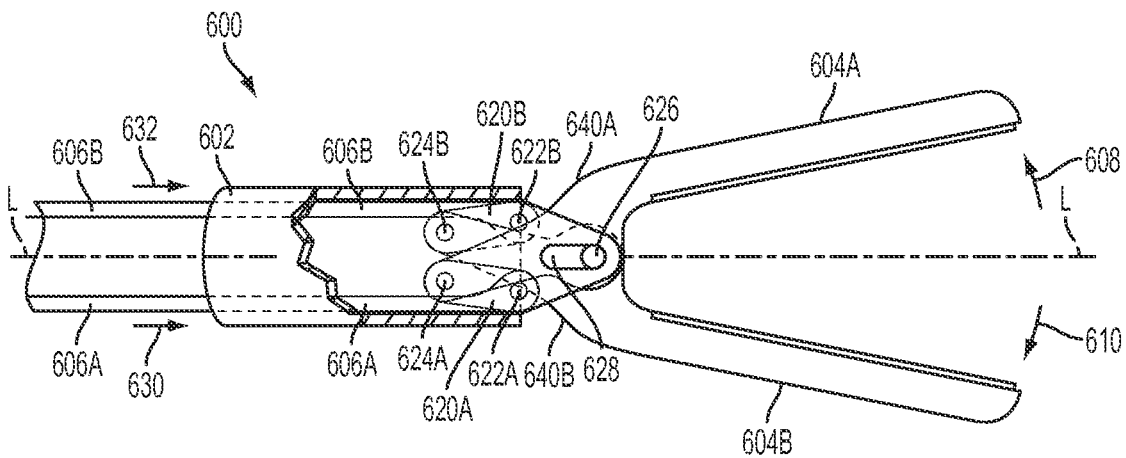
Figure 31B:
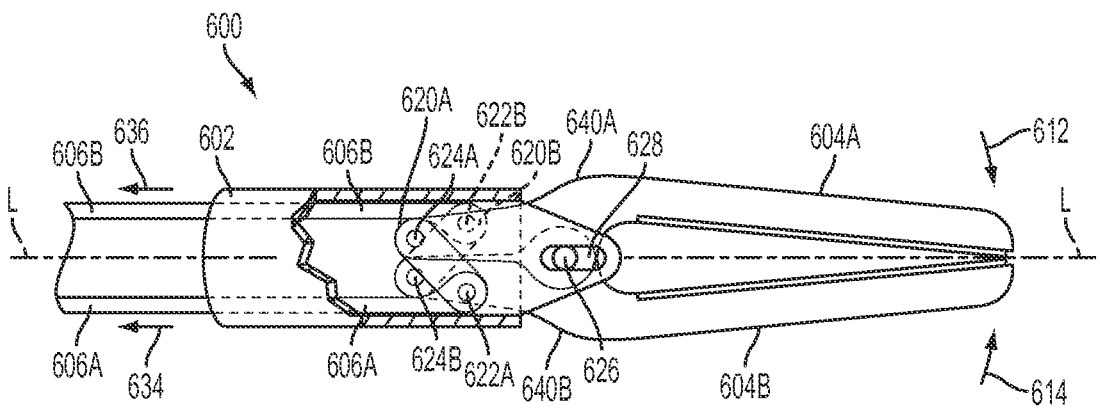
Figure 31C:
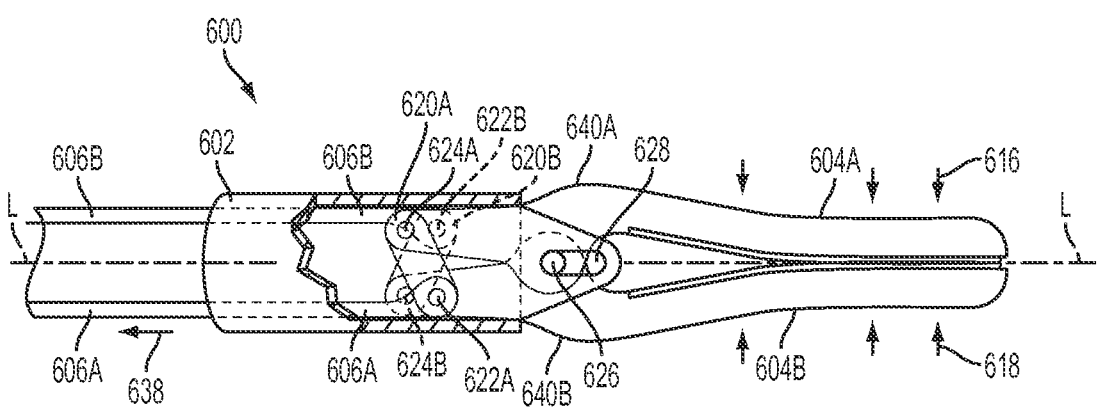

FIGS. 31A-C depict alternative articulation mechanisms for the electrosurgical devices previously discussed in connection with FIGS. 1-30, where jaw closure and articulation are on the same pivot.

FIGS. 32A-E depict alternative articulation mechanisms for the electrosurgical devices previously discussed in connection with FIGS. 1-30, where jaw closure and articulation are on the same pivot.

FIGS. 33-37 depict articulation, clamping, and blade actuation mechanisms employing two rotations and a push-pull blade rather than a two push-pull articulation/clamping and one push-pull blade to perform the same functions.

Figure 33:
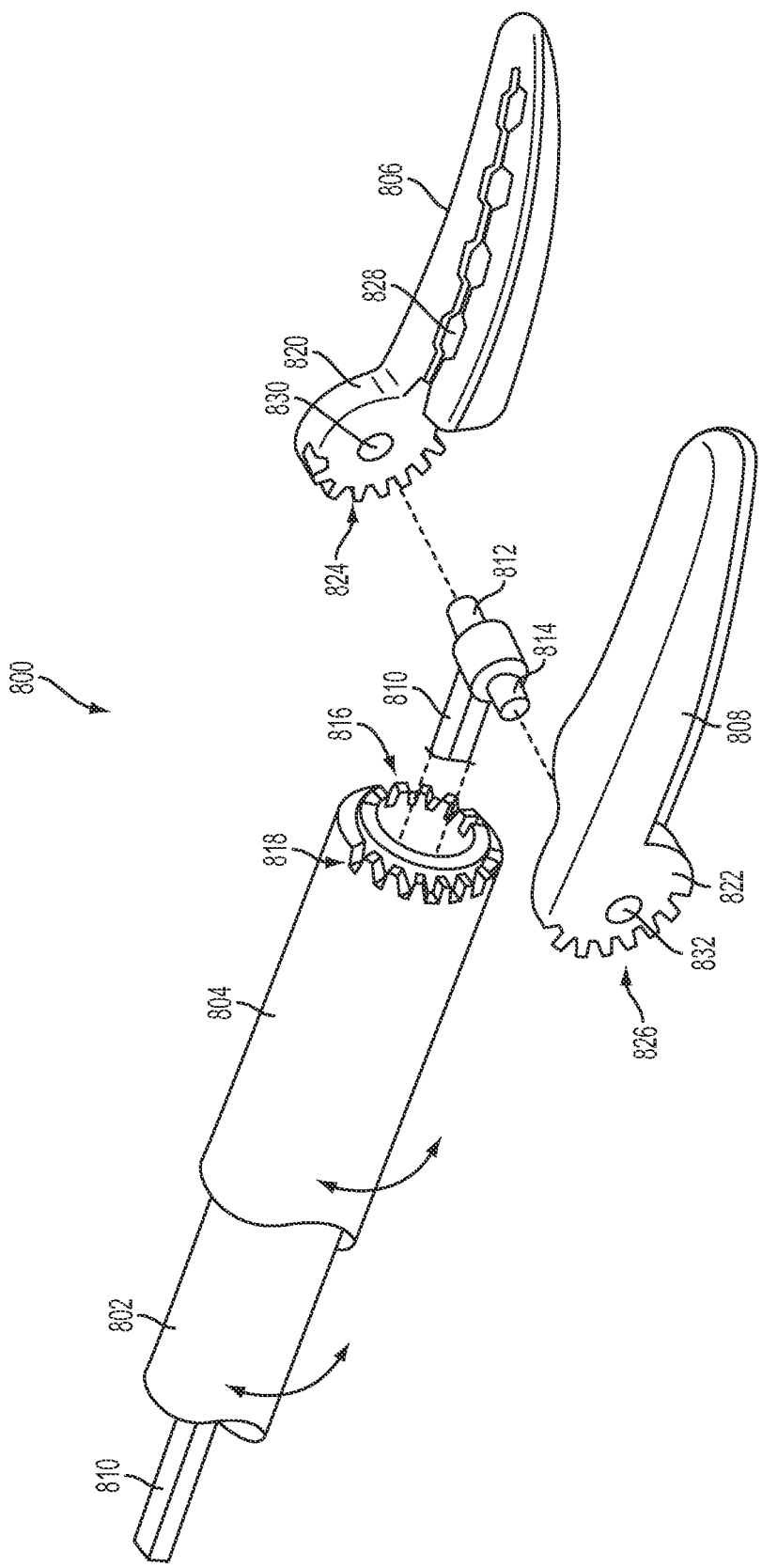

FIG. 33 depicts an exploded perspective view of one embodiment of an end effector with articulation, clamping, and blade actuation mechanisms employing two rotatable tubes for articulation and clamping and a push-pull blade to actuate the blade.

Figure 34:
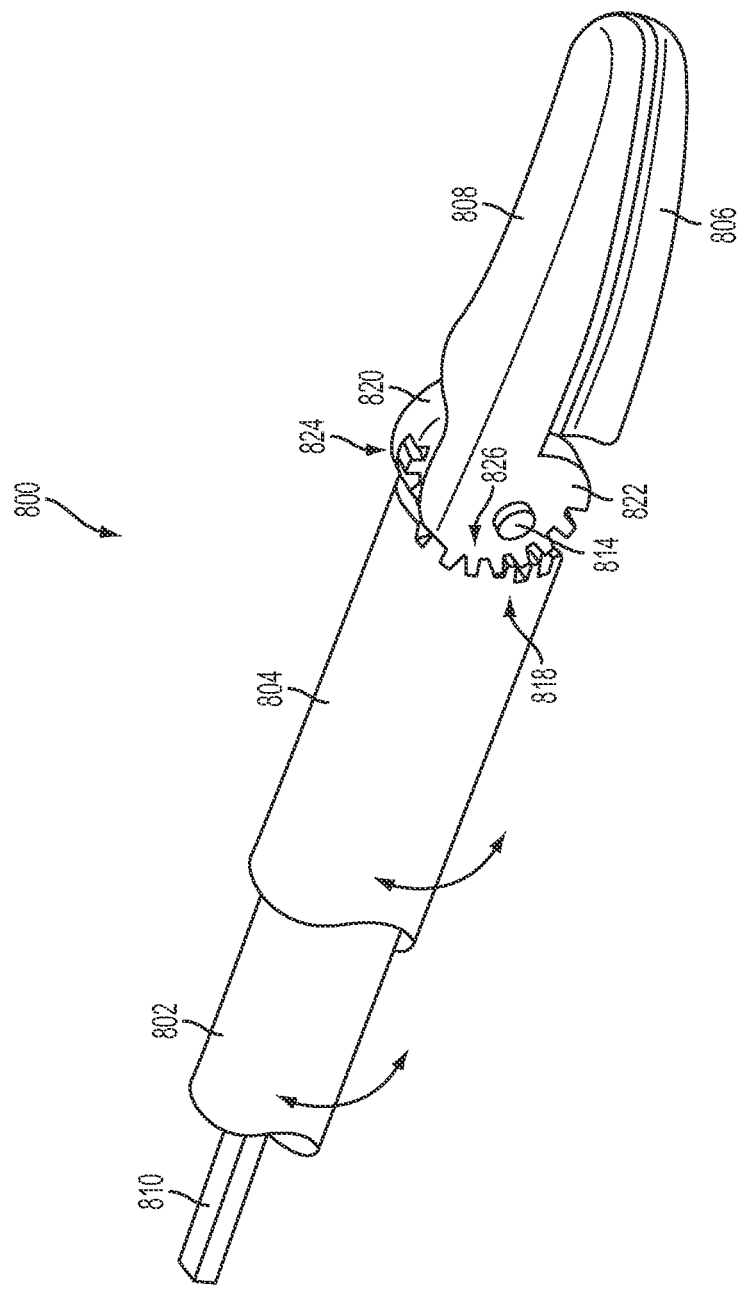

FIG. 34 depicts the end effector of FIG. 33 with the jaws in a closed (clamped) configuration.

Figure 35:
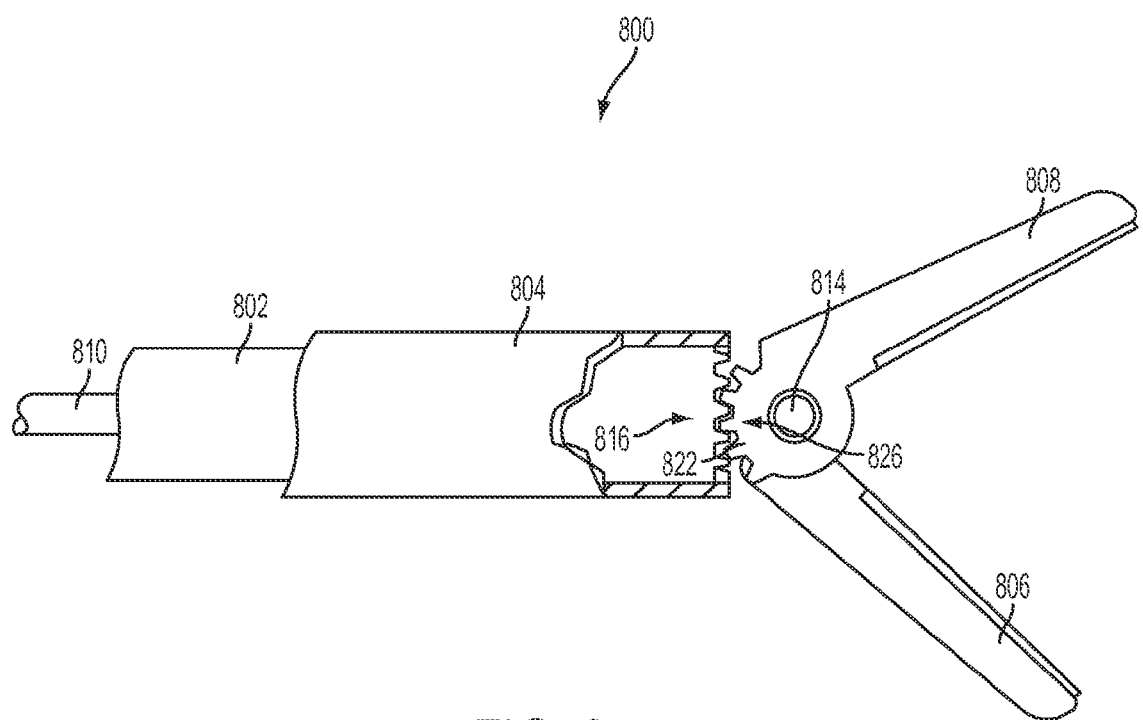

FIG. 35 depicts a side elevational partial cut-away view of the end effector shown in FIG. 33 with the jaws in an open (unclamped) configuration.

Figure 36A:
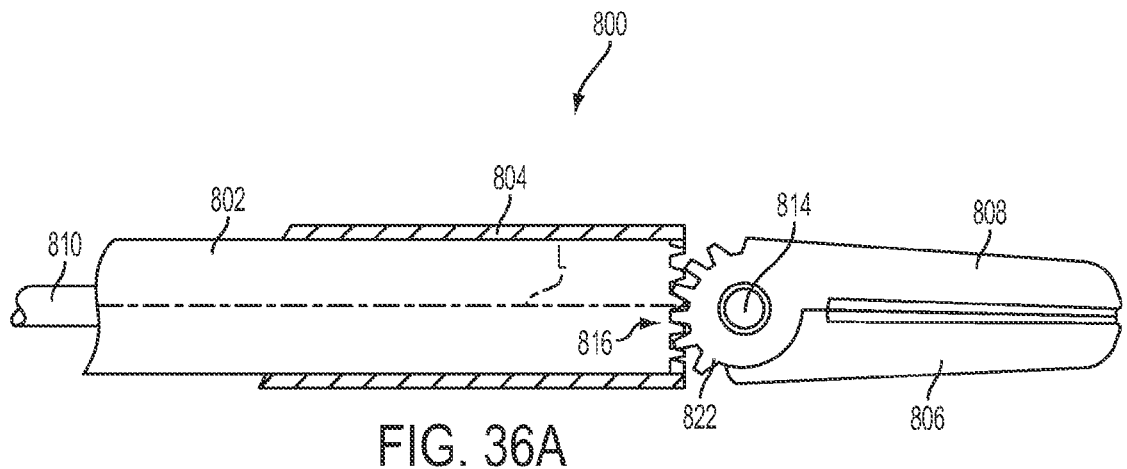
Figure 36B:
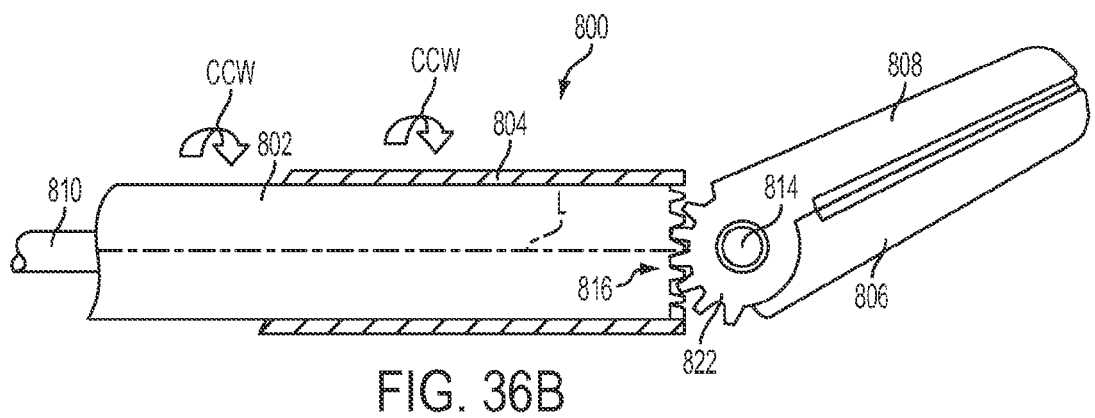
Figure 36C:
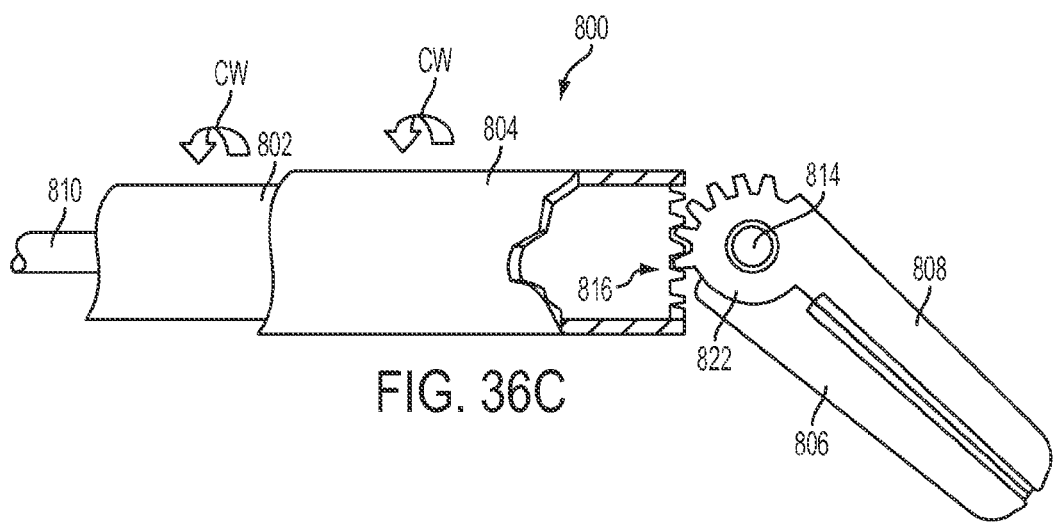

FIGS. 36A-C depict side elevational partial cut away views of the end effector of FIG. 33 during an articulation sequence, where FIG. 36A depicts an initial configuration where the jaws are clamped, FIG. 36B depicts an upward articulation with clamped jaws by rotating the rotatable inner and outer tubes in the same direction left (counterclockwise), and FIG. 36C depicts a downward articulation with clamped jaws by rotating the rotatable inner and outer tubes in the same direction right (clockwise).

Figure 37A:
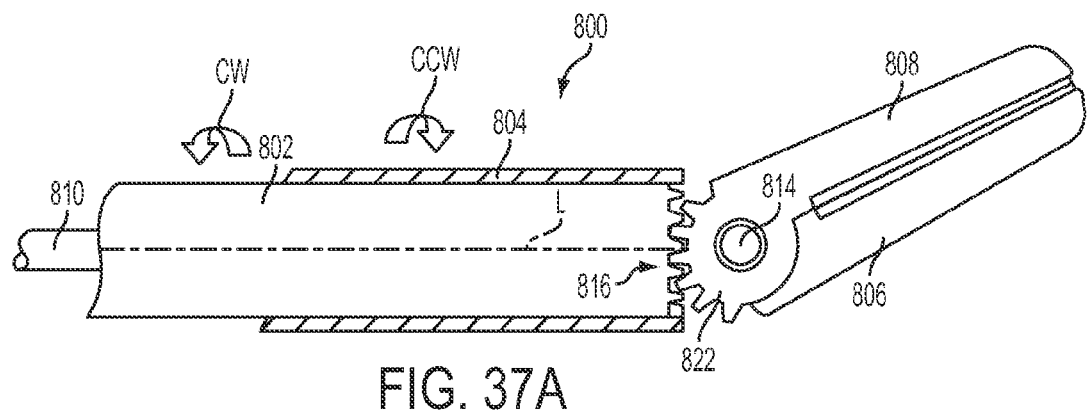
Figure 37B:
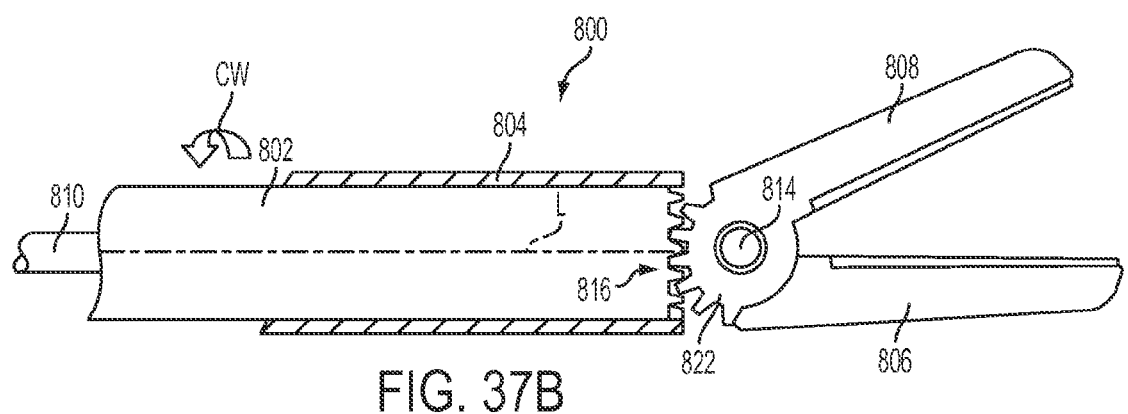
Figure 37C:
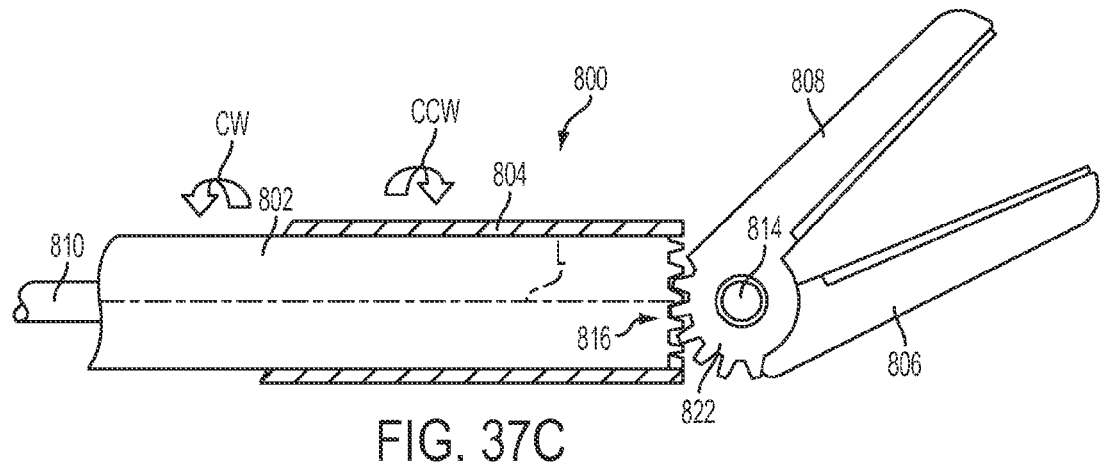

FIGS. 37A-C depict side elevational partial cut away views of the end effector of FIG. 33 during a jaw actuation sequence from an upward predetermined articulation configuration, where FIG. 37A depicts the end effector with the lower jaw rotated to a clamped position against the upper jaw by rotating the inner tube clockwise and the outer tube counterclockwise, FIG. 37B depicts the lower jaw rotating away from the upper jaw to an open position by rotating the inner clockwise and holding the outer tube fixed, and FIG. 37C depicts the lower jaw rotating toward the upper jaw from an open position by rotating the inner tube clockwise and the outer tube counterclockwise.

Figure 38:
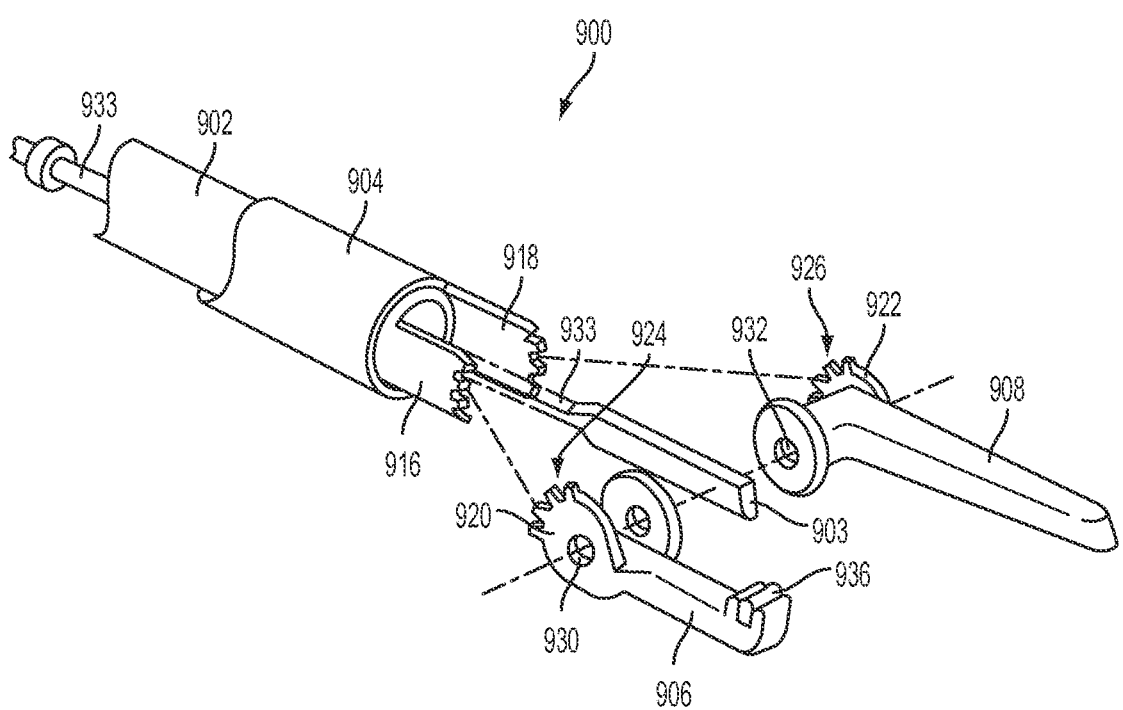

FIG. 38 depicts an exploded perspective view of one embodiment of an end effector with articulation and clamping mechanism and an ultrasonic blade employing two rotatable tubes for articulation and clamping.

Figure 39A:
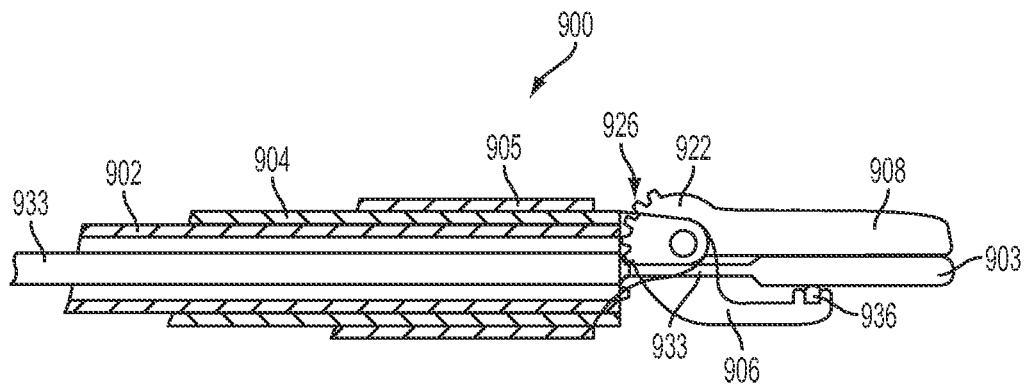
Figure 39B:
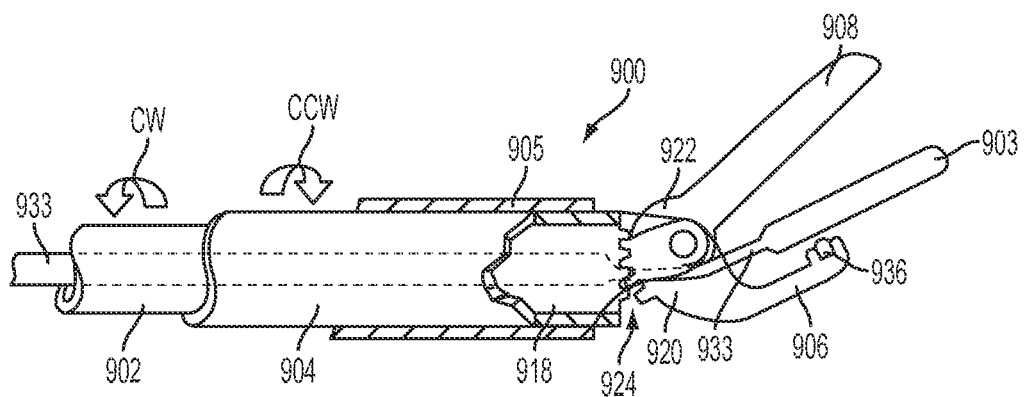
Figure 39C:
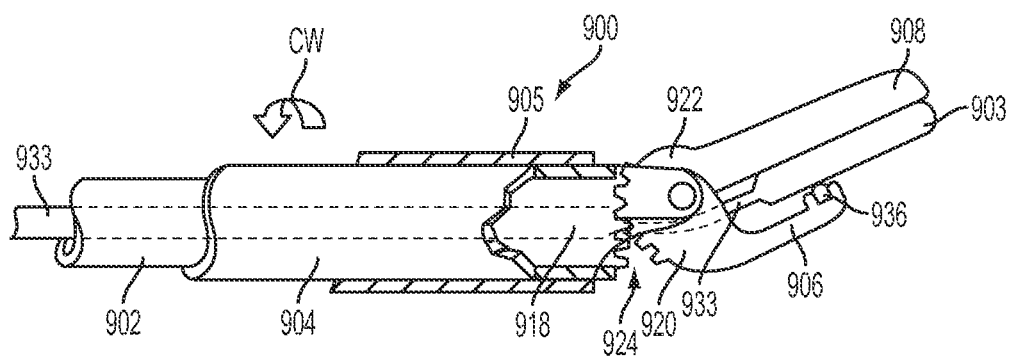

FIGS. 39A-C depict side elevational partial cut away views of the end effector of FIG. 38 during a jaw actuation sequence, where FIG. 39A depicts the end effector with the lower jaw and ultrasonic blade rotated to a clamped neutral longitudinal position, FIG. 39B depicts the upper jaw rotating upwardly away from the lower jaw to an open position by rotating the inner tube clockwise and rotating the outer tube counterclockwise, and FIG. 39C depicts the lower jaw rotating toward the upper jaw and clamping the ultrasonic blade therebetween by holding the inner tube and rotating the outer tube clockwise.

DESCRIPTION

In the following detailed description, reference is made to the accompanying drawings, which form a part hereof. In the drawings, similar symbols and reference characters typically identify similar components throughout the several views, unless context dictates otherwise. The illustrative embodiments described in the detailed description, drawings, and claims are not meant to be limiting. Other embodiments may be utilized, and other changes may be made, without departing from the spirit or scope of the subject matter presented here.

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Before explaining the various embodiments of the surgical devices with close quarter articulation features in detail, it should be noted that the various embodiments disclosed herein are not limited in their application or use to the details of construction and arrangement of parts illustrated in the accompanying drawings and description. Rather, the disclosed embodiments may be positioned or incorporated in other embodiments, variations and modifications thereof, and may be practiced or carried out in various ways. Accordingly, embodiments of the surgical devices with close quarter articulation features disclosed herein are illustrative in nature and are not meant to limit the scope or application thereof. Furthermore, unless otherwise indicated, the terms and expressions employed herein have been chosen for the purpose of describing the embodiments for the convenience of the reader and are not to limit the scope thereof. In addition, it should be understood that any one or more of the disclosed embodiments, expressions of embodiments, and/or examples thereof, can be combined with any one or more of the other disclosed embodiments, expressions of embodiments, and/or examples thereof, without limitation.

Also, in the following description, it is to be understood that terms such as front, back, inside, outside, top, bottom and the like are words of convenience and are not to be construed as limiting terms. Terminology used herein is not meant to be limiting insofar as devices described herein, or portions thereof, may be attached or utilized in other orientations. The various embodiments will be described in more detail with reference to the drawings.

I. Example Electrosurgical Device With Articulation Feature

FIGS. 1-27 show an electrosurgical instrument 10 that is constructed and operable to cut tissue and seal or weld tissue (e.g., a blood vessel, etc.) substantially simultaneously. In other words, the electrosurgical instrument 10 operates similar to an endocutter type of stapler, except that the electrosurgical instrument 10 provides tissue welding through application of bipolar RF energy instead of providing lines of staples to join tissue. Also, it should be understood that the electrosurgical instrument 10 may have various structural and functional similarities with the ENSEAL® Tissue Sealing Device by Ethicon Endo-Surgery, Inc., of Cincinnati, Ohio. To the extent that there is some degree of overlap between the teachings of the references cited herein, the ENSEAL® Tissue Sealing Device by Ethicon Endo-Surgery, Inc., of Cincinnati, Ohio, and the following teachings relating to the electrosurgical instrument 10, there is no intent for any of the description herein to be presumed as admitted prior art. Several teachings below will in fact go beyond the scope of the teachings of the references cited herein and the ENSEAL® Tissue Sealing Device by Ethicon Endo-Surgery, Inc., of Cincinnati, Ohio.

A. Example Handpiece And Shaft

Figure 1:
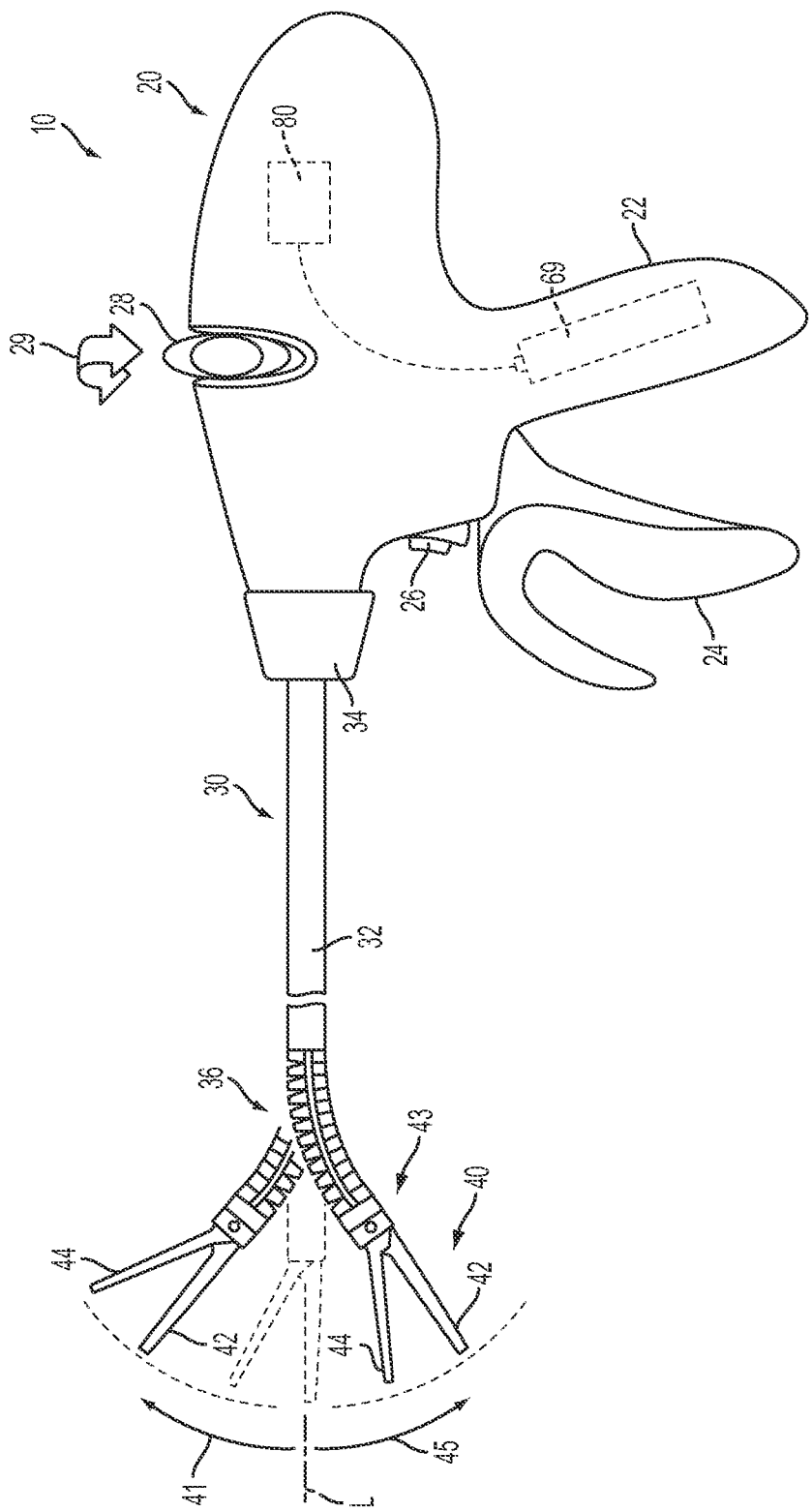
FIGS. 1-27 depict various embodiments of an articulatable radio frequency (RF) electrosurgical device configured to articulate up and down (vertical plane) rather than left to right (horizontal plane) with corresponding control mechanisms.

FIGS. 1-27 depict various embodiments of an articulatable radio frequency (RF) electrosurgical device configured to articulate up and down (vertical plane) rather than left to right (horizontal plane) with corresponding control mechanisms. Turning now to FIG. 1, which depicts a side elevational view of an articulatable electrosurgical instrument 10 showing up and down (vertical plane) articulation of an end effector 40 rather than left to right (horizontal plane) articulation of the end effector in response to a rotatable control mechanism 28 for activating longitudinal articulation movements, according to one embodiment. The electrosurgical instrument 10 of the present example includes a handpiece 20, a shaft 30 extending distally from the handpiece 20, and an end effector 40 disposed at a distal end of the shaft 30. The handpiece 20 of the present example includes a pistol grip 22, a pivoting trigger 24, an activation button 26, and an articulation control knob 28. The trigger 24 is pivotable toward and away from the pistol grip 22 to selectively actuate the end effector 40 as will be described in greater detail below. The activation button 26 is operable to selectively activate RF circuitry that is in communication with the end effector 40, as also will be described in greater detail below. In some versions, the activation button 26 also serves as a mechanical lockout against the trigger 24, such that the trigger 24 cannot be fully actuated unless the button 26 is being pressed simultaneously. Examples of how such a lockout may be provided are disclosed in one or more of the references cited herein. It should be understood that the pistol grip 22, the trigger 24, and the button 26 may be modified, substituted, supplemented, etc. in any suitable way, and that the descriptions of such components herein are merely illustrative.

The articulatable electrosurgical instrument 10 depicted in FIG. 1 has an articulation section 36 that can be articulated in an up direction 41 and a down direction 45 (vertical plane) rather than left to right (horizontal plane) articulation in response to activating the articulation control knob 28 mechanism, according to one embodiment. The articulation control knob 28 of the present example is operable to selectively control the articulation section 36 of the shaft 30, which will be described in greater detail below. In the illustrated example, rotating the articulation control knob 28 in accordance with arrow 29 causes the articulation section 36 to articulate up or down in the vertical direction. For example, from the perspective of a user holding the electrosurgical device 10, rotating the articulation control knob 28 in a clockwise direction causes the articulation section to articulate in a vertical up direction 41 and rotating the articulation control knob 28 in a counter-clockwise direction causes the articulation section to articulate in a vertical down direction 45. Various examples of forms that the articulation control knob 28 may take also will be described in greater detail below, while further examples will be apparent to those of ordinary skill in the art in view of the teachings herein.

The shaft 30 of the present example includes an outer sheath 32 and an articulation section 36. The articulation section 36 is operable to selectively position the end effector 40 at various angles relative to the longitudinal axis defined by the sheath 32. Various examples of forms that the articulation section 36 and other components of the shaft 30 may take will be described in greater detail below, while further examples will be apparent to those of ordinary skill in the art in view of the teachings herein. For instance, it should be understood that various components that are operable to actuate the articulation section 36 may extend through the interior of the sheath 32. In some versions, the shaft 30 also is rotatable about the longitudinal axis defined by the sheath 32, relative to the handpiece 20, via a knob 34. Such rotation may provide rotation of the end effector 40 and the shaft 30 unitarily. In some other versions, the knob 34 is operable to rotate the end effector 40 without rotating any portion of the shaft 30 that is proximal of the articulation section 36. As another merely illustrative example, the electrosurgical instrument 10 may include one rotation control that provides rotatability of the shaft 30 and the end effector 40 as a single unit; and another rotation control that provides rotatability of the end effector 40 without rotating any portion of the shaft 30 that is proximal of the articulation section 36. Other suitable rotation schemes will be apparent to those of ordinary skill in the art in view of the teachings herein. Of course, rotatable features may simply be omitted if desired.

The electrosurgical instrument 10 may comprise an on-board battery 69 powered electrical source 80 (e.g., RF generator). In other embodiments, an electrosurgical device may be electrically coupled to an RF generator by way of an electrical conductor in the form of a chord, as shown in FIG. 4, for example.

Figure 2:
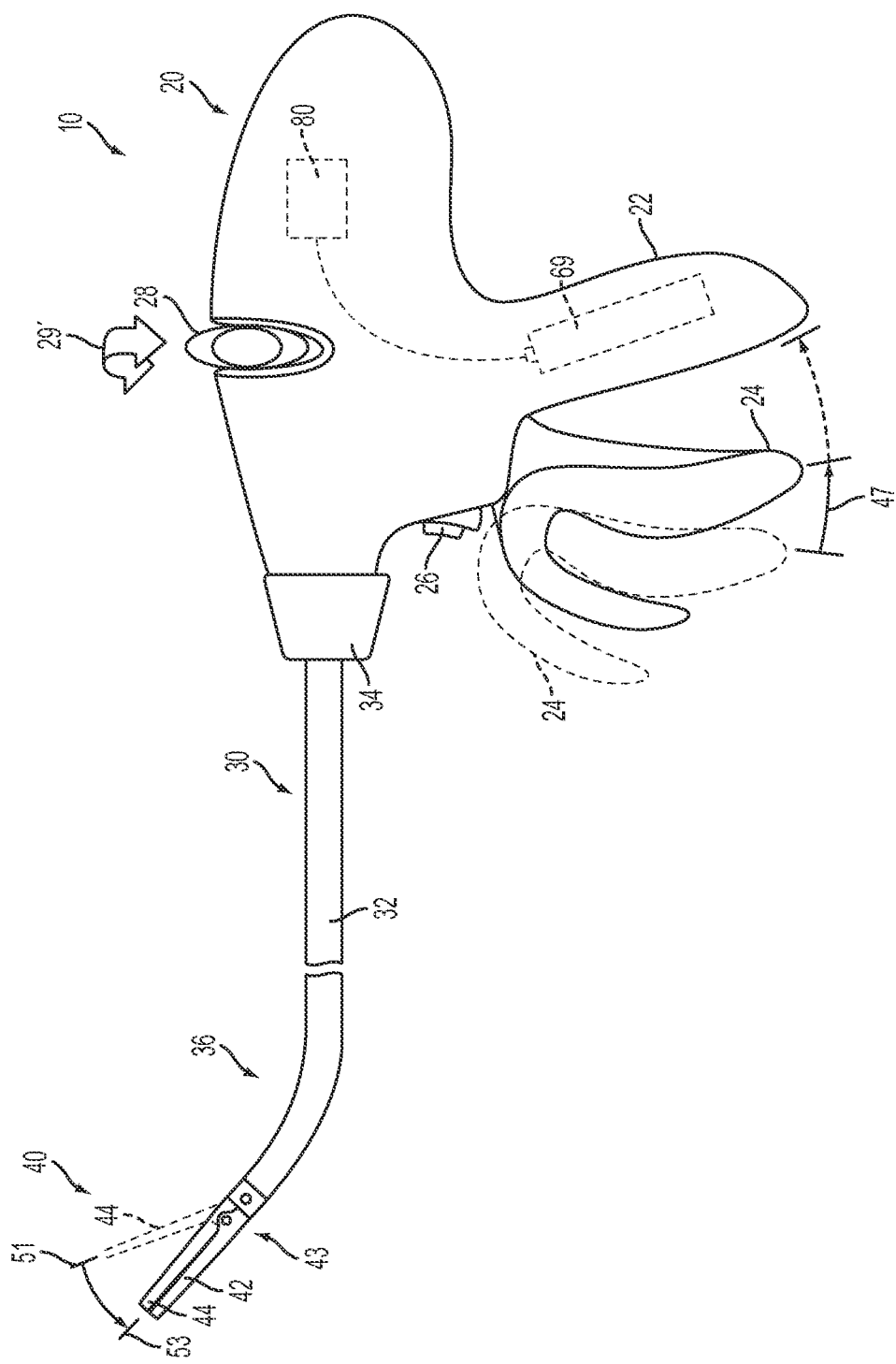

FIG. 2 depicts a side elevational view of the articulatable electrosurgical instrument 10 of FIG. 1 showing the end effector 40 of the device 10 articulated in an up 41 position and a jaw 44 of the end effector 40 clamped from an open position 51 (shown in phantom) to a closed position 53 in response to the pivoting trigger 24 being squeezed 47, according to one embodiment. As described in connection with FIG. 1, the end effector 40 is articulated in the up 41 position by rotating the articulation control knob 28 in a first direction 29' (e.g., clockwise relative to the user).

Figure 3:
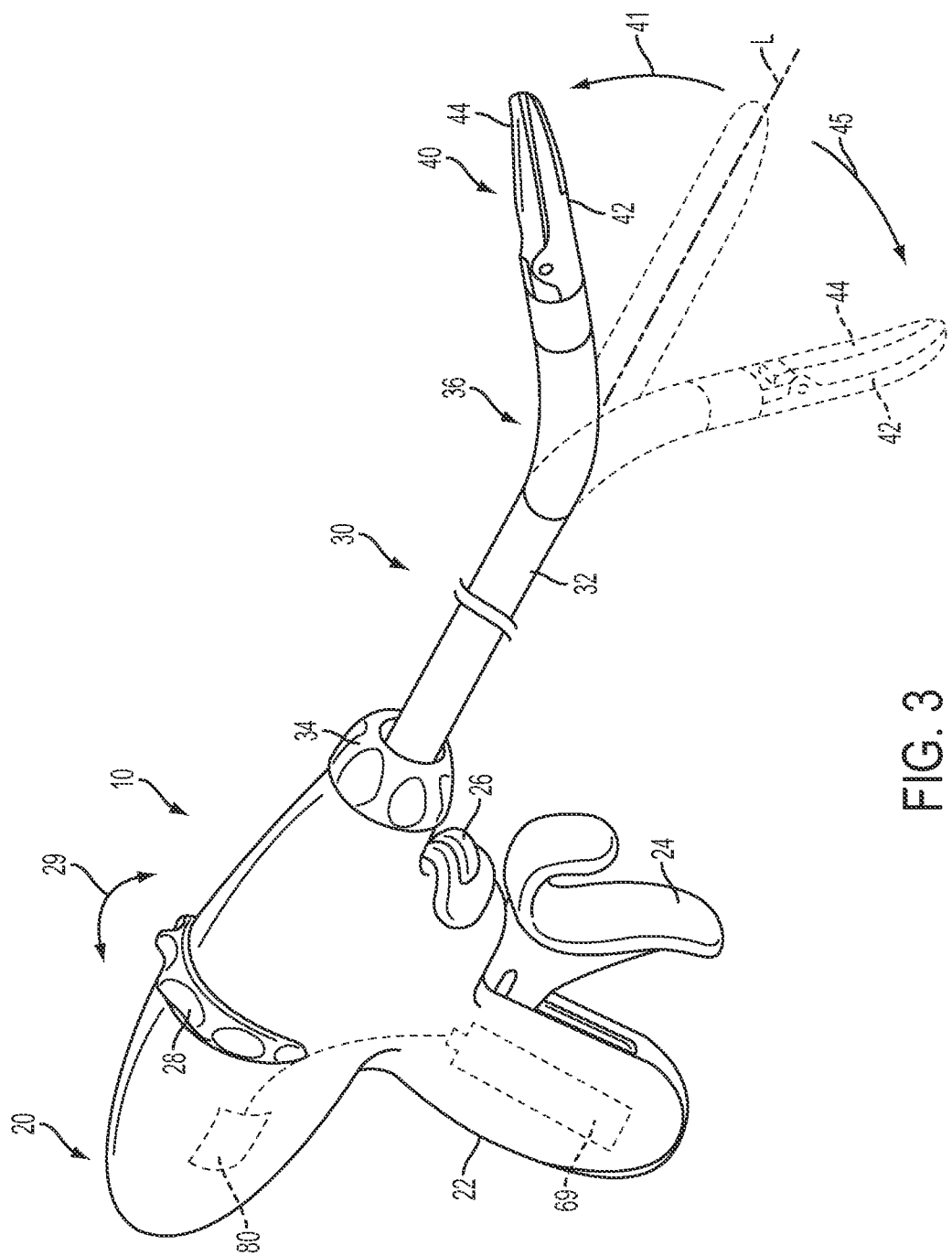

FIG. 3 depicts a perspective view of the articulatable electrosurgical medical 10 device of FIG. 1 showing up 41 and down 45 (vertical plane) articulation of the end effector 40 rather than left to right (horizontal plane) articulation of the end effector 40 in response to rotating the rotatable articulation control knob 28 mechanism for activating the up 41 and down 45 articulation movements of the end effector 40, according to one embodiment. Rotating the rotatable articulation control knob 28 mechanism in a first direction 55 causes the end effector 40 to articulate in the up 41 position and rotating the rotatable articulation control knob 28 mechanism in a second direction 57 causes the end effector 40 to articulate in the down up 45 position. As shown in FIG. 2, the jaw 44 can be opened/closed by squeezing/releasing the pivoting trigger 24 on the handle 22 of the electrosurgical instrument 10.

Figure 4:
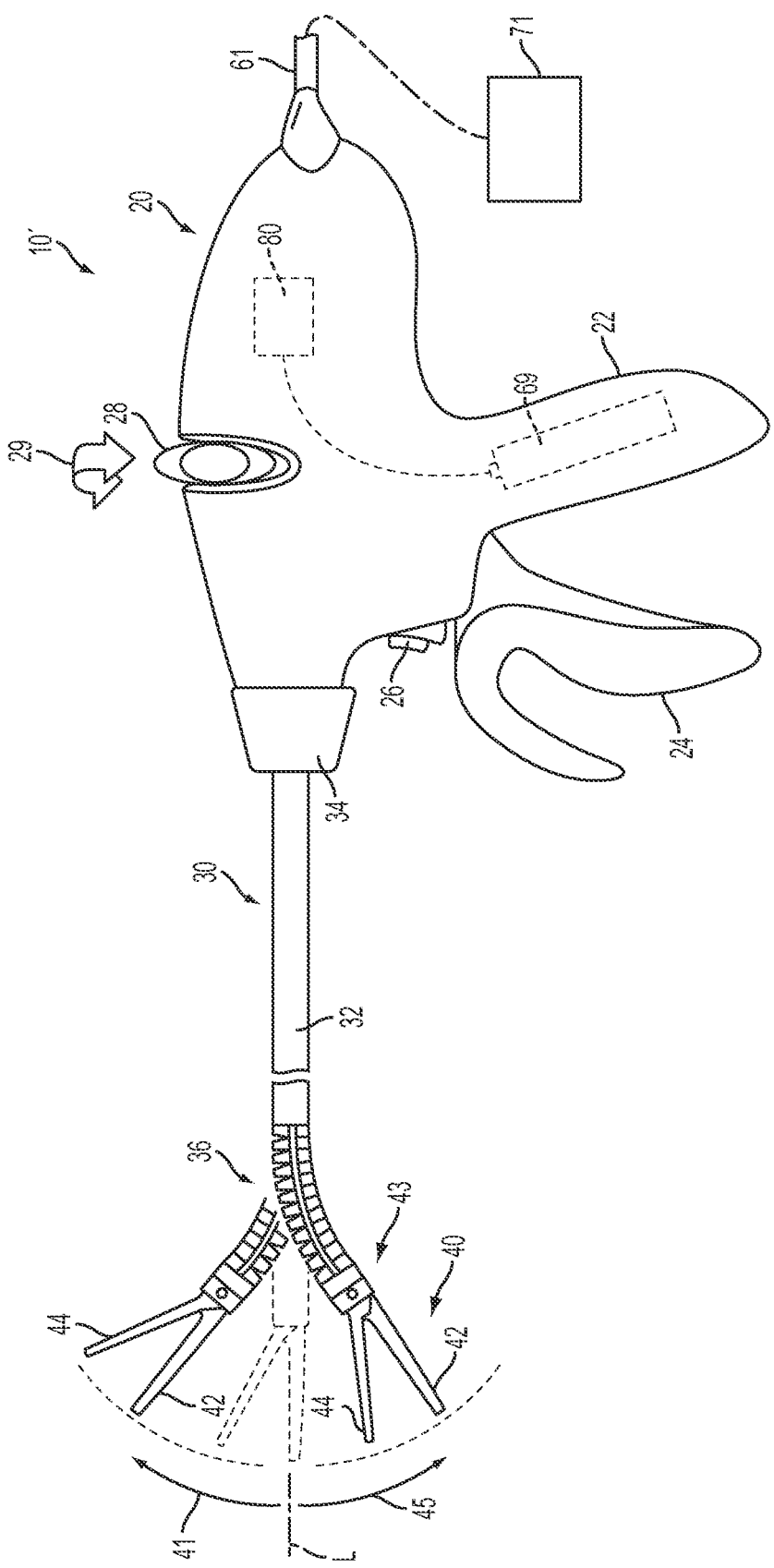

FIG. 4 depicts a perspective view of an articulatable electrosurgical instrument 10' showing up 41 and down 45 (vertical plane) articulation of the end effector 40 rather than left to right (horizontal plane) articulation of the end effector 40 in response to a rotatable articulation control knob 28 mechanism for activating the articulation movements, according to one embodiment. The electrosurgical instrument 10' shown in FIG. 4 is substantially similar to the electrosurgical instrument 10 shown in FIGS. 1-3, but also includes an electrical chord 61 to electrically couple the device to a suitable RF generator 71. In other embodiments, the articulatable electrosurgical instrument 10' also may comprise an on-board electrical generator 80 (e.g., RF generator) operated either by a battery 69 or an external power source coupled by the electrical chord 61. A switch may be provided to select the RF generator mode of operation.

The articulation control knob 28 shown in FIGS. 1-4, may take a variety of forms. By way of example only, the articulation control knob 28 may be configured in accordance with one or more teachings of U.S. Patent App. Pub. No. 2012/0078243 A1, entitled "Control Features for Articulating Surgical Device," filed on Sep. 19, 2011, the disclosure of which is incorporated by reference herein. As another merely illustrative example, articulation control knob 28 may be configured in accordance with one or more teachings of U.S. Patent App. Pub. No. 2012/0078244 A1, entitled "Control Features for Articulating Surgical Device," filed on Sep. 19, 2011, the disclosure of which is incorporated by reference herein. Furthermore, articulation section may be configured in accordance with the teachings of at least one other of the references cited herein. Various other suitable forms that the articulation control knob 28 may take will be apparent to those of ordinary skill in the art in view of the teachings herein.

B. Example End Effector

The end effector 40 of the present example comprises a first jaw 42 and a second jaw 44. In the present example, the first jaw 42 is substantially fixed relative to the shaft 30; while the second jaw 44 pivots relative to the shaft 30, toward and away from the first jaw 42. In some versions, actuators such as rods or cables, etc., may extend through the sheath 32 and be joined with the second jaw 44 at a pivotal coupling 43, such that longitudinal movement of the actuator rods/cables/etc. through the shaft 30 provides pivoting of the second jaw 44 relative to the shaft 30 and relative to the first jaw 42. Of course, the jaws 42, 44 may instead have any other suitable kind of movement and may be actuated in any other suitable fashion. By way of example only, and as will be described in greater detail below, the jaws 42, 44 may be actuated and thus closed by longitudinal translation of a flexible firing element 60, such that actuator rods/cables/etc. may simply be eliminated in some versions. In the illustrated embodiment, the flexible firing element 60 includes an upper flexible band 65 (FIG. 7) connected to an upper flange 62 portion of a distal blade 64 and a lower flexible band 67 (FIG. 7) connected to a lower flange 66 (FIG. 7) portion of the distal blade 64. Attaching separate upper and lower flexible bands 65, 67 to the corresponding upper and lower flanges 62, 66 enables the articulation section 36 of the shaft 30 to articulate in the vertical plane (up/down) rather than the horizontal plane (let/right).

Figure 5:
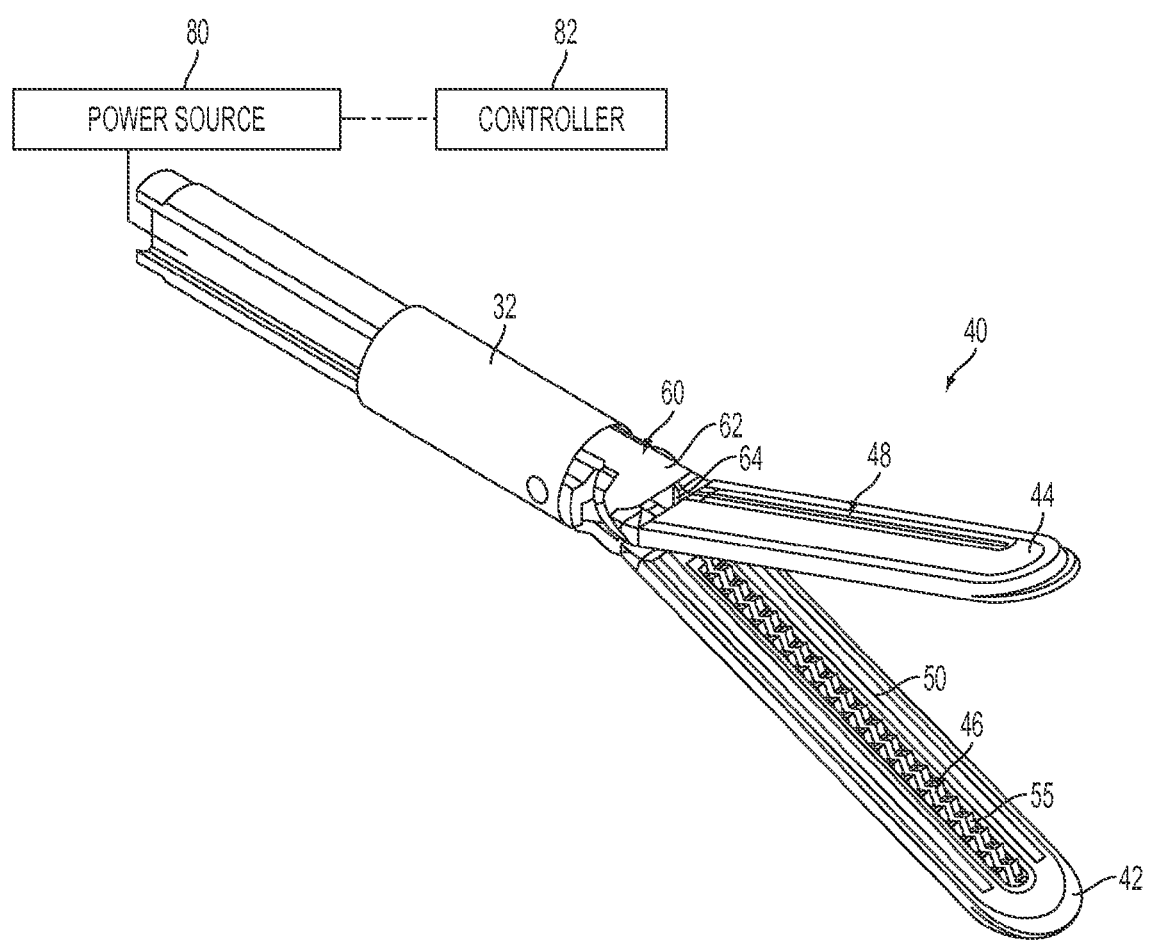
Figure 6:
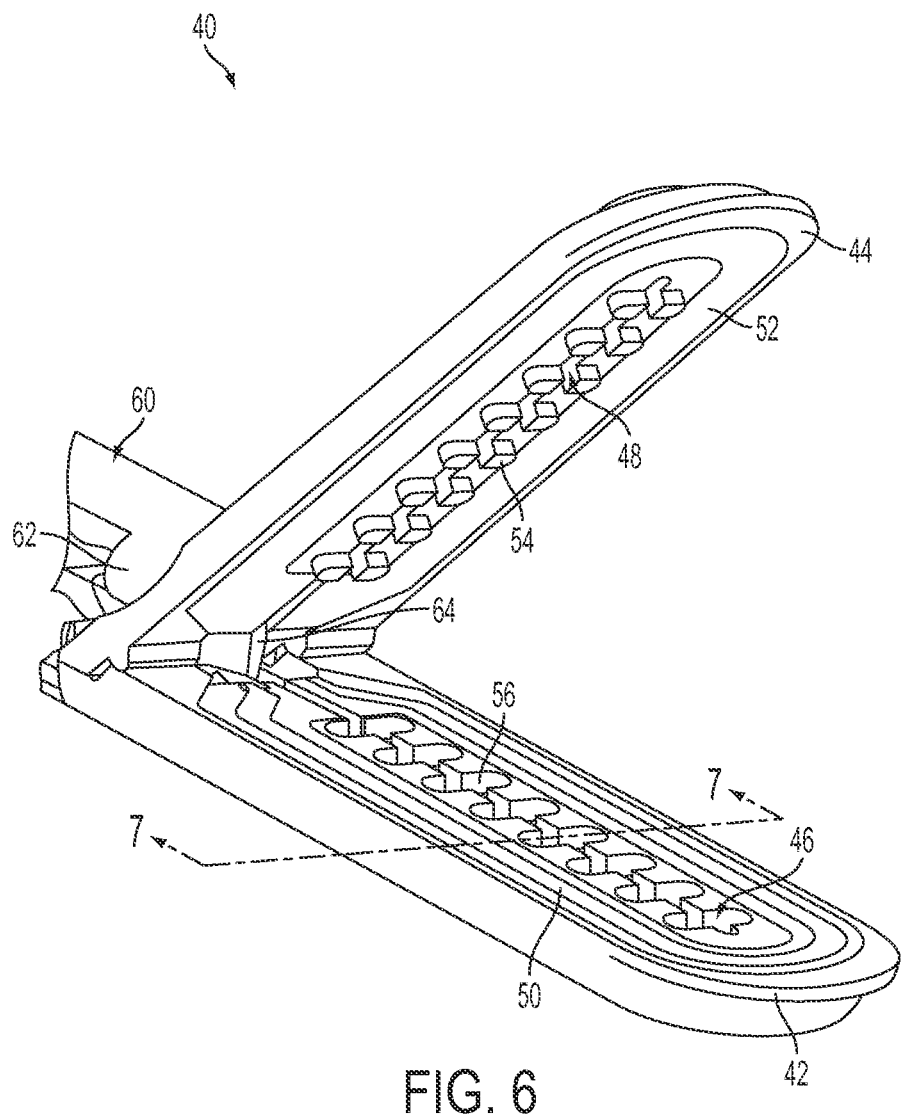

As best seen in FIGS. 5-6, the first jaw 42 defines a longitudinally extending elongate slot 46; while the second jaw 44 also defines a longitudinally extending elongate slot 48. In addition, the top side of the first jaw 42 presents a first electrode surface 50; while the underside of the second jaw 44 presents a second electrode surface 52. The electrode surfaces 50, 52 are in communication with an electrical source 80 (generator) via one or more conductors (not shown) that extend along the length of the shaft 30. The electrical source 80 is operable to deliver RF energy to the first electrode surface 50 at a first polarity and to the second electrode surface 52 at a second (opposite) polarity, such that RF current flows between the electrode surfaces 50, 52 and thereby through tissue captured between the jaws 42, 44. In some versions, the flexible firing element 60 may serve as an electrical conductor that cooperates with the electrode surfaces 50, 52 (e.g., as a ground return) for delivery of bipolar RF energy captured between the jaws 42, 44. The electrical source 80 may be external to the electrosurgical instrument 10 or may be integral with the electrosurgical instrument 10 (e.g., associated with the handpiece 20, etc.), as described in one or more references cited herein or otherwise. A controller 82 regulates delivery of power from the electrical source 80 to the electrode surfaces 50, 52. The controller 82 also may be external to the electrosurgical instrument 10 or may be integral with the electrosurgical instrument 10 (e.g., associated with the handpiece 20, etc.), as described in one or more references cited herein or otherwise. It should also be understood that the electrode surfaces 50, 52 may be provided in a variety of alternative locations, configurations, and relationships. In one example, the electrical source 80 may be battery powered, wherein one or more than one battery may be located within the housing or remote from the housing through one or more electrical conductors.

Figure 7:
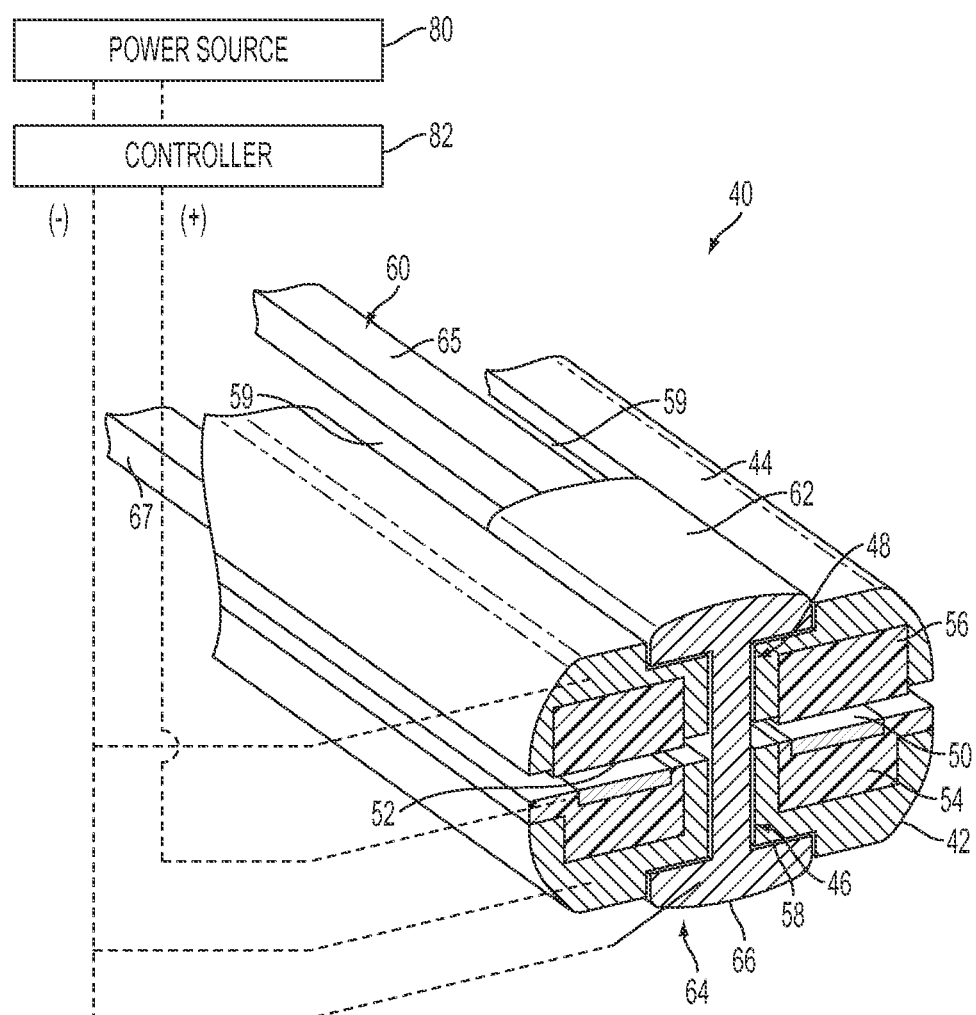

As best seen in FIG. 7, the lower side of the first jaw 42 includes a longitudinally extending recess 58 adjacent to the slot 46; while the upper side of the second jaw 44 includes a longitudinally extending recess 59 adjacent to the slot 48. FIG. 5 shows the upper side of the first jaw 42 including a plurality of teeth serrations 46. It should be understood that the lower side of the second jaw 44 may include complementary serrations that nest with the serrations 46 of the first jaw 42 to enhance gripping of tissue captured between the jaws 42, 44 without necessarily tearing the tissue. FIG. 6 shows an example of serrations 46 in the first jaw 42 as mainly recesses; with serrations 48 in the second jaw 44 as mainly protrusions. Of course, the serrations 46, 48 may take any other suitable form or simply may be omitted altogether. It should also be understood that the serrations 46, 48 may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to the jaws 42, 44.

With the jaws 42, 44 in a closed position, the shaft 30 and the end effector 40 are sized and configured to fit through trocars having various inner diameters, such that the electrosurgical instrument 10 is usable in minimally invasive surgery, though of course the electrosurgical instrument 10 also could be used in open procedures if desired. By way of example only, with the jaws 42, 44 in a closed position, the shaft 30 and the end effector 40 may present an outer diameter of approximately 5 mm. Alternatively, the shaft 30 and the end effector 40 may present any other suitable outer diameter (e.g., between approximately 2 mm and approximately 20 mm, etc.).

As another merely illustrative variation, either jaw 42, 44 or both jaws 42, 44 may include at least one port, passageway, conduit, and/or other feature that is operable to draw steam, smoke, and/or other gases/vapors/etc. from the surgical site. Such a feature may be in communication with a source of suction, such as an external source or a source within the handpiece 20, etc. In addition, the end effector 40 may include one or more tissue cooling features (not shown) that reduce the degree or extent of thermal spread caused by the end effector 40 on adjacent tissue when the electrode surfaces 50, 52 are activated. Various suitable forms that such cooling features may take will be apparent to those of ordinary skill in the art in view of the teachings herein.

In some versions, the end effector 40 includes one or more sensors (not shown) that are configured to sense a variety of parameters at the end effector 40, including but not limited to temperature of adjacent tissue, electrical resistance or impedance of adjacent tissue, voltage across adjacent tissue, forces exerted on the jaws 42, 44 by adjacent tissue, etc. By way of example only, the end effector 40 may include one or more positive temperature coefficient (PTC) thermistor bodies 54, 56 (e.g., PTC polymer, etc.), located adjacent to electrodes 50, 52 and/or elsewhere. Data from the sensors may be communicated to the controller 82. The controller 82 may process such data in a variety of ways. By way of example only, the controller 82 may modulate or otherwise change the RF energy being delivered to the electrode surfaces 50, 52, based at least in part on data acquired from the one or more sensors at the end effector 40. In addition or in the alternative, the controller 82 may alert the user to one or more conditions via an audio and/or visual feedback device (e.g., speaker, lights, display screen, etc.), based at least in part on data acquired from one or more sensors at the end effector 40. It also should be understood that some kinds of sensors need not necessarily be in communication with the controller 82, and may simply provide a purely localized effect at the end effector 40. For instance, bodies 54, 56 of a PTC thermistor at the end effector 40 may automatically reduce the energy delivery at the electrode surfaces 50, 52 as the temperature of the tissue and/or the end effector 40 increases, thereby reducing the likelihood of overheating. In some such versions, a PTC thermistor element is in series with the power source 80 and the electrode surface 50, 52; and the PTC thermistor provides increased impedance (reducing flow of current) in response to temperatures exceeding a threshold. Furthermore, it should be understood that the electrode surfaces 50, 52 may be used as sensors (e.g., to sense tissue impedance, etc.). Various kinds of sensors that may be incorporated into electrosurgical instrument 10 will be apparent to those of ordinary skill in the art in view of the teachings herein. Similarly, various things that can be done by the controller 82, or otherwise, with data from sensors, that will be apparent to those of ordinary skill in the art in view of the teachings herein. Other suitable variations for the end effector 40 will also be apparent to those of ordinary skill in the art in view of the teachings herein.

C. Example Firing Beam

As also seen in FIGS. 5-7, the electrosurgical instrument 10 of the present example includes a flexible firing element 60 that is longitudinally movable along part of the length of the end effector 40. The flexible firing element 60 is coaxially positioned within the shaft 30, extends along the length of the shaft 30, and translates longitudinally within the shaft 30 including the articulation section 36 in the present example), though it should be understood that the flexible firing element 60 and the shaft 30 may have any other suitable relationship. The flexible firing element 60 includes a sharp distal blade 64, an upper flange 62, and a lower flange 66. As best seen in FIG. 7, the distal blade 64 extends through the slots 46, 48 of the jaws 42, 44, with the upper flange 62 being located above the second jaw 44 in the recess 59 and the lower flange 66 being located below the first jaw 42 in the recess 58. The configuration of the distal blade 64 and the flanges 62, 66 provides an "I-beam" type of cross section at the distal end of flexible firing element 60. While the flanges 62, 66 extend longitudinally only along a small portion of the length of flexible firing element 60 in the present example, it should be understood that the flanges 62, 66 may extend longitudinally along any suitable length of the flexible firing element 60. In addition, while the flanges 62, 66 are positioned along the exterior of the jaws 42, 44, the flanges 62, 66 may alternatively be disposed in the corresponding slots formed within the jaws 42, 44. For instance, each jaw 42, 44 may define a "T"-shaped slot, with parts of the distal blade 64 being disposed in one vertical portion of each "T"-shaped slot and with the flanges 62, 66 being disposed in the horizontal portions of the "T"-shaped slots. Various other suitable configurations and relationships will be apparent to those of ordinary skill in the art in view of the teachings herein.

The distal blade 64 is substantially sharp, such that the distal blade 64 will readily sever tissue that is captured between the jaws 42, 44. The distal blade 64 also is electrically grounded in the present example, providing a return path for RF energy as described elsewhere herein. In some other versions, the distal blade 64 serves as an active electrode. In addition or in the alternative, the distal blade 64 may be selectively energized with ultrasonic energy (e.g., harmonic vibrations at approximately 55.5 kHz, etc.).

The configuration of the flexible firing element 60 provides closure of the jaws 42, 44 as the flexible firing element 60 is advanced distally. In particular, the flange 62 urges the second jaw 44 pivotally toward the first jaw 42 as the flexible firing element 60 is advanced from a proximal position to a distal position, by bearing against the recess 59 formed in the second jaw 44. This closing effect on the jaws 42, 44 by the flexible firing element 60 may occur before the distal blade 64 reaches tissue captured between the jaws 42, 44. Such staging of encounters by the flexible firing element 60 may reduce the force required to squeeze the grip 24 to actuate the flexible firing element 60 through a full firing stroke. In other words, in some such versions, the flexible firing element 60 may have already overcome an initial resistance required to substantially close the jaws 42, 44 on the tissue before encountering resistance from the tissue captured between the jaws 42, 44. Of course, any other suitable staging may be provided.

In the present example, the flange 62 is configured to cam against a ramp feature at the proximal end of the first jaw 42 to open the second jaw 44 when the flexible firing element 60 is retracted to a proximal position and to hold the second jaw 44 open when the flexible firing element 60 remains at the proximal position. This camming capability may facilitate use of the end effector 40 to separate layers of tissue, to perform blunt dissections, etc., by forcing the jaws 42, 44 apart from a closed position. In some other versions, the jaws 42, 44 are resiliently biased to an open position by a spring or other type of resilient feature. While the jaws 42, 44 close or open as the flexible firing element 60 is translated, as described in the present example, it should be understood that other versions may provide independent movement of the jaws 42, 44 and the flexible firing element 60. By way of example only, one or more cables, rods, beams, or other features may extend through the shaft 30 to selectively actuate the jaws 42, 44 independently of the flexible firing element 60. Such jaw 42, 44 actuation features may be separately controlled by a dedicated feature of the handpiece 20. Alternatively, such jaw actuation features may be controlled by the trigger 24 in addition to having the trigger 24 control the flexible firing element 60. It should also be understood that the flexible firing element 60 may be resiliently biased to a proximal position, such that the flexible firing element 60 retracts proximally when a user relaxes their grip on the trigger 24.

D. Example Operation

In one use, the end effector 40 is inserted into a patient via a trocar. The articulation section 36 is substantially straight when the end effector 40 and part of the shaft 30 are inserted through the trocar. The articulation control knob 28 then may be manipulated to pivot or flex the articulation section 36 of the shaft 30 in order to position the end effector 40 at a desired position and orientation relative to an anatomical structure within the patient. Two layers of tissue of the anatomical structure are then captured between the jaws 42, 44 by squeezing the trigger 24 toward the pistol grip 22. Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of the electrosurgical instrument 10 is perpendicular to the longitudinal axis defined by the end effector 40, etc.). In other words, the lengths of the jaws 42, 44 may be oriented perpendicular to (or at least generally transverse to) the length of the blood vessel. As noted above, the flanges 62, 66 cammingly act to pivot the second jaw 44 toward the first jaw 42 when the flexible firing element 60 is actuated distally by squeezing the trigger 24 toward the pistol grip 22.

With layers of tissue captured between the jaws 42, 44, the flexible firing element 60 continues to advance distally by the user squeezing the trigger 24 toward the pistol grip 22. As the flexible firing element 60 advances distally, the distal blade 64 simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of the flanges 62, 66 immediately above and below the jaws 42, 44, respectively, may suffice to keep the jaws 42, 44 in a closed and tightly clamping position. In particular, the flanges 62, 66 may suffice to maintain a significantly compressive force between the jaws 42, 44. With severed tissue layer portions being compressed between the jaws 42, 44, the electrode surfaces 50, 52 are activated with bipolar RF energy by the user depressing the activation button 26. In some versions, the electrodes 50, 52 are selectively coupled with the power source 80 (e.g., by the user depressing the button 26, etc.) such that the electrode surfaces 50, 52 of the jaws 42, 44 are activated with a common first polarity while firing the beam 60 is activated at a second polarity that is opposite to the first polarity. Thus, a bipolar RF current flows between the flexible firing element 60 and the electrode surfaces 50, 52 of the jaws 42, 44 through the compressed regions of severed tissue layer portions. In some other versions, one electrode surface 50 has one polarity while the other electrode surface 52 and the flexible firing element 60 both have the other polarity. In either version (among at least some others), bipolar RF energy delivered by the power source 80 ultimately thermally welds the tissue layer portions on one side of the flexible firing element 60 together and the tissue layer portions on the other side of the flexible firing element 60 together.

In certain circumstances, the heat generated by activated electrode surfaces 50, 52 can denature the collagen within the tissue layer portions and, in cooperation with clamping pressure provided by the jaws 42, 44, the denatured collagen can form a seal within the tissue layer portions. Thus, the severed ends of the natural lumen defining anatomical structure are hemostatically sealed shut, such that the severed ends will not leak bodily fluids. In some versions, the electrode surfaces 50, 52 may be activated with bipolar RF energy before the flexible firing element 60 even begins to translate distally and thus before the tissue is even severed. For instance, such timing may be provided in versions where the button 26 serves as a mechanical lockout relative to the trigger 24 in addition to serving as a switch between the power source 80 and the electrode surfaces 50, 52.

While several of the teachings below are described as variations to the electrosurgical instrument 10, it should be understood that various teachings below may also be incorporated into various other types of devices. By way of example only, in addition to being readily incorporated into the electrosurgical instrument 10, various teachings below may be readily incorporated into the devices taught in any of the references cited herein, other types of electrosurgical devices, surgical staplers, surgical clip appliers, and tissue graspers, among various other devices. Other suitable devices into which the following teachings may be incorporated will be apparent to those of ordinary skill in the art in view of the teachings herein.

II. Example Articulation Joint Configurations

As noted above, some versions of the shaft 30 include an articulation section 36, which is operable to selectively position the end effector 40 at various vertical angles relative to the longitudinal axis L defined by the sheath 32. Several examples of forms that the articulation section 36 and other components of the shaft 30 may take will be described in greater detail below, while further examples will be apparent to those of ordinary skill in the art in view of the teachings herein. By way of example only, some merely illustrative alternative examples of the articulation section 36 are disclosed in U.S. Patent App. Pub. No. US 2012/0078248 A1, entitled "Articulation Joint Features for Articulating Surgical Device," the disclosure of which is incorporated by reference herein.

A. Example Articulation Section With Vertically Spaced Parallel Support Rails

FIG. 8 depicts a perspective view of an articulation section 100 for the shaft of the device 10 of FIG. 1. FIG. 9 depicts a cross-sectional end view of the articulation section 100 of FIG. 8, taken along line 9-9 of FIG. 8 for a device having independent articulation and end effector actuator control mechanisms. As shown in FIGS. 8-9 an example articulation section 100 is disposed between a rigid shaft section 102 extending along a longitudinal axis L (x) and an end effector 140. It should be understood that these features may be readily incorporated into the electrosurgical instrument 10 described above, as well as others, with the shaft section 102 corresponding to the shaft 30 and the end effector 140 corresponding to the end effector 40. The articulation section 100 of this example comprises a molded member 110 that defines a plurality of slots 112, 114, 116 and a pair of recesses 118. The molded member 110 may comprise a variety of materials, including but not limited to Vectra, Isoplast, a high density polyethylene, and/or various other materials. In some instances, the material forming the molded member 110 provides a resilient bias to the molded member 110 to assume a substantially straight orientation. Other suitable selections and properties for the molded member 110 will be apparent to those of ordinary skill in the art in view of the teachings herein. Similarly, while the molded member 110 is formed through a molding process in the present example, it should be understood that a variety of other processes may be used, including but not limited to extrusion, etc.

The slots 112 extend longitudinally along the length of the molded member 110, opening at a top portion of the molded member 110 but terminating within the bottom portion of the molded member 110. The slots 112, 114 extend along the axis of the molded member 110 and are oriented transversely relative to the axis of the molded member 110. Like the slots 112, the slots 114 also open at one side portion of the molded member 110 while terminating within the other side of the molded member 110. The slots 116 are configured to facilitate flexing of the molded member 110 up/down in a vertical plane V (xy), relative to the longitudinal axis L (x), in the same plane (xy) in which the jaws 142, 144 of the end effector 140 pivotally open and close. The slot 112 is configured to slidably receive upper and lower flexible bands 165, 167 of a flexible firing element 160, where the flexible firing element 160 comprises an upper flexible band 165 connected to an upper flange portion of a distal blade 164 and a lower flexible band 167 connected to a lower flange portion of the distal blade 164. Attaching the upper and lower flexible bands 165, 167 to corresponding upper and lower flanges of the distal blade 164 enables the articulation section 100 to articulate in the vertical plane (up/down) rather than the horizontal plane (let/right). The flexible firing element 160 is equivalent to the flexible firing element 60 discussed above and the distal blade 164 includes upper and lower flanges equivalent to the upper and lower flanges 62, 66 of the distal blade 64 discussed above in connection with FIGS. 6-7. It should therefore be understood that the upper and lower flexible bands 165, 167 of the firing element 160 are operable to translate longitudinally within the slot 112. It should also be understood that the upper and lower flexible bands 165, 167 of the flexible firing element 160 have sufficient flexibility to enable the firing beam to translate along a curved path when articulation section is in a bent, articulated configuration. The material forming the molded member 110 and/or coatings on the molded member 110 may be selected to minimize friction between the firing element 160 and the molded member 110. By way of example only, the molded member 110 may include baked on silicone and/or sodium stearate and/or various other materials.

The recesses 118 are configured to receive vertically spaced upper and lower articulation bands 122, 124. The distal ends of the articulation bands 122, 124 are secured to the distal end of the articulation section 100. The proximal ends of the upper and lower articulation bands 122, 124 are in communication with a control such as the rotatable articulation control knob 28 (FIGS. 1-4). As shown in FIG. 17 and described more fully in connection with FIGS. 24-27, in some versions, the articulation control knob 28 is operable to selectively advance or retract one articulation band 122, 124 while keeping the position of the other articulation band 122, 124 substantially constant, thereby causing articulation section 100 to bend in a vertical plane relative to the longitudinal axis. In some other versions, the rotatable articulation control knob 28 is operable to selectively advance one articulation band 122 while simultaneously retracting the other articulation band 124; and/or to selectively retract one articulation band 122 while simultaneously advancing the other articulation band 122. Of course, the articulation bands 122, 124 may be substituted with cables and/or various other types of components. A flexible sheath or wrap may be positioned about the articulation section 100, to assist in holding the articulation bands 122, 124 against the molded member 110. In addition or in the alternative, the molded member 110 may include vertically extending slots and/or other types of features that hold the articulation bands 122, 124 against the molded member 110, including when the articulation section 100 is in a bent configuration.

The slot 114 is configured to slidably receive an actuation member 150 to control the actuation of the jaws 142, 144 (e.g., open/close) in the vertical plane V (xy), relative to the longitudinal axis L (x), that is independent of the triggering of the flexible firing element 160. In some versions, the actuation member 150 may be operatively connected to the pivoting trigger 24 of the electrosurgical instrument 10 to open and close jaws 142, 144 of the end effector 140. Thus, when the pivoting trigger 24 is initially squeezed, the actuation member 150 advances distally to close the jaws 142, 144. As the pivoting trigger 24 is continued to be squeezed, the flexible firing element 160, comprising upper and lower flexible bands 165, 167 is fired.

Other suitable components, configurations, arrangements, and relationships will be apparent to those of ordinary skill in the art in view of the teachings herein. It should also be understood that any of the slots 112, 114, 116 and/or some other component of the articulation section 110 may accommodate one or more wires that provide electrical communication between the end effector 140 and a power source.

Figure 10:
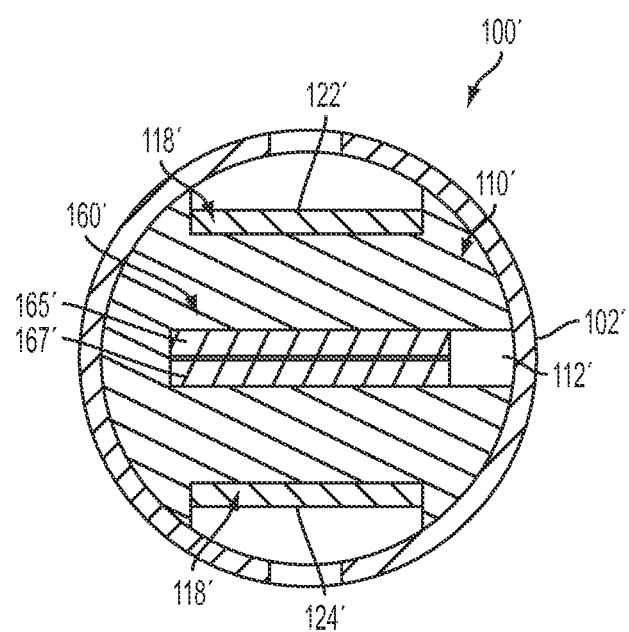

FIG. 10 depicts a cross-sectional end view of an articulation section 100' for an electrosurgical device with simultaneous firing and jaw actuation control. In the example articulation section 100', the slot 114 and the actuation member 150 shown in FIG. 9 are eliminated because these elements were employed to independently advance/retract the distal blade 164 and closing/opening the jaw 144. Rather, the articulation section 100' of FIG. 10 comprises a shaft section 102' comprising a slot 112' for slidably receiving upper and lower flexible bands 165', 167' and recesses 118' for slidably receiving upper and lower articulation bands 122', 124'. In the articulation section 100' shown in FIG. 10, the upper and lower flexible bands 165', 167' are configured to simultaneously advance/retract the distal blade 164 and closing/opening the jaw 144 of the end effector 140.

B. Example Articulation Section Formed By Molded Joint

Figure 11:
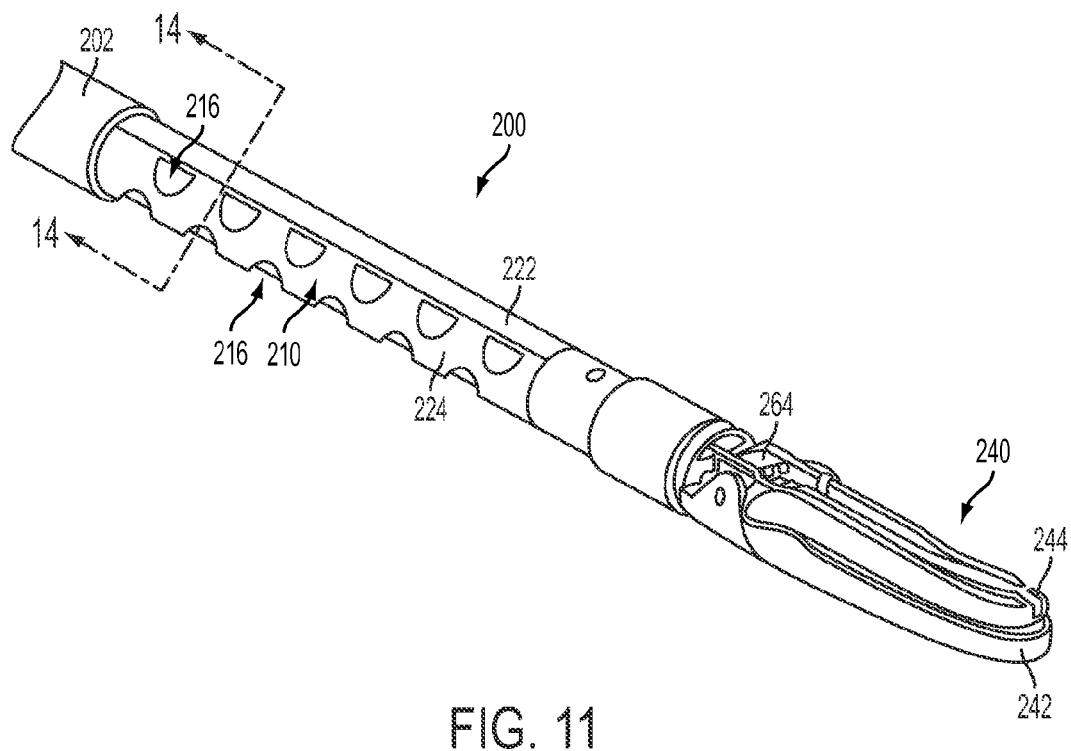
Figure 12:
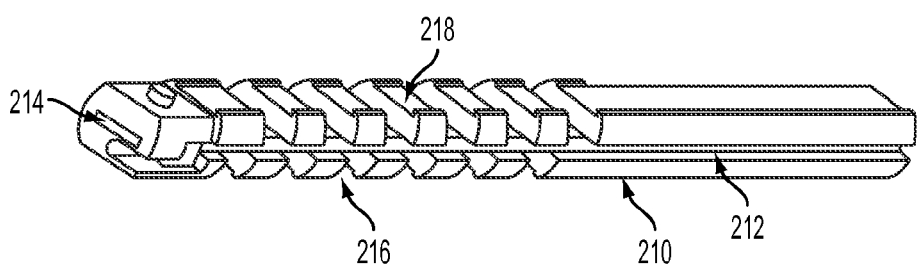
Figure 13:
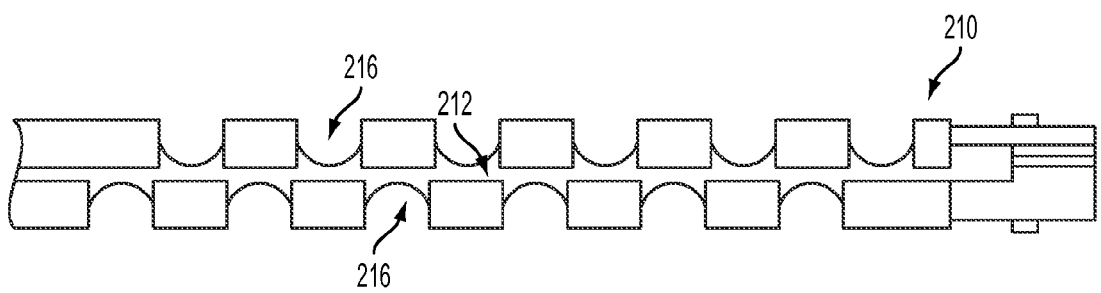

FIGS. 11-13 show another example articulation section 200 disposed between a rigid shaft section 202 extending along a longitudinal axis L and an end effector 204. It should be understood that these features may be readily incorporated into the electrosurgical instrument 10 described above, with the shaft section 202 corresponding to the shaft 30 and the end effector 240 corresponding to the end effector 40. The articulation section 200 of this example comprises a molded member 210 that defines a plurality of slots 216, a lumen 214, and a pair of recesses 218. The molded member 210 may comprise a variety of materials, including but not limited to Vectra, Isoplast, a high density polyethylene, and/or various other materials. In some instances, the material forming the molded member 210 provides a resilient bias to the molded member 210 to assume a substantially straight orientation. Other suitable selections and properties for the molded member 210 will be apparent to those of ordinary skill in the art in view of the teachings herein. Similarly, while the molded member 210 is formed through a molding process in the present example, it should be understood that a variety of other processes may be used.

As best seen in FIGS. 12-13, the slot 212 and the lumen 214 each extend longitudinally along the length of the molded member 110. The slot 212 is configured to accommodate one or more wires that provide electrical communication between the end effector 204 and a power source. The lumen 214 is configured to slidably receive a firing beam (not shown), much like the slot 112 receiving the firing element 160 as described above. Thus, a firing beam may translate through the molded member 210 regardless of whether the articulation section 200 is in a substantially straight or bent configuration. The slots 216 are oriented transversely relative to the axis of the molded member 210. The slots 216 are configured to facilitate flexing of the molded member 210. In the present examples, as best seen in FIG. 12, the slots 216 are alternatingly staggered in their relative spacing along the length of the molded member 210. Such a configuration may facilitate bending of the molded member 210. In some other versions, the slots 216 are opposingly positioned instead of being staggered.

The recesses 218 are configured to receive the articulation bands 222, 224. The distal ends of the articulation bands 222, 224 are secured to the distal end of the articulation section 200. The proximal ends of the articulation bands 222, 224 are in communication with a control such as the articulation control knob 28. In some versions, the articulation control knob 28 is operable to selectively advance or retract one articulation band 222, 224 while keeping the position of the other articulation band 222, 224 substantially constant, thereby causing the articulation section 200 to bend. In some other versions, the articulation control knob 28 is operable to selectively advance the articulation band 222 while simultaneously retracting one articulation band 224; and/or to selectively retract the other articulation band 222 while simultaneously advancing the one articulation band 224. As yet another merely illustrative example, the rotatable articulation control knob 28 may be operable to selectively advance articulation band 222 while letting the articulation band 224 remain slack/free; and/or to selectively retract the articulation band 222 while letting the other articulation band 224 remain slack/free. Of course, the articulation bands 222, 224 may be substituted with cables and/or various other types of components; and may be operable in various other ways.

A flexible sheath or wrap may be positioned about the articulation section 200, to assist in holding the articulation bands 222, 224 against the molded member 210. In addition or in the alternative, the molded member 210 may include vertically extending slots and/or other types of features that hold the articulation bands 222, 224 against the molded member 210, including when the articulation section 200 is in a bent configuration. As described in connection with FIGS. 14-15, the distal blade 264 can be fired independently of or simultaneously with the actuation (closure) of the jaws 242, 244.

Figure 14:
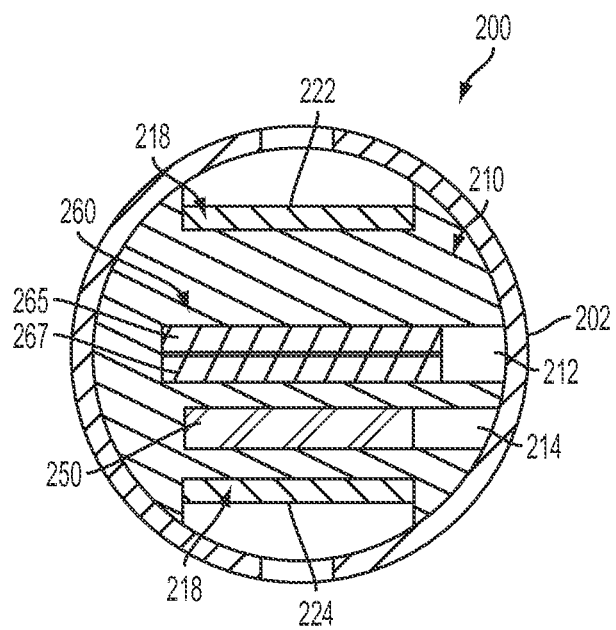

FIG. 14 depicts a cross-sectional end view of an articulation section 200 of FIG. 10, taken along line 14-14 of FIG. 11, for an electrosurgical device with independent firing and jaw actuation control. Accordingly, similar to the embodiment shown in FIG. 9, in the embodiment shown in FIG. 14, the articulation section 200 comprises a slot 214 to slidably receive the actuation member 250 for closing/opening the jaws 242, 244 independently of firing the distal blade 264 with the upper and lower flexible bands 265, 267 of the flexible firing element 260.

Figure 15:
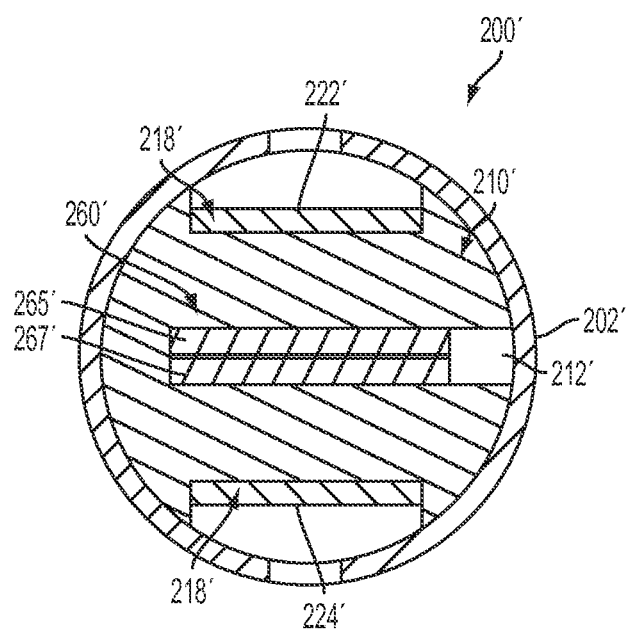

FIG. 15 depicts a cross-sectional end view of an articulation section 200' for an electrosurgical device with simultaneous firing and jaw actuation control. In the example articulation section 200', the slot 214 and the actuation member 250 shown in FIG. 14 are eliminated because these elements were employed to independently advance/retract the distal blade 264 and closing/opening the jaw 244. Rather, the articulation section 200' of FIG. 14 comprises a shaft section 202' comprising a slot 212' for slidably receiving upper and lower flexible bands 265', 267' and recesses 218' for slidably receiving upper and lower articulation bands 222', 224'. The upper and lower flexible bands 265', 267' are configured for simultaneously advancing/retracting the distal blade 264 and closing/opening the jaw 244 of the end effector 240.

Figure 16:
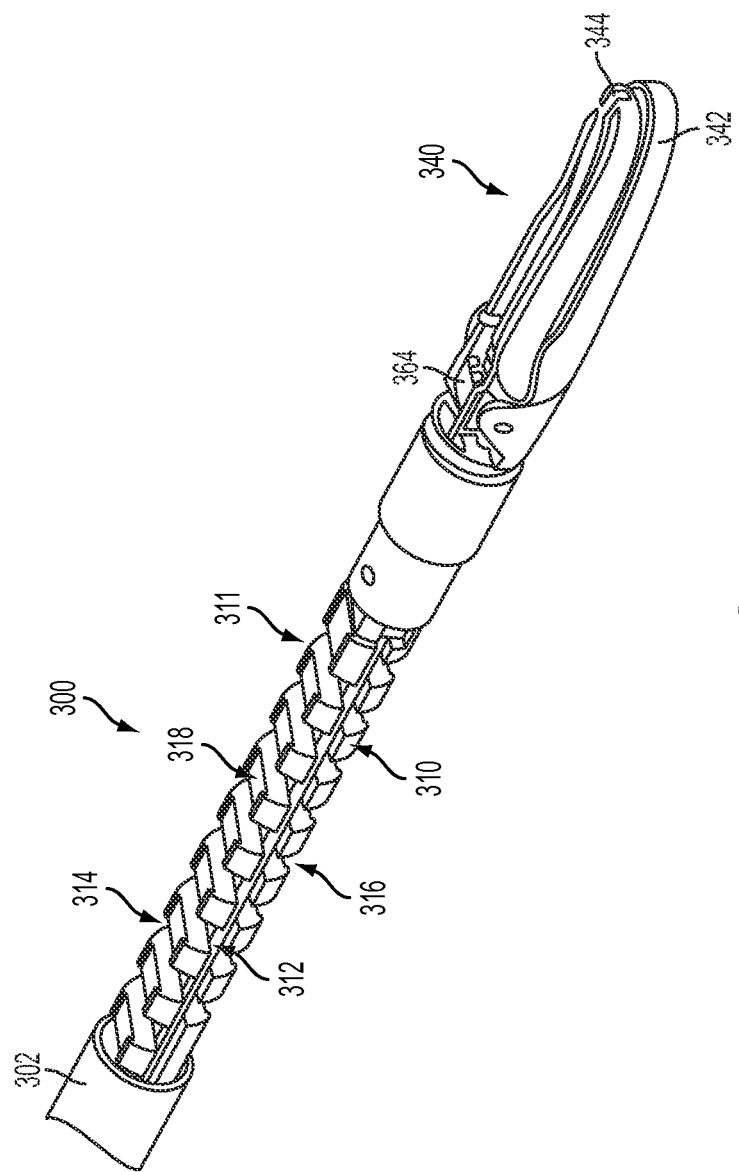

FIG. 16 show another example articulation section 300 disposed between a rigid shaft section 302 and an end effector 340. It should be understood that these features may be readily incorporated into the electrosurgical instrument 10 described above, with the shaft section 302 corresponding to the shaft 30 and the end effector 340 corresponding to the end effector 40. The articulation section 300 of this example comprises a pair of molded members 310, 311. Each molded member 310, 311 may comprise a variety of materials, including but not limited to Vectra, Isoplast, a high density polyethylene, and/or various other materials. In some instances, the material forming the molded members 310, 311 provides a resilient bias to the molded members 310, 311 to assume a substantially straight orientation. Other suitable selections and properties for the molded members 310, 311 will be apparent to those of ordinary skill in the art in view of the teachings herein. Similarly, while the molded members 310, 311 are formed through a molding process in the present example, it should be understood that a variety of other processes may be used. The molded members 310, 311 are configured to opposingly join together to form the articulation section 300, as shown in FIG. 16. The molded members 310, 311 may be secured together in numerous ways, including but not limited to adhesives, ultrasonic welding, snap-fittings, clamps, clips, an external sheath, etc.

As best seen in FIG. 14, the molded member 310 includes a plurality of recesses 312, 316. The recesses 312, 316 all extend longitudinally along the length of the molded member 310. The recess 316 is positioned on an upper side of the molded member 310 to accommodate a lower articulation band (not shown). The recess 312 is configured to accommodate one or more wires that provide electrical communication between the end effector 304 and a power source. The other molded member 311 also includes a plurality of recesses 314, 318. The recesses 314, 318 all extend longitudinally along the length of the molded member 311. The recess 318 is positioned on an upper side of the molded member 311 to accommodate an upper articulation band (not shown).

When the molded members 310, 311 are joined together as shown in FIG. 16, the recesses 312, 314 align and cooperate to form a channel through which a firing beam (not shown) may be slidably disposed. This channel is thus functionally similar to the lumen 214 described above. In addition, one set of recesses 316 align and cooperate to form a channel to receive a first articulation cable (not shown) while the other recesses 318 align and cooperate to form another channel to receive a second articulation cable (not shown) when molded members 310, 311 are joined together. Such articulation cables may be operable in a manner similar to that described above for the articulation bands 122, 124, 222, 224. In some other versions, the recesses 316, 318 are configured to form channels that receive cables bands instead of bands. Other suitable features that may be used to provide articulation of the articulation section 300 will be apparent to those of ordinary skill in the art in view of the teachings herein. As shown in FIG. 16, an end effector 340 includes first and second jaws 342, 244 with a slot that receives a distal blade 364.

FIG. 17 depicts articulation and end effector sections of the device shown in FIGS. 8 and 9. The articulation control knob 28 (FIGS. 1-4) is operable to selectively advance 170 or retract 172 one articulation band 122, 124 while keeping the position of the other articulation band 122, 124 substantially constant, thereby causing articulation section 100 to bend in a vertical plane relative to the longitudinal axis L. In some other versions, the rotatable articulation control knob 28 is operable to selectively advance 170 one articulation band 122 while simultaneously retracting 172 the other articulation band 124; and/or to selectively retract one articulation band 122 while simultaneously advancing the other articulation band 122. Of course, the articulation bands 122, 124 may be substituted with cables and/or various other types of components. A flexible sheath or wrap may be positioned about the articulation section 100, to assist in holding the articulation bands 122, 124 against the molded member 110. In addition or in the alternative, the molded member 110 may include vertically extending slots and/or other types of features that hold the articulation bands 122, 124 against the molded member 110, including when the articulation section 100 is in a bent configuration.

FIGS. 18-20 depict cross-sectional views of the articulation section 100 and end effector 140 shown in FIGS. 8, 9, and 17 with independent articulation and end effector 140 actuator control and a bar linkage 171 to provide mechanical advantage. FIG. 18 depicts the end effector 140 jaws 144, 142 in an open position prior to deploying a cutting blade 164. FIG. 19 depicts the end effector 140 jaws 144, 142 in a closed position prior to deploying the cutting blade 164. FIG. 20 depicts the end effector 140 jaws 142, 144 in a closed position as the cutting blade 164 is being deployed. The present embodiment provides a technique to improve access to vessels and difficult to get at tissues by articulating the articulation section 36 up and down (vertically) rather than left to right (horizontally) relative to the longitudinal axis L. The present embodiment further provides a flexible firing element by connecting flexible bands to the firing element pins rather than a vertical strut connecting them. Having the ability to push on both the top and bottom of the firing element minimizes the tendency of cocking and binding as it is advanced. The flexible firing element then follow the firing element pins into enclosed upper and lower jaw tracks which will prevent the flexible firing elements from buckling as the cutting blade is advanced. The present embodiment also provides an improved jaw clamp track which cams the jaws tighter and provides for positive jaw opening. In accordance with estimated calculations, 45-60 degrees of articulation may be achieved on a 1 in. bend radius for the flexible firing element laminates. This in-plane articulation improves access to difficult to get to vessels and arteries. The positive jaw opening provides for better dissection and tissue manipulation. Improved clamping load provides improved tissue holding force.

The present embodiment will now be described with reference to FIGS. 18-20, where the articulation section 100 shows the flexible firing element 160 comprising first and second flexible bands 165, 167. The flexible bands 165, 167 are coupled to respective upper and lower flanges 162, 166 of the cutting blade 164. The cutting blade 164 includes a sharp portion 178 on the distal end for cutting through tissue grasped between the jaws 142, 144 of the end effector 140. At a proximal end, the bar linkage 171 is pivotally coupled to the actuation member 150 at pivot 173 and at a distal end the bar linkage 171 is pivotally coupled to a tab 176 portion of the upper jaw 144 at pivot 174. The upper jaw 144 is a beam that pivotally rotates about a pivot 174. The lower jaw 142 does not move and is rigidly attached to the shaft section 102. As shown in the sequence of FIGS. 18-20, as the actuation member 150 is advanced distally, the bar linkage 171 pivots about pivots 173, 174 to act on the tab 176 portion of the upper jaw 144 and as the cam follower 182 acts on the slot cam 184, the upper jaw 144 is forced to close against the lower jaw 142. As best seen in FIG. 20, the bar linkage 171 provides a mechanical advantage to exert a closing force on the upper jaw 142 against the lower jaw 142. Accordingly, the cam surfaces 182 and the bar linkage 171 cooperate to improve the mechanical closure strength of the upper and lower jaws 144, 142. The embodiment illustrated in FIGS. 18-20 provides independent articulation and end effector 140 actuation. Accordingly, once the jaws 142, 144 are closed against each other to grasp tissue therebetween, the cutting blade 164 is advanced to cut the tissue with the sharp distal portion 178 by advancing the flexible firing member 160 distally.

FIGS. 21-23 depict cross-sectional views of articulation section 100' and end effector 140' with a simultaneous articulation and end effector 140' actuator control mechanisms and a bar linkage 171' to provide mechanical advantage. FIG. 21 depicts the end effector jaws 142', 144' in an open position prior to deploying the cutting blade 164'. FIG. 22 depicts the end effector 140' jaws 142', 144' in a partially closed position and partially deployed cutting blade 164'. FIG. 23 depicts the end effector 140' jaws 142', 144' in a closed position as the cutting blade 164' is being deployed.

With reference now to FIGS. 21-23, the embodiment of the articulation section 100' and end effector 140' includes a simultaneous articulation and end effector 140' actuation. As shown in FIG. 21, the upper jaw 142' of the end effector 140' is open to receive tissue 180' between the upper and lower jaws 142', 144'. The upper jaw 144' is pivotally movable about pivot 182' and the lower jaw 142' is rigidly attached to the rigid shaft section 102'. The cutting blade 164' with the sharp distal portion 178' has not yet been deployed. The cutting blade 164' comprises upper and lower flanges 162', 166' that engage respective upper and lower slots (not shown, but described previously in connection with FIGS. 5-7) provided in the upper and lower jaws 144', 142'. The upper and lower flexible bands 165', 167' of the flexible firing element 160' are attached to corresponding upper and lower flanges 162', 166' of the cutting blade 164'. As shown in FIG. 22, as the flexible firing element 160' is advanced distally, the upper jaw 144' begins to close toward the lower jaw 144' and engages the upper and lower flanges 165', 167' of the flexible firing element 160' engage the slots provided in the upper and lower jaws 144', 142' to begin closing the upper jaw 144' against the lower jaw 142' and grasp the tissue 180' located therebetween. As best seen in FIG. 23, as the cutting blade 164' is further advanced distally, the upper jaw 144' closes tightly against the lower jaw 142' to grasp the tissue 180' therebetween to be cut by the sharp distal portion 178' of the cutting blade 164'.

III. Example Articulation Control Configurations

FIGS. 24-27 depict a rotatable articulation control mechanism 400 for activating longitudinal articulation movements according to one embodiment. As shown in FIG. 24, one embodiment of the rotatable articulation control mechanism 400 for controlling the vertical articulation of the articulation section of the electrosurgical instrument 10, 10' comprises a rotation knob 28 and upper and lower articulation bands 122, 124 coupled to rotation knob 28. The upper and lower articulation bands 122, 124 are attached to corresponding upper and lower cylindrical sleeves 402, 404 that include worm gear threaded portions 406, 408 respectively. FIG. 25 is an exploded partial cut-away view of the rotatable articulation control mechanism shown in FIG. 24. As best seen in FIG. 25, the worm gear threaded portions 406, 408 of the corresponding upper and lower cylindrical sleeves 402, 404 meshingly engage with upper and lower planetary worm gears 410, 412 inside the rotation knob 28. As shown in FIG. 26, as the rotation knob 28 of the rotatable articulation control mechanism 400 is rotated in a counterclockwise direction 29" relative to a user, the upper articulation band 122 is advanced distally 414 while the lower articulation band 124 is retracted proximally 416 to cause the articulation section to articulate in a downward vertical direction. As shown in FIG. 27, as the rotation knob 28 of the rotatable articulation control mechanism 400 is rotated in a clockwise direction 29' relative to a user, the upper articulation band 122 is retracted proximally 418 while the lower articulation band 124 is advanced distally 420 to cause the articulation section to articulate in an upward vertical direction.

As shown and described in connection with FIGS. 24-27, the rotatable articulation control knob 28 is operable to selectively advance one articulation band 122 while simultaneously retracting the other articulation band 124; and/or to selectively retract one articulation band 122 while simultaneously advancing the other articulation band 122. In some other versions, the rotatable articulation control knob 28 can be modified to accommodate other implementations without departing from the scope of the present disclosure. For example, as previously discussed in connection with FIG. 17, the articulation control knob 28 can be operable to selectively advance or retract one articulation band 122, 124 while keeping the position of the other articulation band 122, 124 substantially constant, thereby causing articulation section 100 to bend in a vertical plane relative to the longitudinal axis L. Of course, the articulation bands 122, 124 may be substituted with cables and/or various other types of components.

IV. Example Lost Motion Mechanism

Figure 28:
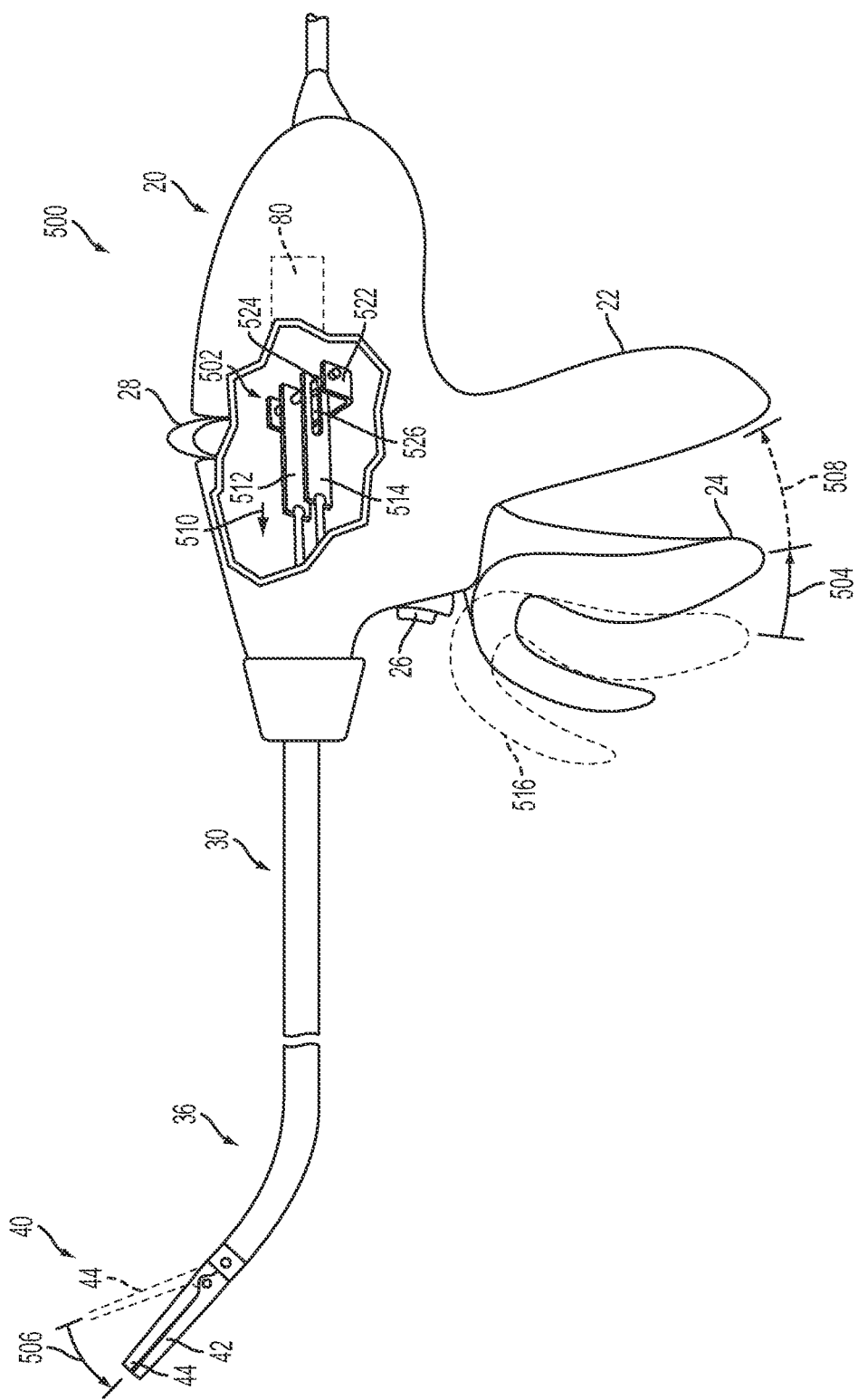
Figure 29:
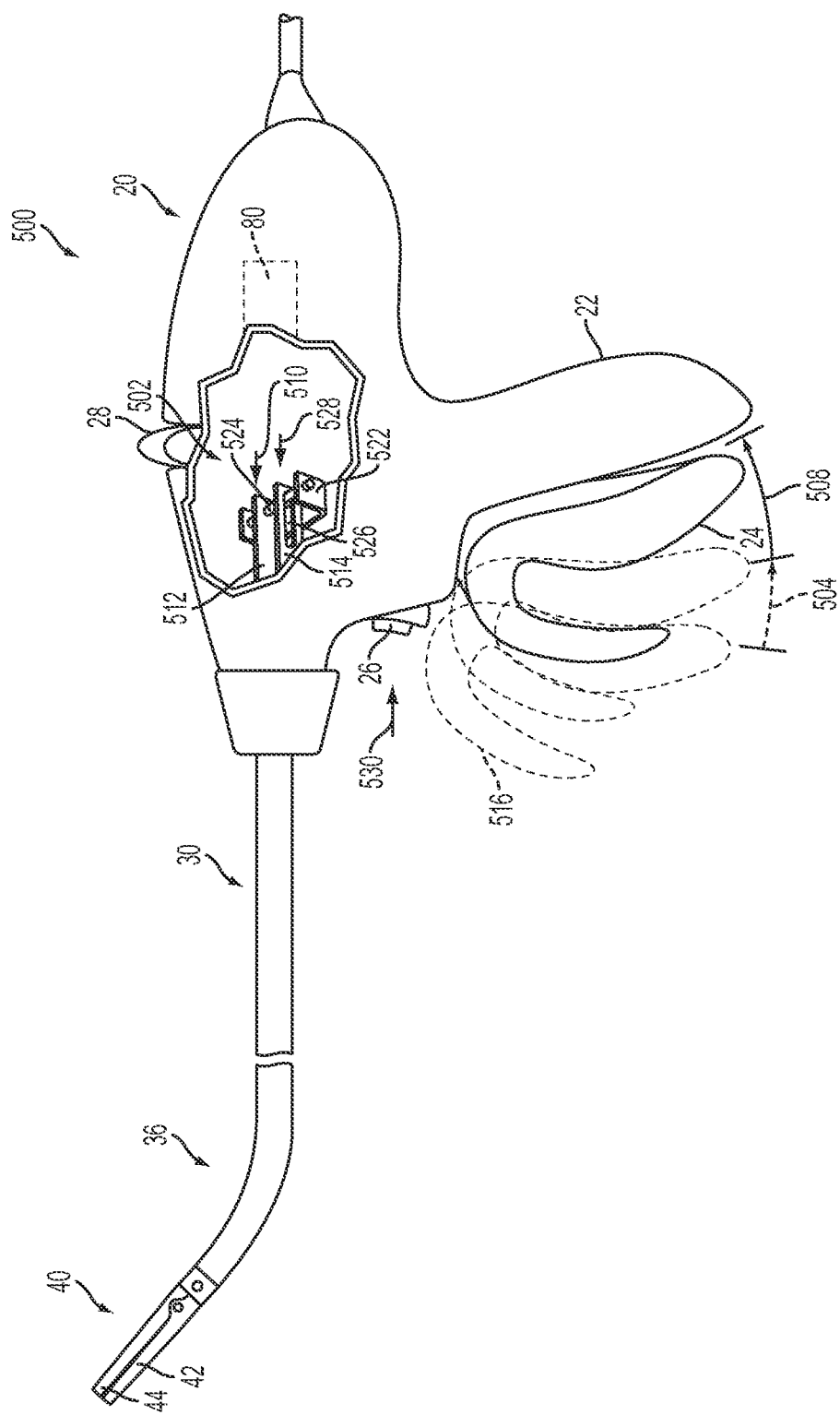

FIGS. 28-30A-C depict a lost motion mechanism 502 in a handpiece 20 portion of an electrosurgical device 500 that enables an initial trigger stroke 504 to actuate 510 a closure linkage 512 to clamp 506 the jaws 42, 44 of an end effector 40 and then a remainder of the stroke 508 throws a cutting blade portion while maintaining the jaws 42, 44 clamped. FIG. 29 depicts the actuation of the cutting blade in response to the remainder of the trigger stroke 508. FIG. 30A depicts the initial state untriggered of the lost motion mechanism 502. FIG. 30B depicts the state of the lost motion mechanism 502 after the initial trigger stroke 504. FIG. 30C depicts the state of the lost motion mechanism 502 after the final trigger stroke 508. It will be appreciated that the electrosurgical device 500 is similar in operation to the previously described electrosurgical devices except for the lost motion mechanism 502 that controls the manner in which the end effector 40 is clamped and the cutting blade is fired by actuating a firing linkage 514. The vertical articulation section 36 of the shaft 30 and the electrosurgical power source 80 operate in a manner similar to the embodiments previously discussed in connection with FIGS. 1-27. FIG. 28 depicts the activation of the end effector 40 jaw 44 in response to the initial trigger stroke 504.

With reference to FIGS. 28 and 30A-B, the trigger 24 is initially in an untriggered position 516 (shown in phantom), which corresponds to the upper jaw 44 (phantom) of the end effector 40 being in an open, unclamped, position. As shown in FIG. 30A, a "U" shaped actuation bar 522, which is operatively coupled to the trigger 24, is coupled to the first and second linkages 512, 514 by a pin 524. The pin 524 is longitudinally fixed within an aperture 525 defined at the proximal end of the first linkage 512. The first linkage 512 is coupled to the upper jaw 44 by way of an actuation bar 518 and the second linkage 514 is coupled to the distal cutting blade by way of a firing bar 520. In the untriggered position 516, the actuation bar 522 and the first and second linkages 512, 514 are fully retracted. The second linkage 514 includes a slot 526 to slidably receive the pin 524, such that the actuator 522 can be advanced distally to actuate 510 the first linkage 512 over a distance equal to the length of the slot 526 in response to the initial trigger stroke 504 before the pin 524 engages the second linkage 514, as shown in FIG. 30B. The pin 526 is slidably movable from a proximal wall 527 defined by the slot 526 to the distal wall 530 defined by the slot 526.

With reference to FIGS. 29 and 30C, after the initial trigger stroke 504 the pin 522 engages a distal wall 530 of the slot 526. Therefore, when the trigger 24 is triggered the remainder of the stroke 508, the second linkage 514 also is engaged to actuate 528 the firing bar 522. The first linkage 512 also is actuated 510 to apply greater clamping force to the tissue clamped between the upper and lower jaws 44, 42. Prior to applying the final trigger stroke 508 to advance the cutting blade, the user activates 530 the activation button 26 to apply energy to seal the tissue.

V. Example Alternative Clamping/Articulation Mechanisms

A. Jaw Closure And Articulation On Same Pivot

FIGS. 31A-C depict alternative articulation mechanisms for the electrosurgical devices previously discussed in connection with FIGS. 1-30, where jaw closure and articulation are on the same pivot. FIGS. 31A-C depict an over under flexible firing element configuration to enable articulation in plane with end effector jaw opening motion. A technique to improve access to vessels and difficult to get at tissue includes articulating the articulation section of an electrosurgical device up and down (vertical) rather than left to right (horizontal) relative to the longitudinal axis L. The present embodiment provides a flexible firing element by connecting flexible bands to the firing element pins rather than vertical strut connecting them. The ability to push on both the top and bottom of the flexible firing element will minimize the tendency of cocking and binding as it is advanced. The flexible firing elements then follow the pins into enclosed upper and lower jaw tracks which prevent the flexible firing elements from buckling as the knife is advanced. Also, the present embodiment provides an improved jaw clamp track which cams the jaws tighter and provides for positive jaw opening. IN accordance with estimated calculations, 45-60 degrees of articulation may be achieved on a 1 in. bend radius for the flexible firing element laminates. In-plane articulation improves access to difficult to get to vessels and arteries, provides positive jaw opening to allow for better dissection and tissue manipulation, and provides improved clamping loads to improve tissue holding force.

FIG. 31A depicts an end effector 600 comprising upper and lower movable jaws 604A, 604B and a rigid outer cam tube 602 that acts as a cinch/cam tube against the contoured outer edges 640A, 640B of the upper and lower jaws 604A, 604B, which act as cam surfaces. The upper and lower movable jaws 604A, 604B are shown in the open position relative to the longitudinal axis L. A first rod 606A is operatively coupled to the upper jaw 604A by a first bar linkage 620A. The first rod 606A is pivotally coupled to the first bar linkage 620A at a first pivot 622A. The upper jaw 604A is pivotally coupled to the first bar linkage 620A at a second pivot 624A. A second rod 606B is operatively coupled to the lower jaw 604B by a second bar linkage 620B. The second rod 606B is pivotally coupled to the second bar linkage 620B at a first pivot 622B. The lower jaw 604B is pivotally coupled to the second bar linkage 620B at a second pivot 6248. As the first and second rods 606A, 606B are advanced distally in the direction indicated by arrows 630, 632, the upper and lower jaws 604A, 604B rotate open as indicated by arrows 608, 610 about the pivot pin 626. Also, as the first and second rods 606A, 606B are driven distally 630, 632 the pivot pin 626 engages the distal wall of a cam slot 628 defined in each of the upper and lower jaws 640A, 640B.

As shown in FIG. 31B, as the first and second rods 606A, 606B are retracted proximally in the direction indicated by arrows 634, 636, the upper and lower jaws 604A, 604B rotate closed as indicated by arrows 612, 614. As the first and second rods 606A, 606B are pulled proximally 634, 636, the pivot pin 626 slides proximally within the cam slot 628. As the rods 606A, 606B are pulled in direction 634, 636, the upper jaw 604A rotates downwardly, slides proximally, and cams upward. In doing so the upper and lower jaws 604A, 604B are pulled into the cinch/cam outer tube 602.

As shown in FIG. 31C, additional compressive clamp forces 616, 618 can be applied to the upper and lower jaws 604A, 604B by continuing to pull the first and second rods 606A, 606B in direction 638 further into the outer cam tube 602. The edge of the outer cam tube 602 acts on the cam surfaces defined by the contoured outer edges 640A, 640B of the upper and lower jaws 604A, 604B as they are pulled into the rigid outer tube 602. The pivot pin 626 now engages a proximal wall of the cam slot 628. As the edge of the outer cam tube 602 cams against the cam surfaces 640A, 640B, additional compressive clamping forces 616, 618 are applied to the upper and lower jaws 604A, 604B. Accordingly, the cam surfaces 640A, 640B, the rigid outer cam tube 602, and the bar linkages 620A, 620B cooperate to improve the mechanical closure strength of the upper and lower jaws 604A, 604B to increase the compressive clamp force of the jaws 604A, 604B. The tension in the rods 606A, 606B significantly improve the maximum clamping compression load between the upper and lower jaws 604A, 604B. The cam slot 628 and the outer cam tube 602 couple to improve tissue retention. The hoop of the outer cam tube 602 significantly improves maximum cinching load.

As shown in FIGS. 31A-C, the linkage based closure configuration derives mechanical advantage from the relationship of where the bar links 620A, 620B connect to the upper and lower jaws 604A, 604B at 624A, 624B. The embodiment illustrated in FIGS. 31A-C is a hybrid linkage/cam tube configuration where the end effector closure load is generated in a tension member. This configuration combines the advantages of the linkage configuration, which provides a large range of motion of the upper and lower jaws 604A, 604B and the high mechanical advantage provided by the outer cam tube 602 configuration, which is capable of creating an order of magnitude higher compression load by utilizing a cinch/cam action. The hoop stress of the outer cam tube 602 also is better suited to handle stresses due to the better moment of inertia and boundary conditions.

FIGS. 32A-E depict alternative articulation mechanisms for the electrosurgical devices previously discussed in connection with FIGS. 1-30, where jaw closure and articulation are on the same pivot. The present embodiment provides separate and distinct clamping and cutting with a drive and chase link arrangement. The dual bar link interdependent jaw actuation configuration discussed in connection with FIGS. 31A-C, improves the overall clamping mechanism. FIGS. 32A-E depict a control configuration that can easily switch between articulation and clamping (open/close) with a drive and chase link arrangement, as described in more detail below. This provides the benefit of improved articulation via the motion of the jaws and improved clamping using two independent actuators and a following actuator, rather than three independent actuators. In the present embodiment, articulation is accomplished by over closing the lower jaw and allowing the upper jaw to passively lead due to the geometry between the upper and lower links. The upper link does not move as the lower link controls articulation. When the upper link is pulled relative to the lower link, however, the end effector clamps.

Figure 32A:
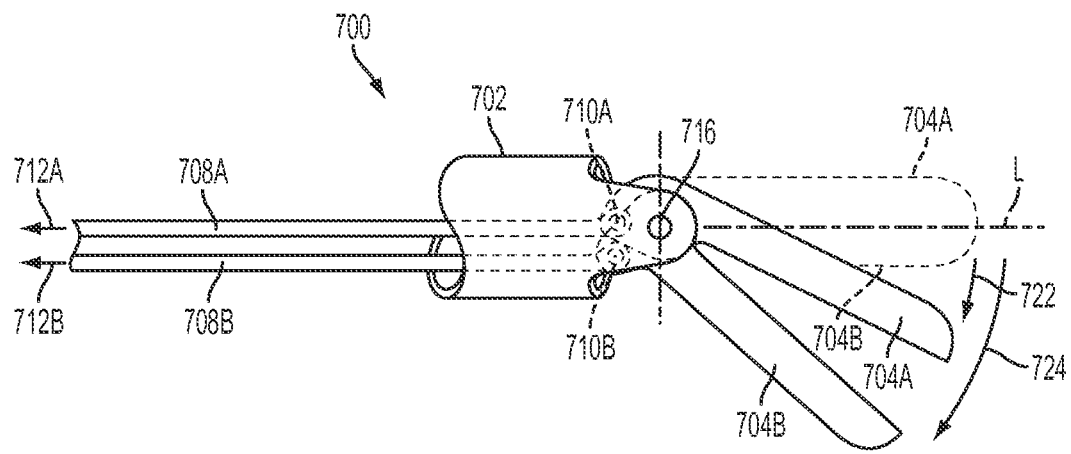

FIG. 32A depicts an end effector 700 comprising upper and lower movable jaws 704A, 704B. The upper and lower movable jaws 704A, 704B are pivotally connected to a rigid outer tube 702 at a pivot 716. First and second rods 708A, 708B are pivotally connected to the upper and lower jaws 704A, 704B at respective pivots 710A, 710B. The first and second rods 708A, 708B are employed to actuate (open/close, clamp) and articulate the upper and lower jaws 704A, 704B. From an aligned position, where the upper and lower jaws 704A, 704B are substantially aligned with the longitudinal axis L (shown in phantom), the upper and lower jaws 704A, 704B can be articulated downwardly and opened by retracting (pulling) the rods 708A, 708B in a proximal direction as indicated by arrows 712A, 712B. Accordingly, as the rods 708A, 708B are pulled proximally 712A, 712B, the upper jaw 704A rotates downwardly about pivot 716 over an arc indicated by arrow 722 and the lower jaw 704B rotates downwardly about the pivot 716 over a longer arc indicated by arrow 724. Upon rotating in a downwardly direction, the upper and lower jaws 704A, 704B are opened.

Figure 32B:
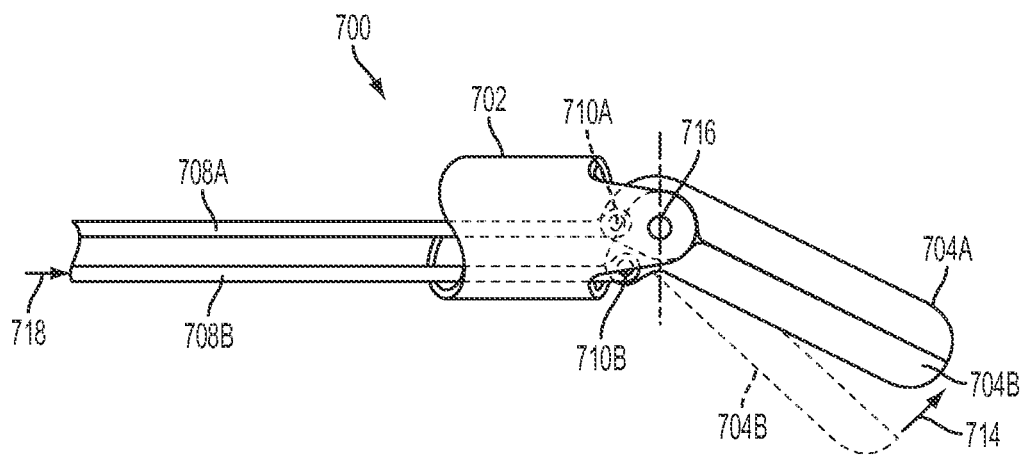
Figure 32C:
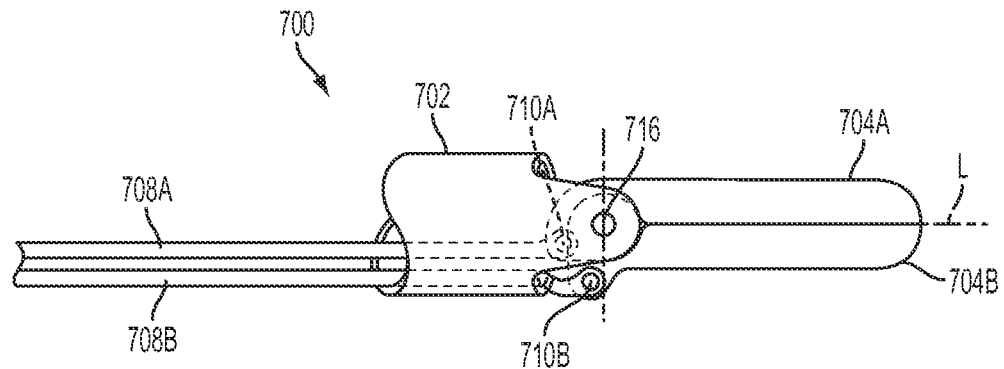

FIG. 32B depicts the lower jaw 704B closing against the upper jaw 704A when located in the downwardly articulated position illustrated in FIG. 32A. As shown in FIG. 32B, advancing (pushing) the second rod 708B distally as indicated by arrow 718 causes the lower jaw 704B to rotate upwardly about the pivot 716 from an open position (indicated in phantom) over an arc indicated by arrow 714 until it closes (clamps) against the upper jaw 704A. From this clamped position, continuing to advance (push) the second rod 708B distally 718 causes both upper and lower jaws 704A, 704B to rotate together back to the longitudinal aligned position shown in FIG. 32C.

Figure 32D:
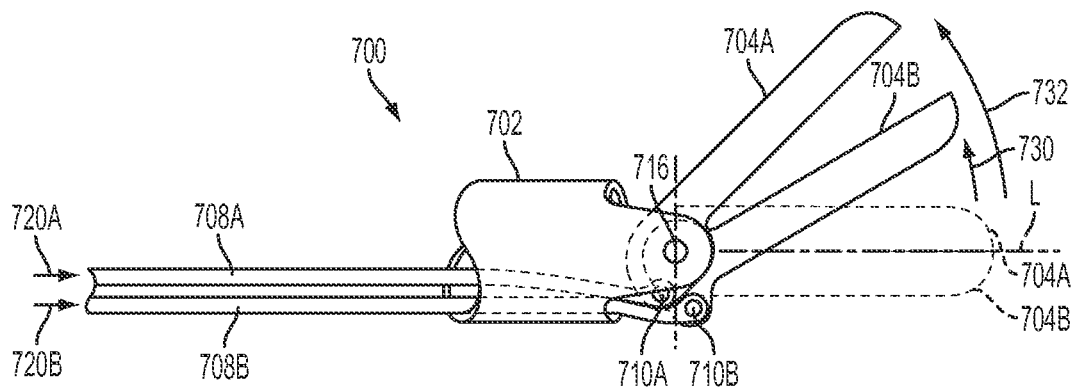

FIG. 32D depicts the upper and lower movable jaws 704A, 704B articulated upwardly. From the longitudinally aligned position, the upper and lower jaws 704A, 704B can be rotated upwardly about the pivot 716 by advancing (pushing) the first and second rods 708A, 708B distally as indicated by arrows 720A, 720B. As the rods 708A, 708B are advanced (pushed) distally 720A, 720B, the upper jaw 704A rotates upwardly about pivot 716 over an arc indicated by arrow 732 and the lower jaw 704B rotates upwardly about the pivot 716 over a shorter arc indicated by arrow 730. Upon rotating in an upwardly direction, the upper and lower jaws 704A, 704B are opened.

Figure 32E:
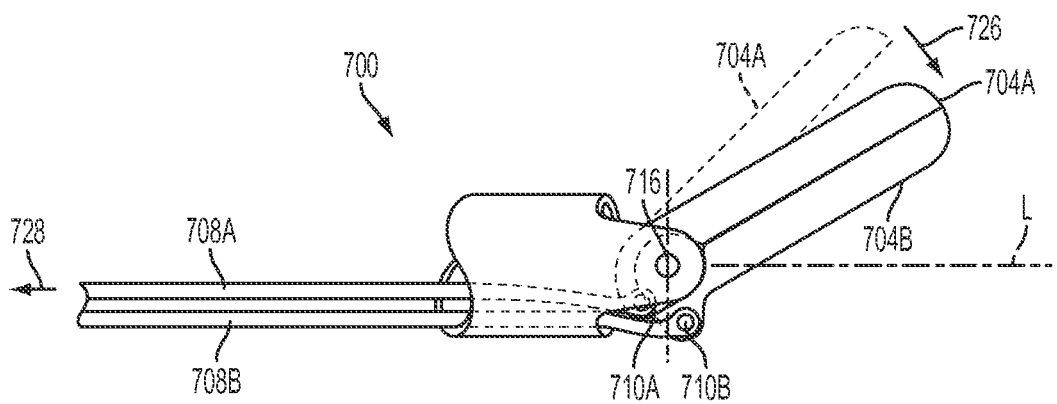

FIG. 32E depicts the upper jaw 704A closing against the lower jaw 704B when located in the upwardly articulated position illustrated in FIG. 32D. As shown in FIG. 32E, retracting (pulling) the first rod 708A proximally 728 causes the upper jaw 704A to rotate downwardly about the pivot 716 from an open position (indicated in phantom) over an arc indicated by arrow 726 until it closes (clamps) against the lower jaw 704B. From this position, continuing to retract (pull) the first rod 708A proximally 728 causes both upper and lower jaws 704A, 704B to rotate together back to the longitudinally aligned position.

It will be appreciated that the embodiment illustrated in connection with FIGS. 32A-E that includes link articulation with a cam clamping mechanism, isolates clamping loads to the end effector 700. The minimal number of components in the force/restraint loop employed by this embodiment increases the clamping/gripping load available. The handle is the ground against which the advancing load is applied. If the load loop comprises merely two anvils and a cam therebetween, then there is much less play and much higher loads can be exerted. In the embodiment described above, a single cam lobe interconnects upper and lower jaws 704A, 704B. In the distal position, the upper and lower jaws 704A, 704B are actively cammed open to spread the load between the jaws 704A, 704B. In the proximal position, the jaws 704A, 704B are cammed shut. The activation rod 708A, 708B that moves a lobe from one position to the other only experiences forces back driven to the handle as it activates from one position to the other. The lobe is configured to move from a position concentric to the upper jaw 704A pin to a position concentric to the lower jaw 704B pin. Accordingly, the end effector 700 forces are not driven back to handle and allows closure of the jaws 704A, 704B to be completely separate from knife or I-beam actuation. This embodiment, is compatible with articulation of the end effector 700 about the same axis of the jaws 704A, 704 open/closure.

B. Independent Clamping And Blade Actuation With Dual Rotary Clamping Mechanisms To free up as much inner tube diameter as possible while maintaining the benefits of independent jaw control, the present embodiment, converts the push-pull type actuators to rotatable drive tubes. Each of the rotatable drive tubes comprise a hemispherical gear tooth configuration at a distal end that is coupled to one of the two jaws to controls its motions. Rotating the two rotatable drive tubes in the same direction and at the same time, causes the pair of jaws to articulate at whatever opening state they are in a vertical (up or down) direction. If the tubes are rotated in opposite directions the jaws either open or close depending on which opposite directions. In one embodiment, three concentric tubes are provided, a ground tube and one drive tube for each jaw. The inner diameter of the innermost tube is free to receive other mechanisms and may be employed for a wave guide, cutting blade beam, or any other secondary actuator as may be desired. The tooth strength is capable of generating several pounds of end-effector tip load before the teeth begin to yield. Another advantage of rotary motion for closure and articulation is the possibility of running these rotations through another articulation joint first, or even at 90 degrees to the jaw open/closing/articulation axis. Specific embodiments will now be described hereinbelow in connection with FIGS. 33-37A-C.

FIGS. 33-37A-C depict alternative articulation, clamping, and blade actuation mechanisms for the electrosurgical devices previously discussed in connection with FIGS. 1-30. FIGS. 33-37A-C depict articulation, clamping, and blade actuation mechanisms employing two rotations and a push-pull blade rather than a two push-pull articulation/clamping and one push-pull blade to perform the same functions.

FIG. 33 depicts an exploded perspective view of one embodiment of an end effector 800 with articulation, clamping, and blade actuation mechanisms employing two rotations and a push-pull blade rather than two push-pull articulation/clamp and push-pull blade to perform the same functions. FIG. 34 depicts the end effector 800 of FIG. 33 with left and right jaws 806, 808 in a closed (clamped) configuration and FIG. 35 depicts a side elevational partial cutaway view of the end effector 800 shown in FIG. 33 with the jaws 806, 808 in an open (unclamped) configuration. With reference now to FIGS. 33-35, the end effector 800 comprises a rotatable inner tube 802 and a rotatable outer tube 804. The inner tube 802 is rotatably disposed within the outer tube 804. The inner tube 802 is rotatably coupled to a lower jaw 806 (left from the perspective of the user) and the outer tube 804 is rotatably coupled to an upper jaw 808 (right from the perspective of the user). The inner and outer tubes 802, 804 each comprise a hemispherical gear tooth 816, 818 located on a distal end thereof. The jaws 806, 808 each comprise a gear 820, 822 located on a proximal end thereof, where each of the gears 820, 822 comprises a hemispherical gear tooth 824, 826 configured to mesh with the hemispherical gear tooth 816, 818 located on a distal end of each one of the inner and outer tubes 802, 804. A third longitudinal tube 810 is disposed within the inner diameter of the inner tube 802. The third tube 810 comprises left and right axles 812, 814 about which the left (lower) and right (upper) jaws 806, 808 rotate. Each of the gears 820, 822 define a hub 830, 832 to receive one end of the corresponding axle 812, 814. Accordingly, the jaws 806, 808 are rotatably coupled to the corresponding inner and outer tubes 802, 804 and rotate about the axles 812, 814 in response to the rotation of the inner and outer tubes 802, 804, alone or in combination. The jaws 806, 808 also comprise a slot 828 to slidably receive a cutting blade (not shown).

FIGS. 36A-C depict side elevational partial cut away views of the end effector 800 of FIG. 33 during an articulation sequence. FIG. 36A depicts a configuration where the jaws 806, 808 are in a clamped neutral horizontal position. FIG. 36B depicts an upwardly articulation of the clamped jaws 806, 808 that is accomplished by rotating the rotatable inner tube 802 and the outer tube 804 in the same direction counterclockwise (CCW) (left). FIG. 36C depicts a downwardly articulation of the clamped jaws 806, 808 that is accomplished by rotating the rotatable inner tube 802 and the outer tube 804 in the same direction clockwise (CW) (right).

FIGS. 37A-C depict side elevational partial cut away views of the end effector 800 of FIG. 33 during a jaw actuation sequence from an upward predetermined articulation configuration. FIG. 37A depicts the end effector 800 with the lower jaw 806 rotated in a clamped position against the upper jaw 808 that is accomplished by rotating the inner tube 802 clockwise (right) and the outer tube 804 counterclockwise (left). FIG. 37B depicts a downwardly rotation of the lower jaw 806 away from the upper jaw 808 to an open position. This is accomplished by rotating the inner tube 802 clockwise (right) while holding the outer tube 804 in a fixed position. FIG. 37C depicts the upwardly rotation of the lower jaw 806 that is accomplished by rotating the inner tube 802 clockwise (right) and the outer tube 804 counterclockwise (left).

FIG. 38 depicts an exploded perspective view of one embodiment of an end effector 900 with articulation and clamping mechanism and an ultrasonic blade 903 employing two rotatable tubes 902, 904 for articulation and clamping. FIG. 38 depicts an exploded perspective view of one embodiment of an end effector 900 with an articulation and clamping mechanism and an ultrasonic blade 903. The articulation and clamping mechanism employs an inner rotating tube 902 and an outer rotating tube 904. The end effector 900 comprises a rotatable upper jaw 908 and a rotatable lower jaw 906. The inner tube 902 is rotatably coupled to the lower jaw 906 (left from the perspective of the user) and the outer tube 904 is rotatably coupled to the upper jaw 908 (right from the perspective of the user). The inner and outer tubes 902, 904 each comprise a hemispherical gear tooth 916, 918 located on a distal end thereof. The jaws 906, 908 each comprise a gear 920, 922 located on a proximal end thereof, where each of the gears 920, 922 comprises a hemispherical gear tooth 924, 926 configured to mesh with the hemispherical gear tooth 916, 918 located on a distal end of each one of the inner and outer tubes 902, 904. A third longitudinal tube 910 is disposed within the inner diameter of the inner tube 902. The third tube 910 comprises left and right axles 912, 914 about which the left (lower) and right (upper) jaws 906, 908 rotate. Each of the gears 920, 922 define a hub 930, 932 to receive one end of the corresponding axle 912, 914. Accordingly, the jaws 906, 908 are rotatably coupled to the corresponding inner and outer tubes 902, 904 and rotate about the axles 912, 914 in response to the rotation of the inner and outer tubes 902, 904, alone or in combination.

The ultrasonic blade 903 is acoustically coupled to a flexible waveguide 933. The ultrasonic blade 903 is driven by an ultrasonic transducer (not shown) which is driven by an ultrasonic generator (not shown). The ultrasonic generator electrically energizes the ultrasonic transducer at a predetermined voltage to cause the ultrasonic transducer to mechanically vibrate at 55.5 kHz, or other suitable ultrasonic frequencies. These mechanical vibrations are acoustically coupled to the flexible waveguide 933, which acoustically couples the ultrasonic vibrations to the ultrasonic blade 903 causing the ultrasonic blade 903 to also vibrate at ultrasonic frequencies. The mechanical displacements of the ultrasonic blade 903 render it useful for treating tissue and in particular, the excited ultrasonic blade 903 can be used to cut and coagulate tissue without the assistance of a mechanical cutting blade and/or an electrosurgical cauterization tool. Ultrasonic blades and their operation are well known in the art and will not be described herein in detail.

FIGS. 39A-C depict side elevational partial cut away views of the end effector 900 of FIG. 38 during a jaw actuation sequence, where FIG. 39A depicts the end effector 900 with the lower jaw 906 and the ultrasonic blade 903 rotated to a clamped neutral longitudinal position. FIG. 39B depicts the upper jaw 908 rotating upwardly away from the lower jaw 906 to an open position by rotating the inner tube 902 clockwise and rotating the outer tube counterclockwise 904. FIG. 39C depicts the lower jaw 906 rotating toward the upper jaw 908 and clamping the ultrasonic blade 903 therebetween by holding the inner tube 902 and rotating the outer tube 908 clockwise. The lower jaw 908 comprises an isolation contact point 934 used to vibrationally isolate the lower jaw 906 from the ultrasonic blade 903. Accordingly, the contact point 934 is located on the lower jaw 906 such that it contacts the ultrasonic blade 903 at a node, which is a location of zero or substantially zero mechanical vibration. The contact point 934 may comprise a pad 936. The pad 936 may be made of any suitable polymer and in particular, in one embodiment, the pad 936 is made of TEFLON. During an upward articulation to clamp the jaws 906, 908, the contact pad 936 contacts the ultrasonic blade 903 at a node and pushes the ultrasonic blade 903 towards the upper jaw 908. In operation, tissue, such as a blood vessel, is clamped between the ultrasonic blade 903 and the upper jaw 908. Once the tissue is clamped, the ultrasonic blade 903 is energized. The mechanical vibrations acting on the clamped tissue cuts and coagulates the tissue.

VI. Other Example Features

While the examples herein are described mainly in the context of electrosurgical instruments, it should be understood that the teachings herein may be readily applied to a variety of other types of medical instruments. By way of example only, the teachings herein may be readily applied to tissue graspers, tissue retrieval pouch deploying instruments, surgical staplers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The disclosed embodiments have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

It is worthy to note that any reference to "one aspect," "an aspect," "one embodiment," or "an embodiment" means that a particular feature, structure, or characteristic described in connection with the aspect is included in at least one aspect. Thus, appearances of the phrases "in one aspect," "in an aspect," "in one embodiment," or "in an embodiment" in various places throughout the specification are not necessarily all referring to the same aspect.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely examples and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

In summary, numerous benefits have been described which result from employing the concepts described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical application to thereby enable one of ordinary skill in the art to utilize the various embodiments and with various modifications as are suited to the particular use contemplated. It is intended that the claims submitted herewith define the overall scope.

Various aspects of the subject matter described herein are set out in the following numbered clauses:

1. An apparatus, comprising: a shaft section extending longitudinally along a first plane; an end effector comprising a first jaw and a second jaw configured to pivotally open and close in a second plane relative to the first plane about a pivot point, wherein the first plane is orthogonal to the second plane; and an articulation section disposed between the shaft section and the end effector, the articulation section configured to articulate in the second plane relative to the first plane in response to a rotatable articulation control mechanism; wherein at least one of the first and second jaws comprises an electrode.

2. The apparatus of clause 1, wherein the articulation section comprises a molded member that defines at least one slot and at least one recess.

3. The apparatus of clause 2, comprising a first slot extending longitudinally along the length of the molded member and oriented transversely relative to the axis of the molded member, the first slot comprising an opening at a top portion of the molded member and terminating within a bottom portion of the molded member.

4. The apparatus of clause 3, comprising a second slot extending longitudinally along the length of the molded member and oriented transversely relative to the axis of the molded member, the second slot configured to slidably receive an actuation member to control the actuation of the first and second jaws.

5. The apparatus of clause 2, comprising a longitudinally slidable blade.

6. The apparatus of clause 5, wherein the blade comprises upper and lower flanges and wherein the least one slot is configured to slidably receive upper and lower flexible bands of a flexible firing element, wherein the flexible firing element comprises an upper flexible band connected to an upper flange portion of the blade and a lower flexible band connected to a lower flange portion of the distal blade.

7. The apparatus of clause 2, wherein a first recess is configured to receive a first articulation band and a second recess is configured to receive a second articulation band, wherein the first and second articulation bands are spaced apart transversely from a longitudinal axis defined by the first and second articulation bands, wherein distal ends of the first and second articulation bands are secured to a distal end of the articulation section, and wherein proximal ends of the first and second articulation bands are in operatively coupled to the rotatable articulation control mechanism.

8. The apparatus of clause 7, wherein the rotatable control mechanism is operable such that when the control mechanism is rotated in a first direction relative to a user, the first articulation band is advanced distally while the second articulation band is retracted proximally to cause the articulation section to articulate in a first direction along the second plane defined by the longitudinally extending shaft section and the open and close direction of the first and second jaws.

9. The apparatus of clause 8, wherein the rotatable control mechanism is operable such that when the control mechanism is rotated in a second direction relative to a user, the first articulation band is retracted proximally while the second articulation band is advanced distally to cause the articulation section to articulate in a second direction along the second plane defined by the longitudinally extending shaft section and the open and close direction of the first and second jaws.

10. An apparatus, comprising: a shaft section extending longitudinally along a first plane; an end effector comprising a first jaw and a second jaw configured to pivotally open and close in a second plane relative to the first plane about a pivot point, wherein the first plane is orthogonal to the second plane; and an articulation section disposed between the shaft section and the end effector, the articulation section configured to articulate in the second plane relative to the first plane in response to a lost motion mechanism operatively coupled to a trigger mechanism; wherein at least one of the first and second jaws comprises an electrode.

11. The apparatus of clause 10, wherein the lost motion mechanism comprises: a first linkage defining an aperture to receive a pin at a proximal end and coupled to an actuation bar at a distal end, wherein the pin is longitudinally fixed within the aperture; a second linkage defining a slot to receive the pin at a proximal end and coupled to a firing bar at a distal end, the slot defining a proximal wall and a distal wall, wherein the pin is longitudinally slidably movable within the slot; and an actuator operatively coupled to the trigger mechanism, the actuator defining first and second sidewalls defining first and second apertures to receive the pin therethrough.

12. The apparatus of clause 11, wherein the lost motion mechanism is configured to actuate the actuation bar to clamp the first and second jaws of the end effector during an initial trigger stroke and to actuate the firing bar during a remainder of the trigger stroke while maintaining the first and second jaws in the clamped position.

13. An apparatus, comprising: an end effector comprising a first jaw and a second jaw configured to pivotally open and close in a first plane relative to a second plane defined by the longitudinally extending shaft section, wherein the first plane is orthogonal to the second plane, the first and second jaws comprising contoured outer edges and a cam slot defined in each of the first and second jaws, the cam slots configured to receive a pivot pin therethrough about which the first and second jaws open and close about a pivot point; and a rigid outer cam tube extending longitudinally, the rigid outer cam tube configured to act upon the contoured outer edges of the first and second jaws; wherein the end effector is configured to articulate in the first plane relative to the second plane in response to the cam tube slidably moving in a longitudinal direction, wherein the end effector articulates about the pivot point.

14. The apparatus of clause 13, comprising: a first rod coupled to the first jaw by a first bar linkage at a first pivot, the first rod slidably movable longitudinally; and a second rod coupled to the second jaw by a second bar linkage at a second pivot, the second rod slidably movable longitudinally.

15. The apparatus of clause 14, wherein the first jaw is pivotally coupled to the first bar linkage at the second pivot and the second jaw is pivotally coupled to the second bar linkage at the second pivot.

16. The apparatus of clause 15, wherein as the first and second rods are slidably advanced distally, the pivot pin engages a distal wall defined by the cam slot causing the first and second jaws to rotate about the pivot pin to an open position.

17. The apparatus of clause 15, wherein as the first and second rods are slidably retracted proximally, the first and second jaws to rotate about the pivot pin to a closed position.

18. The apparatus of clause 17, wherein as the first and second rods are further slidably retracted proximally such that the pivot pin engages a proximal wall defined by the cam slot, additional compressive closure force is applied to the first and second jaws as the edge of the outer cam tube acts on the cam surfaces defined by the contoured outer edges of the first and second jaws.

19. An apparatus, comprising: an end effector comprising a first jaw and a second jaw configured to pivotally open and close in a plane relative to a longitudinal axis, the first and second jaws comprising contoured outer edges and an aperture defined in each of the first and second jaws, the apertures configured to receive a pivot pin therethrough about which the first and second jaws open and close about a pivot point; a rigid outer tube, a distal end of the rigid outer tube pivotally coupled to proximal ends of the first and second jaws; and a drive and chase link arrangement; wherein the end effector is configured to articulate in the plane relative to the longitudinal axis in response to the cam tube slidably moving in a longitudinal direction; wherein the end effector articulates about the pivot point.

20. The apparatus of clause 19, comprising: a first rod coupled to the first jaw at a first pivot, the first rod slidably movable longitudinally; and a second rod coupled to the second jaw by a second bar linkage at a second pivot, the second rod slidably movable longitudinally.

21. The apparatus of clause 20, wherein the first and second rods are operable to actuate and articulate the upper and lower jaws.

22. The apparatus of clause 21, wherein from a substantially longitudinally aligned position, the first and second jaws are downwardly rotatable and opened about the pivot pin when the first and second rods are retracted in a proximal direction.

23. The apparatus of clause 22, wherein from the downwardly articulated position, the second jaw is closed against the first jaw when the second rod is advanced in a distal direction.

24. The apparatus of clause 23, wherein from the clamped position, the first and second jaws are rotatable about the pivot pin when the second rod is further advanced in a distal direction.

25. The apparatus of clause 21, wherein from a substantially longitudinally aligned position, the first and second jaws are upwardly rotatable about the pivot pin when the first and second rods are advanced in a distal direction.

26. The apparatus of clause 25, wherein the first and second jaws are rotatable upwardly and opened about the pivot pin when the first and second rods are advanced in a distal direction.

27. The apparatus of clause 26, wherein the first jaw is closed against the second jaw when the first rod is retracted proximally causing the first jaw to rotate downwardly about the pivot point from an open position.

28. The apparatus of clause 27, wherein the first and second jaws are rotatable downwardly and closed when the first rod is further retracted in a proximal direction.

29. An apparatus, comprising: an end effector comprising a first jaw and a second jaw configured to pivotally open and close in a plane relative to a longitudinal axis about a pivot point, the first and second jaws each define a hub to receive first and second axles therethrough about which the first and second jaws pivotally open and close; an outer tube rotatable about the longitudinal axis; and an inner tube disposed within the outer tube, the inner tube rotatable about the longitudinal axis; wherein the outer tube is rotatably coupled to the first jaw and the inner tube is rotatably coupled to the second jaw; wherein the end effector is configured to articulate in the plane relative to the longitudinal axis in response to rotation of the inner or outer tubes about the longitudinal axis; and wherein the end effector articulates about the pivot point.

30. The apparatus of clause 29, wherein the inner and outer tubes each comprise a hemispherical gear tooth located on a distal end thereof.

31. The apparatus of clause 30, wherein the first and second jaws each comprise a gear located on a proximal end thereof, where each of the gears comprises a hemispherical gear tooth configured to mesh with the hemispherical gear tooth located on the distal end of each one of the inner and outer tubes.

32. The apparatus of clause 29, comprising a third tube disposed within the inner tube.

33. The apparatus of clause 32, wherein the third tube comprises the first and second axles about which the first and second jaws pivotally rotate.

34. The apparatus of clause 29, comprising an ultrasonic blade.

35. The apparatus of clause 34, wherein the ultrasonic blade is acoustically coupled to a flexible waveguide.

36. The apparatus of clause 34, wherein the second jaw comprises a pad.

The invention claimed is:

1. An apparatus, comprising:
a shaft section extending longitudinally along a first plane;
an end effector comprising a first jaw and a second jaw configured to pivotally open and close in a second plane relative to the first plane about a pivot point, wherein the first plane is orthogonal to the second plane;
an articulation section disposed between the shaft section and the end effector, the articulation section configured to articulate in the second plane relative to the first plane in response to a rotatable articulation control mechanism, the articulation section comprising a molded member that defines at least one slot and at least one recess; the at least one slot comprising a first slot extending longitudinally along the length of the molded member, the first slot comprising an opening at one side of the molded member and terminating within the molded member on another side;
a longitudinally slidable blade comprising an upper flange and a lower flange;
a flexible firing element comprising upper and lower flexible bands slidably positioned within the at least one slot, the upper flexible band connected to the upper flange of the blade and the lower flexible band connected to the lower flange of the blade;
wherein at least one of the first and second jaws comprises an electrode.

2. The apparatus of claim 1, wherein the at least one slot further comprises a second slot extending longitudinally along the length of the molded member the second slot configured to slidably receive an actuation member to control the actuation of the first and second jaws.

3. The apparatus of claim 1, wherein the at least one recess comprises a first recess configured to receive a first articulation band and a second recess configured to receive a second articulation band, wherein the first and second articulation bands are spaced apart relative to each other in the second plane, wherein distal ends of the first and second articulation bands are secured to a distal end of the articulation section, and wherein proximal ends of the first and second articulation bands are operatively coupled to the rotatable articulation control mechanism.

4. The apparatus of claim 3, wherein the rotatable control mechanism is operable such that when the control mechanism is rotated in a first direction, the first articulation band is advanced distally while the second articulation band is retracted proximally to cause the articulation section to articulate in a first direction along the second plane defined by the longitudinally extending shaft section and the open and close direction of the first and second jaws.

5. The apparatus of claim 4, wherein the rotatable control mechanism is operable such that when the control mechanism is rotated in a second direction opposite of the first direction, the first articulation band is retracted proximally while the second articulation band is advanced distally to cause the articulation section to articulate in a second direction along the second plane defined by the longitudinally extending shaft section and the open and close direction of the first and second jaws.

6. An apparatus, comprising:
a shaft section extending longitudinally along a first plane;
an end effector comprising a first jaw and a second jaw configured to pivotally open and close in a second plane relative to the first plane about a pivot point, wherein the first plane is orthogonal to the second plane; and
an articulation section disposed between the shaft section and the end effector, the articulation section configured to articulate in the second plane relative to the first plane in response to a lost motion mechanism operatively coupled to a trigger mechanism;
wherein at least one of the first and second jaws comprises an electrode; and
wherein the lost motion mechanism comprises:
a first linkage defining an aperture to receive a pin at a proximal end and coupled to an actuation bar at a distal end, wherein the pin is longitudinally fixed within the aperture;
a second linkage defining a slot to receive the pin at a proximal end and coupled to a firing bar at a distal end, the slot defining a proximal wall and a distal wall, wherein the pin is longitudinally slidably movable within the slot; and an actuator operatively coupled to the trigger mechanism, the actuator defining first and second sidewalls defining first and second apertures to receive the pin therethrough.

7. The apparatus of claim 6, wherein the lost motion mechanism is configured to actuate the actuation bar to clamp the first and second jaws of the end effector during an initial trigger stroke and to actuate the firing bar during a remainder of the trigger stroke while maintaining the first and second jaws in the clamped position.

* * * * *